US012102679B2

(12) United States Patent
Zhu et al.

(10) Patent No.: US 12,102,679 B2
(45) Date of Patent: *Oct. 1, 2024

(54) FcRn-TARGETED THERAPEUTICS FOR THE TREATMENT OF ANTIBODY-MEDIATED AUTOIMMUNE AND ALBUMIN-MEDIATED DISEASE

(71) Applicant: University of Maryland, College Park, College Park, MD (US)

(72) Inventors: Xiaoping Zhu, Clarksville, MD (US); Xiaoyang Liu, Adelphi, MD (US)

(73) Assignee: UNIVERSITY OF MARYLAND, COLLEGE PARK, College Park, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 17/897,885

(22) Filed: Aug. 29, 2022

(65) Prior Publication Data

US 2023/0181723 A1  Jun. 15, 2023

Related U.S. Application Data

(63) Continuation of application No. 16/799,605, filed on Feb. 24, 2020, now Pat. No. 11,471,526.

(60) Provisional application No. 62/853,995, filed on May 29, 2019, provisional application No. 62/809,284, filed on Feb. 22, 2019.

(51) Int. Cl.
| | |
|---|---|
| *A61K 39/245* | (2006.01) |
| *A61K 38/16* | (2006.01) |
| *C12N 7/00* | (2006.01) |
| *C12N 15/113* | (2010.01) |

(52) U.S. Cl.
CPC .......... *A61K 39/245* (2013.01); *A61K 38/162* (2013.01); *C12N 7/00* (2013.01); *C12N 15/1131* (2013.01); *C12N 2710/16133* (2013.01)

(58) Field of Classification Search
CPC ...... A61K 39/245; A61K 38/162; C12N 7/00; C12N 15/1131; C12N 2710/16133; C12N 2710/16122; C12N 2710/16134; C12N 15/1137; C12N 15/1138; C12N 2310/14; C07K 14/005; C12Y 203/02

See application file for complete search history.

(56) References Cited

U.S. PATENT DOCUMENTS

| | | | |
|---|---|---|---|
| 2005/0019344 | A1 | 1/2005 | Khanna et al. |
| 2012/0213780 | A1 | 8/2012 | Zhu et al. |
| 2016/0024187 | A1 | 1/2016 | Zhu |
| 2019/0060440 | A1 | 2/2019 | Zhu et al. |
| 2019/0359655 | A1 | 11/2019 | Zhu et al. |

OTHER PUBLICATIONS

Weston K, Barrell BG. RecName: Full=Unique short US11 glycoprotein; AltName: Full=Protein HXLF1; AltName: Full=gpUS11; Flags: Precursor. UniProtKB/Swiss-Prot: P09727.1. Dep. Apr. 24, 1993. (Year: 1993).*
Rawlinson et al., "Congenital Cytomegalovirus Infection in Pregnancy and the Neonate: Consensus Recommendations for Prevention, Diagnosis, and Therapy," Lancet Infect Dis., Jun. 2017; vol. 17; pp. e177-e188.
Klenerman et al., "T Cell Responses to Cytomegalovirus," Nature Reviews | Immunology, Jun. 2016, vol. 16; pp. 367-377.
Biron et al., "Severe Herpesvirus Infections in an Adolescent Without Natural Killer Cells," The New England Journal of Medicine, Jun. 29, 1989, vol. 320, No. 26; pp. 1731-1735.
Kuijpers et al., "Human NK Cells Can Control CMV Infection in the Absence of T Cells," Blood, Aug. 1, 2008, vol. 112, No. 3; pp. 914-915.
Ahn et al., "The ER-Luminal Domain of the HCMV Glycoprotein US6 Inhibits Peptide Translocation by TAP," Immunity, May 1997, vol. 6; pp. 613-621.
Hengel et al., "A Viral ER-Resident Glycoprotein Inactivates the MHC-Encoded Peptide Transporter," Immunity, May 1997, vol. 6; pp. 623-632.
Lehner et al., "The human cytomegalovirus US6 glycoprotein inhibits transporter associated with antigen processing-dependent peptide translocation," Proc Natl Acad Sci U S A., Jun. 1997, vol. 94; pp. 6904-6909.
Jones et al., "Human cytomegalovirus US3 impairs transport and maturation of major histocompatibility complex class heavy chains," Proc Natl Acad Sci U S A, Oct. 1996, vol. 93; pp. 11327-11333.
Ahn et al., "Human cytomegalovirus inhibits antigen presentation by a sequential multistep process," Proc Natl Acad Sci U S A. (PNAS), Oct. 1996, (Immunology), vol. 93; pp. 10990-10995.
Park et al., "The HCMV membrane glycoprotein US10 selectively targets HLA-G for degradation," The Journal of Experimental Medicine, Aug. 30, 2010, vol. 207, No. 9; pp. 2033-2041.
Wiertz et al., "The Human Cytomegalovirus US11 Gene Product Dislocates MHC Class I Heavy Chains from the Endoplasmic Reticulum to the Cytosol," Cell, Mar. 8, 1996, vol. 84; pp. 769-779.
Jones et al., "Human Cytomegalovirus US2 Destabilizes Major Histocompatibility Complex Class I Heavy Chains," Journal of Virology, Apr. 1997, vol. 71, No. 4; pp. 2970-2979.
Machold et al., "The HCMV Gene Products US11 and US2 Differ in Their Ability to Attack Allelic Forms of Murine Major Histocompatibility Complex (MHC) Class I Heavy Chains," J Exp Med., Jan. 20, 1997, vol. 185, No. 2; pp. 363-366.
Tomazin et al., "Cytomegalovirus US2 destroys two components of the MHC class II pathway, preventing recognition by CD4+ T cells," Nature Medicine, Sep. 1999, vol. 5; pp. 1039-1043.

(Continued)

*Primary Examiner* — Rachel B Gill
(74) *Attorney, Agent, or Firm* — Carter, DeLuca & Farrell LLP; George Likourezos

(57) ABSTRACT

HCMV US11 based therapeutics that can be used to target and reduce the activity of the FcRn protein are provided. The compositions can be used in treatment of auto-immune mediated and albumin-mediated diseases in a subject HCMV US11, as well as for use in preventing, or treating, infections of HCMV through administration of a US11 inhibitor.

21 Claims, 30 Drawing Sheets

Specification includes a Sequence Listing.

(56) References Cited

OTHER PUBLICATIONS

Farrell et al., "Inhibition of natural killer cells by a cytomegalovirus MHC class I homologue in vivo," Nature, Apr. 1997, vol. 386; pp. 510-514.
Dunn et al., "Human Cytomegalovirus Glycoprotein UL 16 Causes Intracellular Sequestration of NKG2D Ligands, Protecting Against Natural Killer Cell Cytotoxicity," The Journal of Experimental Medicine, Jun. 2, 2003, vol. 197, No. 11; pp. 1427-1439.
Tomasec et al., "Downregulation of natural killer cell-activating ligand CD155 by human cytomegalovirus UL141," Nat Immunol., Feb. 2005, vol. 6, No. 2; pp. 181-188.
Chalupny, et al., "Down-regulation of the NKG2D ligand MICA by the human cytomegalovirus glycoprotein UL142," Biochem Biophys Res Commun., 2006, vol. 346; pp. 175-181.
Stern-Ginossar et al., "Host Immune System Gene Targeting by a Viral miRNA," Science. Jul. 20, 2007, vol. 317 (5836); pp. 376-381.
Kim et al., "Human Cytomegalovirus UL18 Utilizes US6 for Evading the NK and T-Cell Responses," PLoS Pathog., Aug. 2008, vol. 4, Issue 8; e1000123; 11 pages.
Nachmani et al., "Diverse Herpesvirus MicroRNAs Target the Stress-Induced Immune Ligand MICB to Escape Recognition by Natural Killer Cells," Cell Host Microbe, Apr. 23, 2009, vol. 5; pp. 376-385.
Prod'homme et al., "Human cytomegalovirus UL 141 promotes efficient downregulation of the natural killer cell activating ligand CD112," Journal of General Virology (2010), vol. 91; pp. 2034-2039.
Fielding et al., "Control of immune ligands by members of a cytomegalovirus gene expansion suppresses natural killer cell activation," eLIFE (2017), vol. 6, e22206, 27 pages.
Nimmerjahn et al., "Fcgamma receptors as regulators of immune responses," Nat Rev Immunol., Jan. 2008, vol. 8; pp. 34-47.
Klein et al., "Strain-Specific Neutralization of Human Cytomegalovirus Isolates by Human Sera," Journal of Virology, Feb. 1999; pp. 878-886.
Bowden et al., "Cytomegalovirus Immune Globulin and Seronegative Blood Products to Prevent Primary Cytomegalovirus Infection After Marrow Transplantation," The New England Journal of Medicine, Apr. 17, 1986; pp. 1006-1010.
Ross et al., "Cytomegalovirus (CmV) Reinfections in Healthy Seroimmune Women," J Infect Dis., Feb. 2010, vol. 201, No. 3; pp. 386-389.
Kropff et al., "Glycoprotein N of Human Cytomegalovirus Protects the Virus From Neutralizing Antibodies," PLoS Pathogens, Oct. 2012, vol. 8, Issue 10; e1002999; 15 pages.
Manley et al., "Human Cytomegalovirus Escapes a Naturally Occurring Neutralizing Antibody by Incorporating it into Assembling Virions," Cell Host & Microbe, Sep. 15, 2011, vol. 10; pp. 197-209.
Atalay et al., "Identification and Expression of Human Cytomegalovirus Transcription Units Coding for Two Distinct Fcgamma Receptor Homologs," Journal of Virology, Sep. 2002, vol. 76, No. 17; pp. 8596-8608.
Sprague et al, "The Human Cytomegalovirus Fc Receptor gp68 Binds the Fc CH2-CH3 Interface of Immunoglobulin G," Journal of Virology, Apr. 2008, vol. 82, No. 7; pp. 3490-3499.
Corrales-Aguilar et al., "Human Cytomegalovirus Fcγ Binding Proteins gp34 and gp68 Antagonize Fcγ Receptors I, II and III," PLoS Pathogens, May 2014, vol. 10, Issue 5; e1004131; 17 pages.
Simister et al., "An Fc receptor structurally related to MHC class I antigens," Nature, Jan. 1989, vol. 337; pp. 184-187.
Burmeister et al., "Crystal structure at 2.2 A resolution of the MHC-related neonatal Fc receptor," Nature, Nov. 24, 1994, vol. 372; pp. 336-343.
Zhu et al., "The heavy chain of neonatal Fc receptor for IgG is sequestered in endoplasmic reticulum by forming bligomers in the absence of beta2-microglobulin association," Biochem J., 2002; vol. 367; pp. 703-714.
Zeng et al., "Crystal Structure of Mouse CD1: An MHC-Like Fold with a Large Hydrophobic Binding Groove," Science, Jul. 18, 1997, vol. 277; pp. 339-345.
Raghavan et al., "The Class I Major Histocompatibility Complex Related Fc Receptor Shows pH-Dependent Stability Differences Correlating with Immunoglobulin Binding and Release," Biochemistry, 1993, vol. 32, pp. 8654-8660.
Roopenian et al., "FcRn: the neonatal Fc receptor comes of age," Nature Reviews | Immunology, Sep. 2007, vol. 7; pp. 715-725.
Dickinson et al., "Bidirectional FcRn-dependent IgG transport in a polarized human intestinal epithelial cell line," The Journal of Clinical Investigation, Oct. 1999, vol. 104, No. 7; pp. 903-911.
Spiekermann et al., "Receptor-mediated Immunoglobulin G Transport Across Mucosal Barriers in Adult Life: Functional Expression of FcRn in the Mammalian Lung," J Exp Med., Aug. 5, 2002, vol. 196, No. 3; pp. 303-310.
Li et al., "Transfer of IgG in the female genital tract by MHC class I-related neonatal Fc receptor (FcRn) confers protective immunity to vaginal infection," Proc Natl Acad Sci U S A. 2011; 108:4388-4393.
Kuo et al., "Neonatal Fc Receptor: From Immunity to Therapeutics," J Clin Immunol., 2010, vol. 30; pp. 777-789.
Ye et al., "Efficient mucosal Delivery of Vaccine Using the FcRn-Mediated IgG Transfer Pathway," Nat Biotechnol., Feb. 2011, vol. 29, No. 2; pp. 158-163.
Sockolosky et al., "The neonatal Fc receptor, FcRn, as a target for drug delivery and therapy," Adv Drug Deliv Rev., Aug. 30, 2015, vol. 91; pp. 109-124.
Maciejewski et al., "Infection of Hematopoietic Progenitor Cells by Human Cytomegalovirus," Blood, Jul. 1, 1992, vol. 80, No. 1; pp. 170-178.
Plachter et al., "Cell Types Involved in Replication and Distribution of Human Cytomegalovirus," Advances in Virus Research, 1996, vol. 46; pp. 195-261.
Maidji et al., "Developmental Regulation of Human Cytomegalovirus Receptors in Cytotrophoblasts Correlates with Distinct Replication Sites in the Placenta," Journal of Virology, May 2007, vol. 81, No. 9; pp. 4701-4712.
Firan et al., "The MHC class I-related receptor, FcRn, plays an essential role in the maternofetal transfer of gamma-globulin in humans," International Immunology, 2001, vol. 13, No. 8; pp. 993-1002.
Ward et al., "Evidence to support the cellular mechanism involved in serum lgG homeostasis in humans," International Immunology, 2003, vol. 15, No. 2; pp. 187-195.
Zhu et al., "MHC Class I-Related Neonatal Fc Receptor for IgG is Functionally Expressed in Monocytes, Intestinal Macrophages, and Dendritic Cells," J Immunol., 2001, vol. 166, No. 5; pp. 3266-3276.
Maidji et al., "Maternal Antibodies Enhance or Prevent Cytomegalovirus Infection in the Placenta by Neonatal Fc Receptor-Mediated Transcytosis," American Journal of Pathology, Apr. 2006, vol. 168, No. 4; pp. 1210-1226.
Ye et al., "The MHC Class II-Associated Invariant Chain Interacts with the Neonatal Fc Gamma Receptor and Modulates its Trafficking to Endosomal/Lysosomal Compartments," J Immunol., Aug. 15, 2008, vol. 181, No. 4; pp. 2572-2585.
Zhu et al., "Calnexin and ERp57 Facilitate the Assembly of the Neonatal Fc Receptor for IgG with beta 2-Microglobulin in the Endoplasmic Reticulum," The Journal of Immunology, 2005, vol. 175; pp. 967-976.
Story et al., "A Major Histocompatibility Complex Class I-like Fc Receptor Cloned From Human Placenta: Possible Role in Transfer of Immunoglobulin G From Mother to Fetus," J Exp Med., Dec. 1994, vol. 180; pp. 2377-2381.
Ye et al., "A membrane protein complex mediates retro-translocation from the ER lumen into the cytosol," Nature. 2004, vol. 429; pp. 841-847.
Lilley et al., "A membrane protein required for dislocation of misfolded proteins from the ER," Nature. 2004; vol. 429; pp. 834-840.
Mehnert et al., "Der1 promotes movement of misfolded proteins through the endoplasmic reticulum membrane," Nature Cell Biology, 2014, vol. 16; pp. 77-86.

(56) References Cited

OTHER PUBLICATIONS

Lilley et al., "Dislocation of a Type I Membrane Protein Requires Interactions Between Membrane-Spanning Segments within the Lipid Bilayer," Sep. 2003, vol. 14; pp. 3690-3698.

Van den Boomen et al., "TMEM129 is a Derlin-1 associated ERAD E3 ligase essential for virus-induced degradation of MHC-I.," Proc Natl Acad Sci U S A. (PNAS), Aug. 5, 2014, vol. 111, No. 31; pp. 11425-11430.

Van de Weijer et al., "A high-coverage shRNA screen identifies TMEM129 as an E3 ligase involved in ER-associated protein degradation," Nature Communications, 2014, vol. 5; pp. 1-14.

Von Heijne, "Control of topology and mode of assembly of a polytopic membrane protein by positively charged residues," Nature, Oct. 5, 1989, vol. 341; pp. 456-458.

Kostova et al., "Ubiquitin Ligases, Critical Mediators of Endoplasmic Reticulum-Associated Degradation," Semin Cell Dev Biol., 2007, vol. 18, No. 6; pp. 770-779.

Esclatine et al., "Human Cytomegalovirus Infects Caco-2 Intestinal Epithelial Cells Basolaterally Regardless of the Differentiation State," Journal of Virology, Jan. 2000, vol. 74, No. 1; pp. 513-517.

Ward et al., "Multitasking by Exploitation of Intracellular Transport Functions the Many Faces of FcRn," Adv Immunol., 2009; vol. 103; pp. 77-115.

Ober et al., "Visualizing the Site and Dynamics of IgG Salvage by the MHC Class I-Related Receptor, FcRn," The Journal of Immunology, Mar. 2004, vol. 172; pp. 2021-2029.

Tesar et al., "Ligand Valency Affects Transcytosis, Recycling and Intracellular Trafficking Mediated by the Neonatal Fc Receptor," Traffic, 2006, vol. 7; pp. 1127-1142.

Hegde et al., "Quality and Quantity Control at the Endoplasmic Reticulum," Curr Opin Cell Biol. , Aug. 2010, vol. 22, No. 4; pp. 437-446.

Guerriero et al., "The Delicate Balance Between Secreted Protein Folding and Endoplasmic Reticulum-Associated Degradation in Human Physiology," Physiol Rev, Apr. 2012, vol. 92, No. 2; pp. 537-576.

Olzmann et al., "The Mammalian Endoplasmic Reticulum-Associated Degradation System," Cold Spring Harb Perspect Biol., 2013; vol. 5. a013185, 17 pages.

Randow et al., "Viral avoidance and exploitation of the ubiquitin system," Nature Cell Biology, May 2009, vol. 11, No. 5; pp. 527-534.

Isaacson et al., "Ubiquitination, ubiquitin-like modifiers, and deubiquitination in viral infection," Cell Host Microbe, 2009, vol. 5; pp. 559-570.

Lee et al., "Functional dissection of HCMV US11 in mediating the degradation of MHC class I molecules," Biochemical and Biophysical Research Communications, 2005, vol. 330; pp. 1262-1267.

Hamprecht et al., "Cytomegalovirus transmission to preterm infants during lactation," J Clin Virol., 2008, vol. 41; pp. 198-205.

Greenblatt et al., "Derlin-1 is a rhomboid pseudoprotease required for the dislocation of mutant alpha-1 antitrypsin from the endoplasmic reticulum," Nat Struct Mol Biol., 2011, vol. 18, No. 10; pp. 1147-1152.

Ye et al., "The AAA ATPase Cdc48/p97 and its partners transport proteins from the ER into the cytosol.," Nature. 2001, vol. 414; pp. 652-656.

Loureiro et al., "Antigen presentation and the ubiquitin-proteasome system in host-pathogen interactions," Adv Immunol., 2006, vol. 92; pp. 225-305.

Barel et al., "Amino acid composition of alpha1/alpha2 domains and cytoplasmic tail of MHC class I molecules determine their susceptibility to human cytomegalovirus US11-mediated down-regulation," Eur J Immunol., 2003, vol. 33; pp. 1707-1716.

Cho et al., "The C-Terminal Amino Acid of the MHC-I Heavy Chain is Critical for Binding to Derlin-1 in Human Cytomegalovirus US11-Induced MHC-I Degradation," PLoS One, Aug. 2013, vol. 8, Issue 8, e72356; 14 pages.

Chevalier et al., "Binding of Human Cytomegalovirus US2 to Major Histocompatibility Complex Class I and II Proteins is not Sufficient for Their Degradation," Journal of Virology, Aug. 2002, vol. 76, No. 16; pp. 8265-8275.

Cadwell et al., "Ubiquitination on Nonlysine Residues by a Viral E3 Ubiquitin Ligase," Science, Jul. 1, 2005, vol. 309; pp. 127-130.

Wang et al., "The Viral E3 Ubiquitin Ligase mK3 Uses the Derlin/p97 Endoplasmic Reticulum-Associated Degradation Pathway to Mediate Down-Regulation of Major Histocompatibility Complex Class I proteins," The Journal of Biological Chemistry, Mar. 31, 2006, vol. 281, No. 13; pp. 8636-8344.

Hassink et al., "Ubiquitination of MHC Class I Heavy Chains is Essential for Dislocation by Human Cytomegalovirus—encoded US2 but not US11," The Journal of Biological Chemistry, Oct. 6, 2006, vol. 281, No. 40; pp. 30063-30071.

Hansen et al., "Cytomegalovirus Vectors Violate CD8+ T Cell Epitope Recognition Paradigms," Science, May 24, 2013, vol. 340, No. 6135; 1237874; 34 pages.

Akilesh et al., "The MHC class I-like Fc receptor promotes humorally mediated autoimmune disease," The Journal of Clinical Investigation, May 2004, vol. 113, No. 9; pp. 1328-1333.

Burr et al., "HRD1 and UBE2J1 target misfolded MHC class I heavy chains for endoplasmic reticulum-associated degradation," Proc Natl Acad Sci U S A. (PNAS), Feb. 1, 2011, vol. 108, No. 5; pp. 2034-2039.

Bai et al., "Intracellular neutralization of viral infection in polarized epithelial cells by neonatal Fc receptor (FcRn)-mediated IgG transport," Proc Natl Acad Sci U S A. (PNAS), Nov. 8, 2011, vol. 108, No. 45; pp. 18406-18411.

Grevys et al., "A human endothelial cell-based recycling assay for screening of FcRn targeted molecules," Nature Communications, 2018, vol. 9; 621; 14 pages.

Liu et al., "Amelioration of Experimental Autoimmune Myasthenia Gravis in Rats by Neonatal FcR Blockade," The Journal of Immunology, 2007, vol. 178; pp. 5390-5398.

Ward et al., "Targeting FcRn for therapy: From live cell imaging to in vivo studies in mice," Immunology Letters, 2014, vol. 160; pp. 158-162.

Masuda et al., "Role of Fc Receptors as a Therapeutic Target," Inflammation & Allergy—Drug Targets, 2009, vol. 8; pp. 80-86.

Li et al., "Complete FcRn dependence for intravenous Ig therapy in autoimmune skin blistering diseases," J. Clin Invest., 2005, vol. 115, No. 12; pp. 3440-3450.

Sesarman et al., "Neonatal Fc receptor deficiency protects from tissue injury in experimental epidermolysis bullosa acquisita," J. Mol. Med., 2008, vol. 86; pp. 951-959.

Sesarman et al., "The neonatal Fc receptor as therapeutic target in lgG-mediated autoimmune diseases," Cellular and Molecular Life Sciences, 2010, vol. 67; pp. 2533-2550.

Blumberg et al., "Blocking FcRn in humans reduces circulating IgG levels and inhibits IgG immune complex-mediated immune responses," Science Advances, Dec. 18, 2019, vol. 5, e-aax9586; 12 pages.

Jacob, Christian L., et al., "Neutralizing antibodies are unable to inhibit direct viral cell-to-cell spread of human cytomegalovirus," Virology 444(1-2), Sep. 2013, pp. 140-147.

Jones, Thomas R., et al., "Replacement mutagenesis of the human cytomegalovirus genome: US10 and US11 gene products are non-essential," Journal of virology, Nov. 1991, vol. 65, No. 11, pp. 5860-5872.

Hansen, Scott G., et al., "Cytomegalovirus Vectors Violate CD8+ T Cell Epitope Recognition Paradigms," Science, May 2013, vol. 340(6135): 1237874, 19 pages.

Liu, Xiaoyang, et al., "Human cytomegalovirus evades antibody-mediated immunity through endoplasmic reticulum-associated degradation of the FcRn receptor," Nature communications, Jul. 2019, vol. 10(1), pp. 1-19.

Murray, Susan E., et al., "Fibroblast-adapted human CMV vaccines elicit predominantly conventional CD8 T cell responses in humans.," Journal of Experimental Medicine, Jul. 2017, vol. 214(7), pp. 1889-1899.

Basta, Sameh, et al., "Inhibitory effects of cytomegalovirus proteins US2 and US11 point to contributions from direct priming and

(56) References Cited

OTHER PUBLICATIONS cross-priming in induction of vaccinia virus-specific CD8+ T cells," The Journal of Immunology, Jun. 2002, vol. 168(11), pp. 5403-5408.
Elkington, Rebecca, et al., "Ex vivo profiling of CD8+-T-cell responses to human cytomegalovirus reveals broad and multispecific reactivities in healthy virus carriers," Journal of virology, May 2003, vol. 77(9), pp. 5226-5240.
Schempp, Susanne, et al., "Deletion mutant of human cytomegalovirus lacking US2-US6 and US11 maintains MHC class I expression and antigen presentation by infected dendritic cells," Virus research, Feb. 2011, vol. 155(2), pp. 446-454.
Cui, Xiaohong, et al., "Bacterial artificial chromosome clones of viruses comprising the Towne cytomegalovirus vaccine," Journal of Biomedicine and Biotechnology 2012, Oct. 2012, 8 pages.

\* cited by examiner

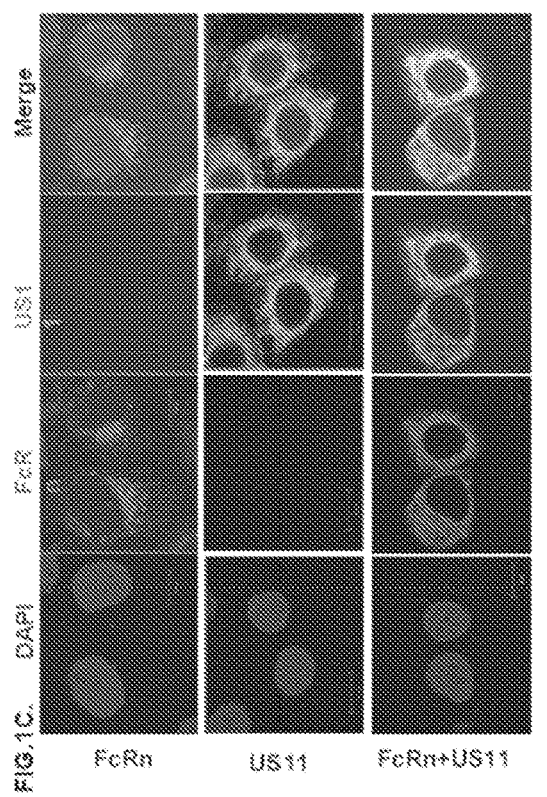
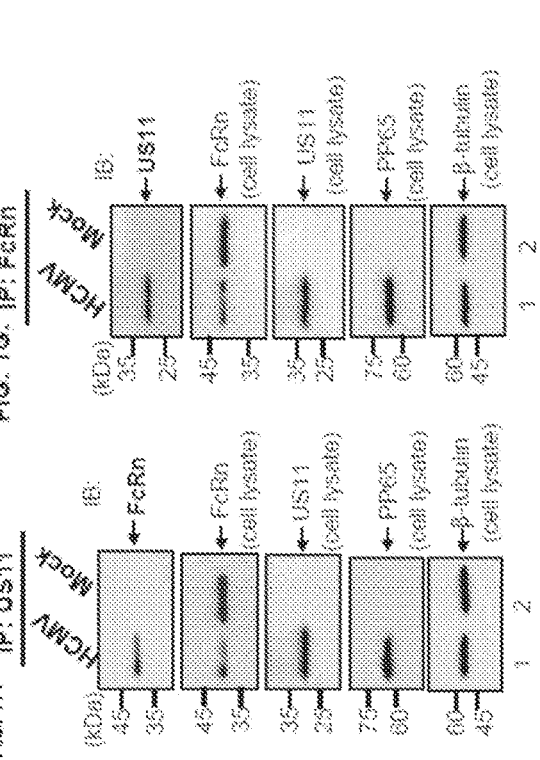
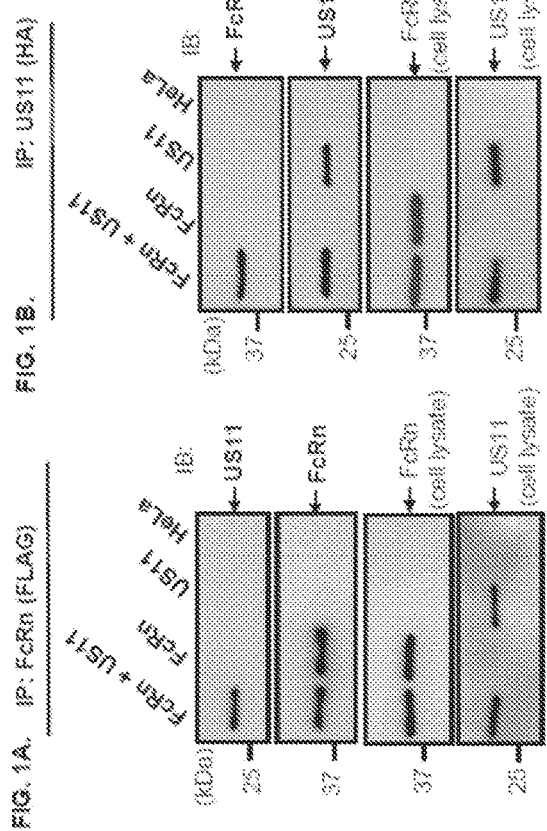
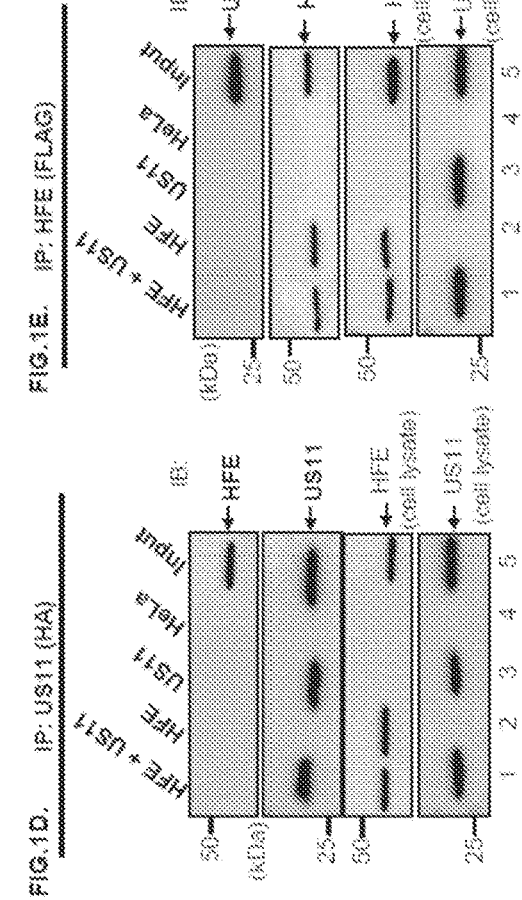

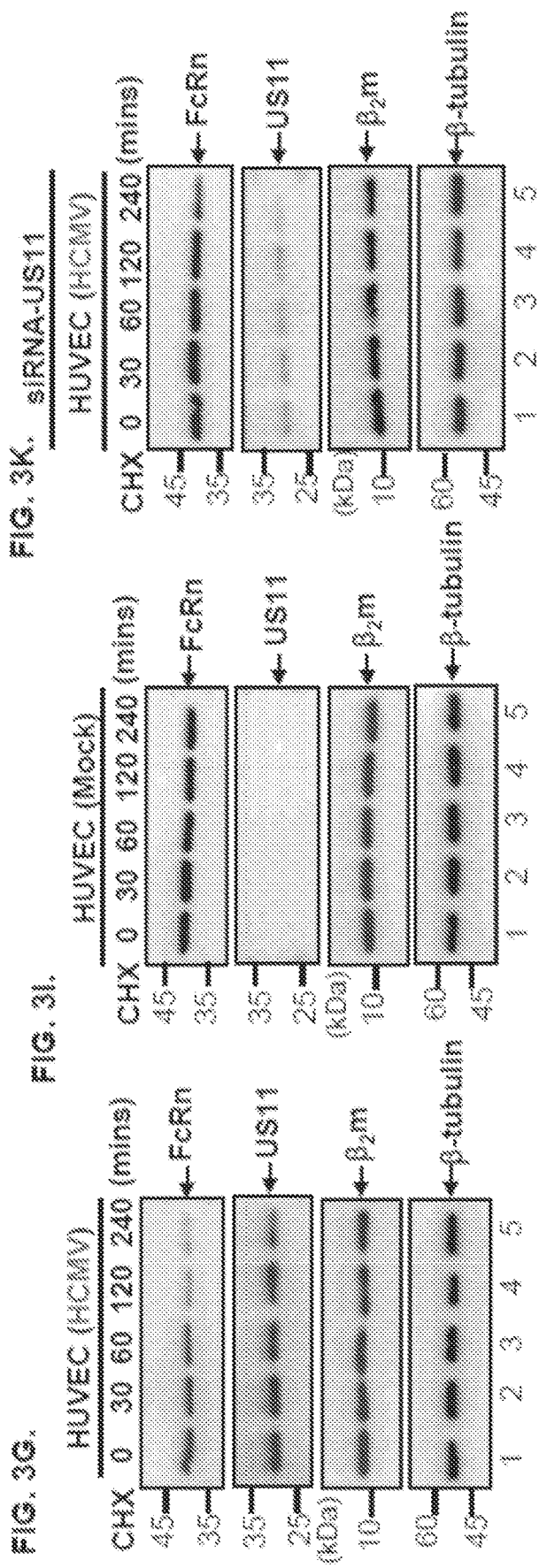
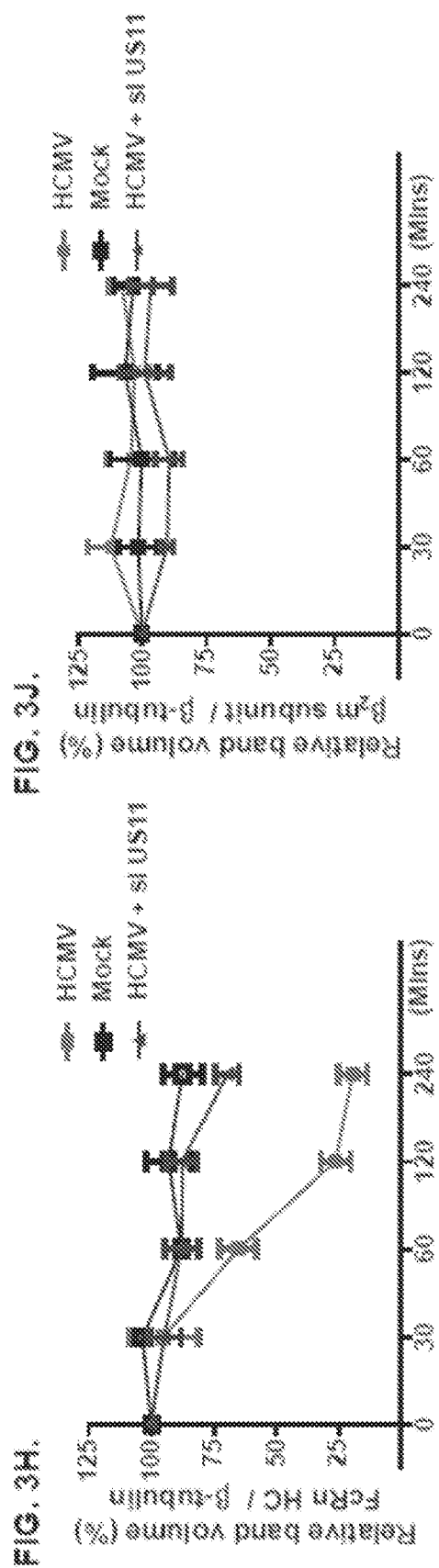

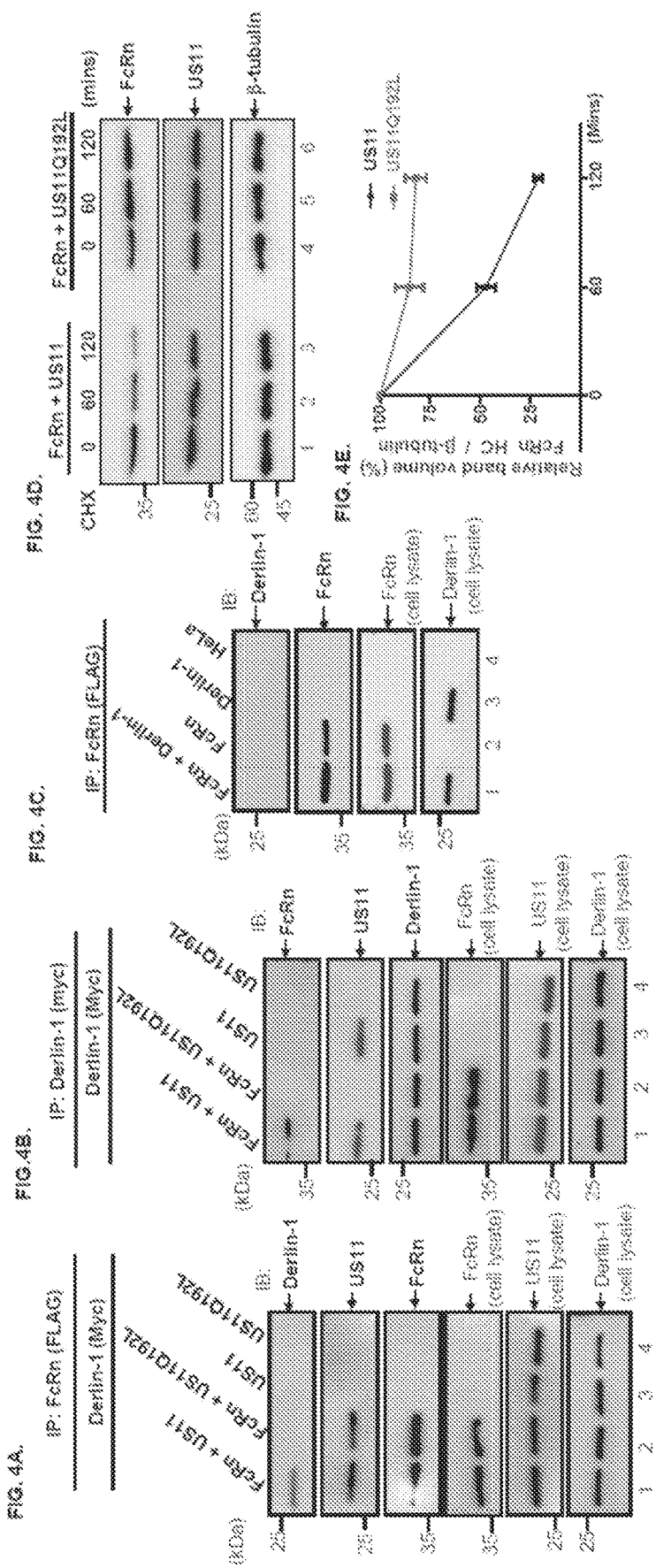

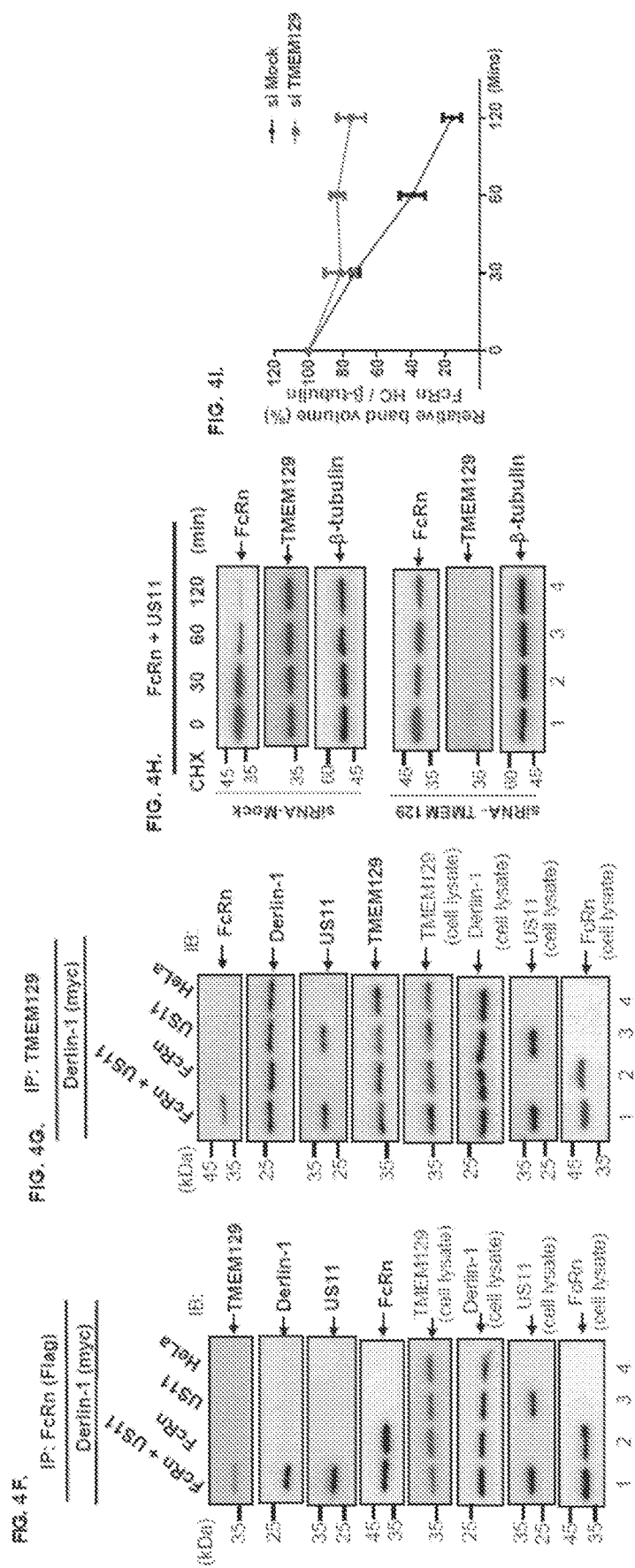

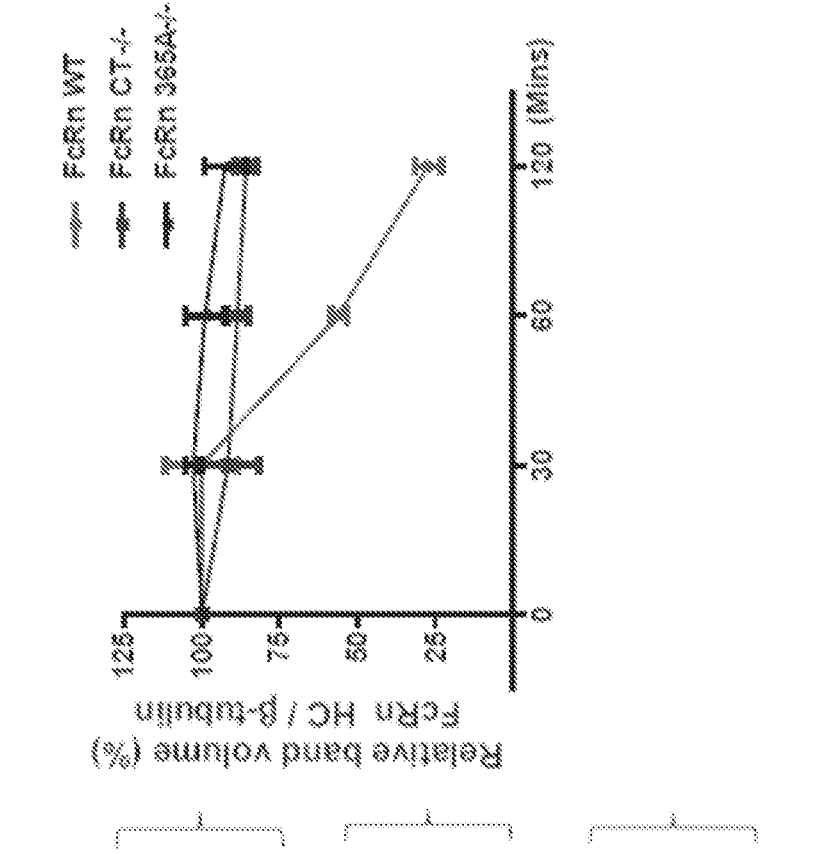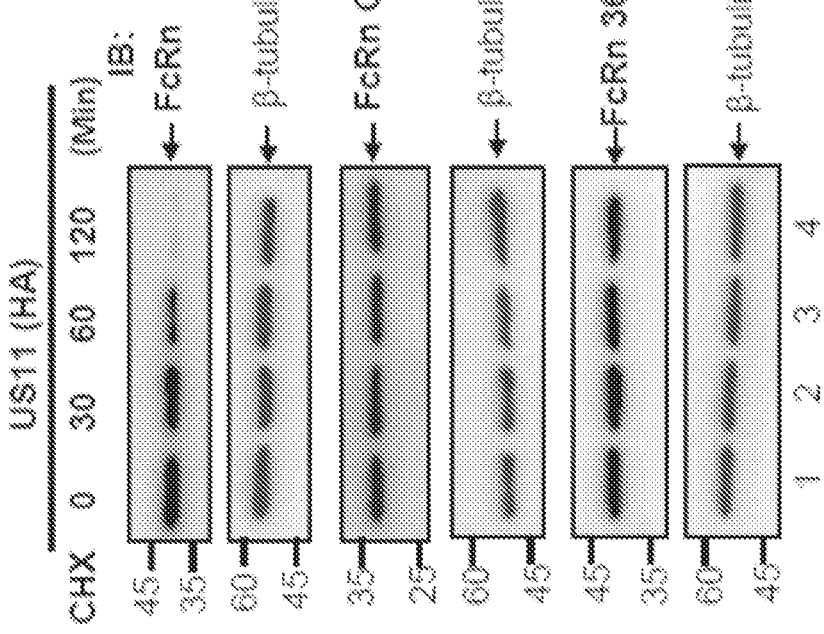

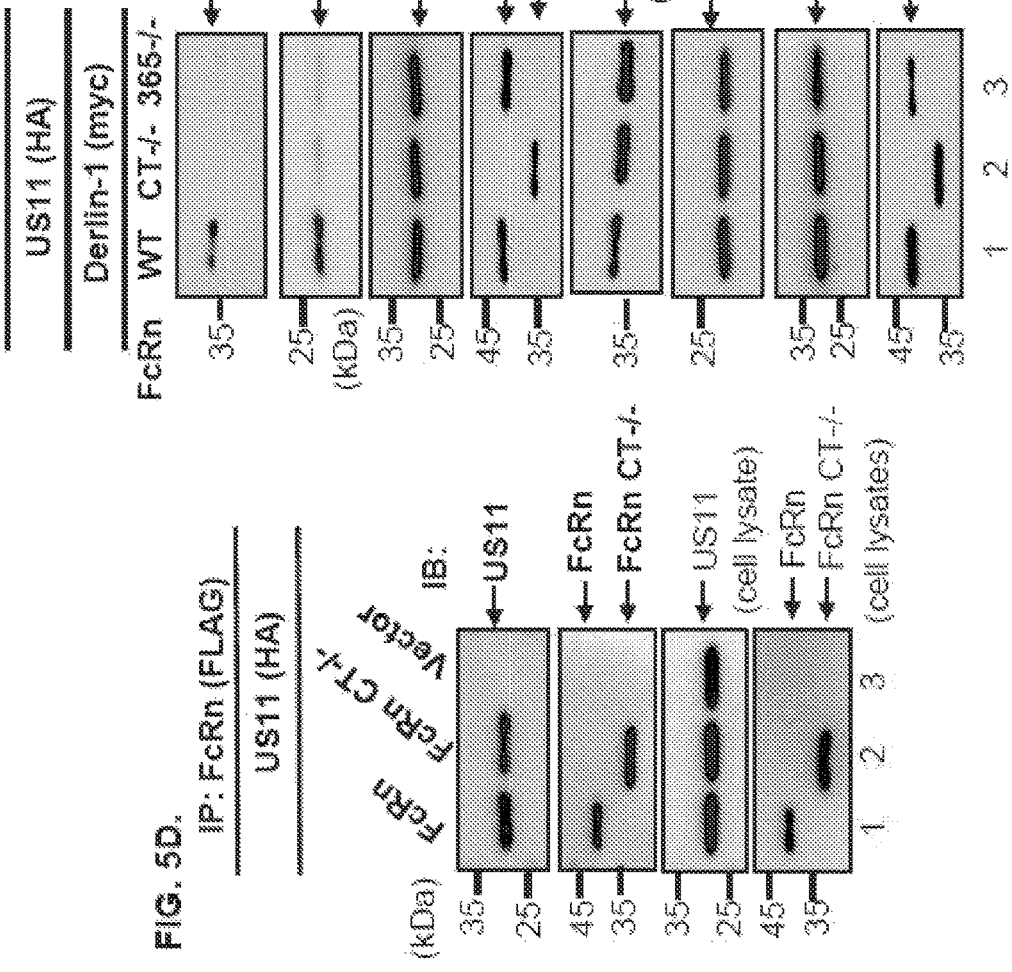
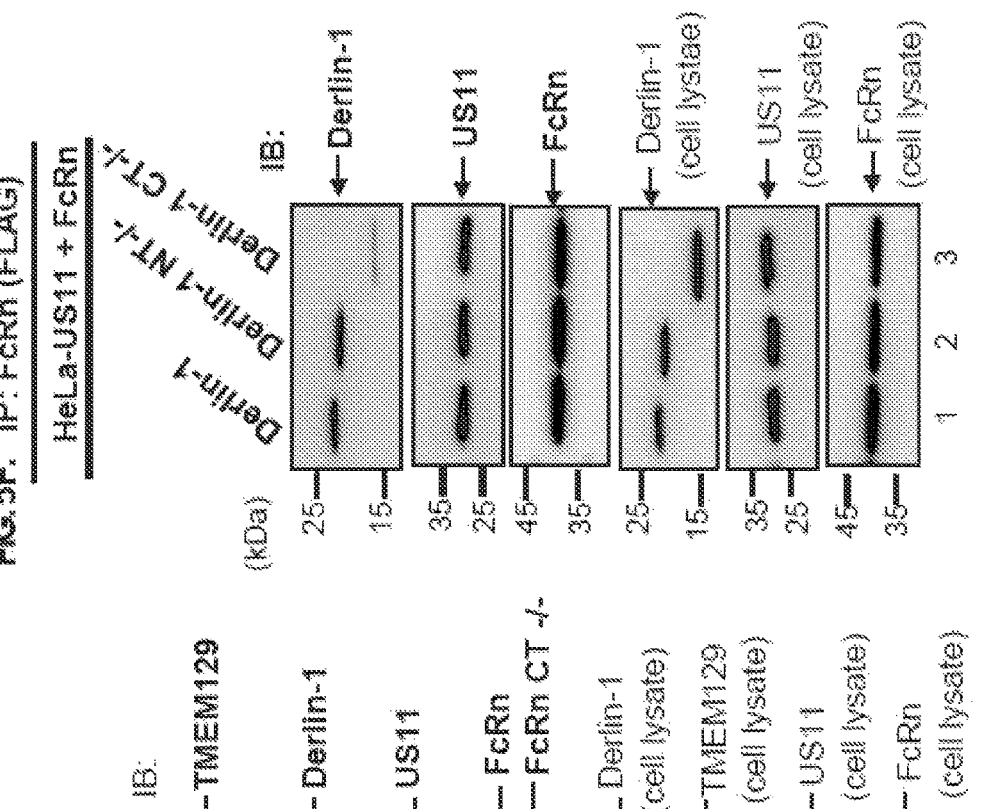
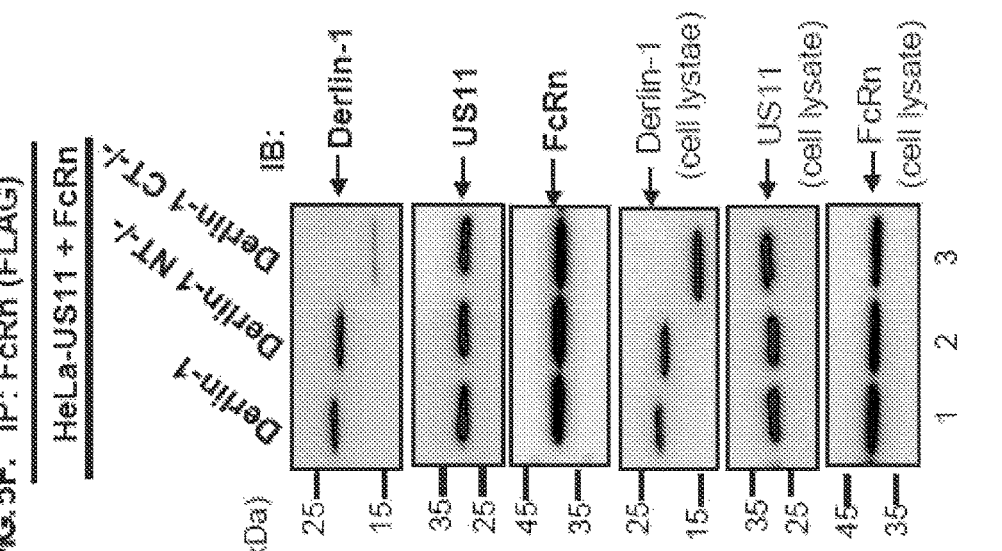

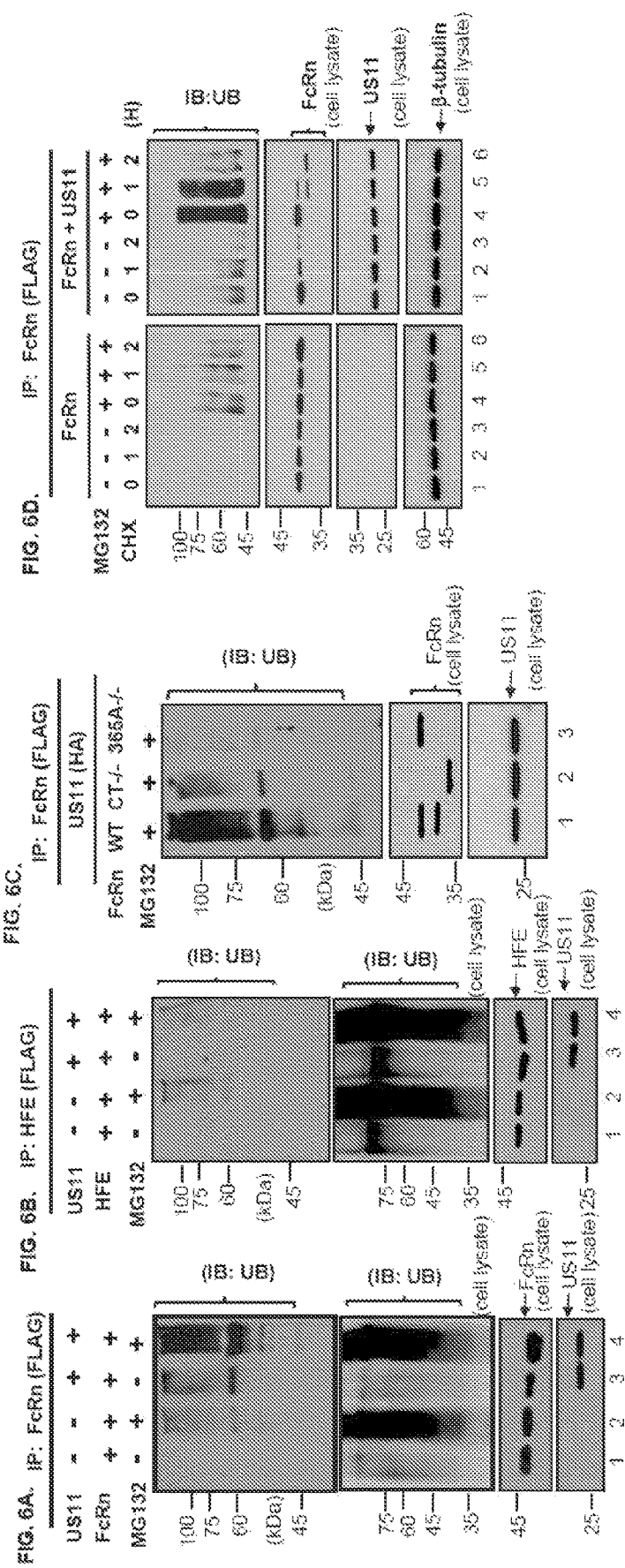

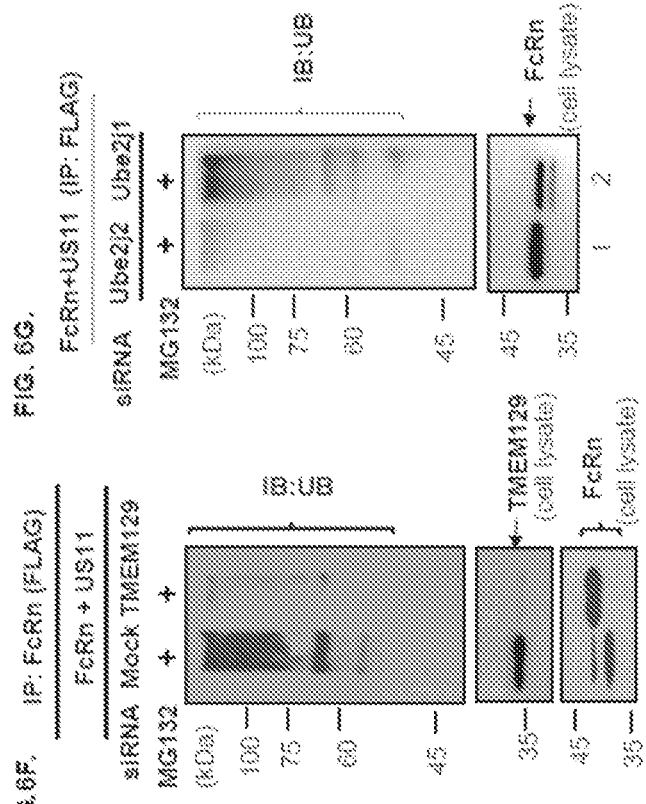
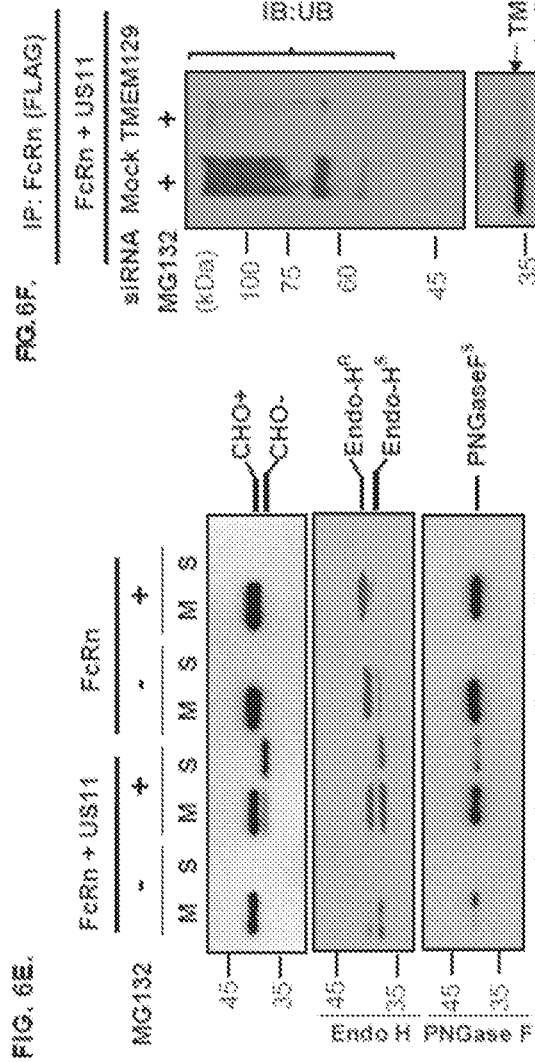
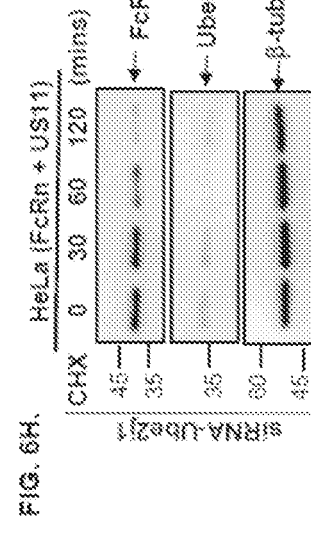
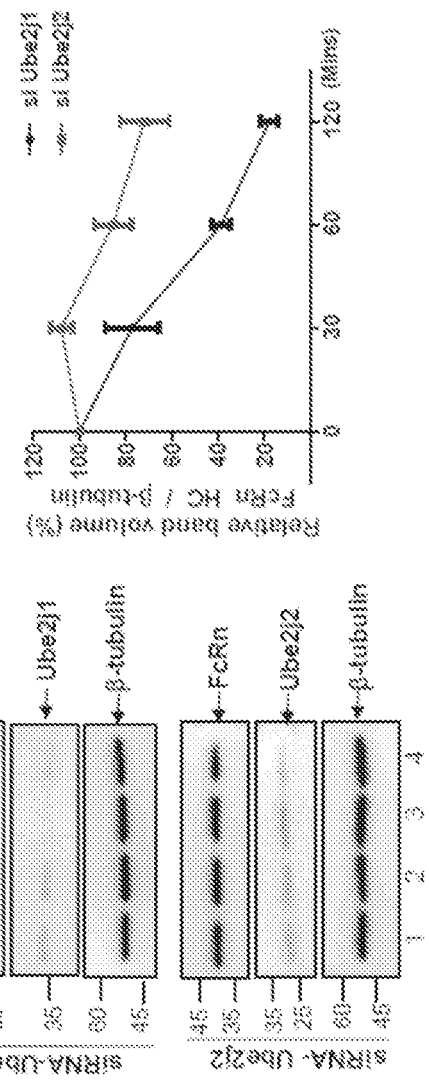

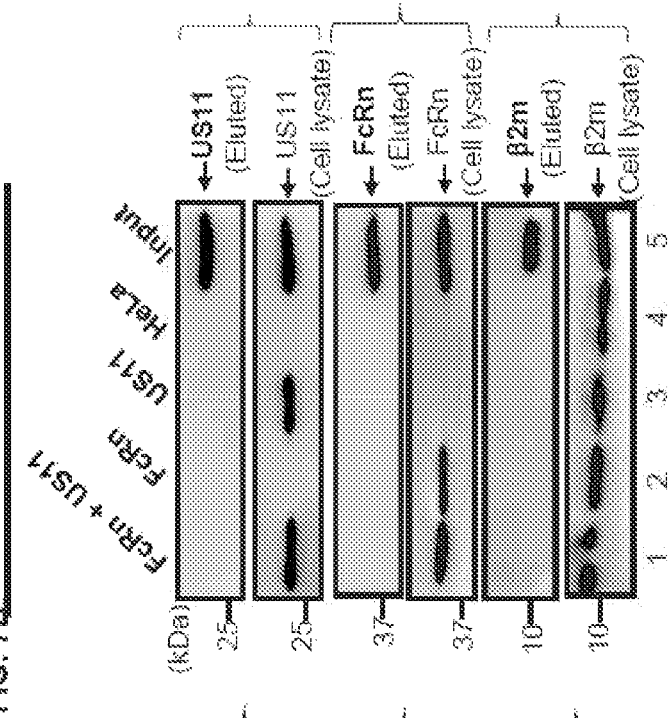
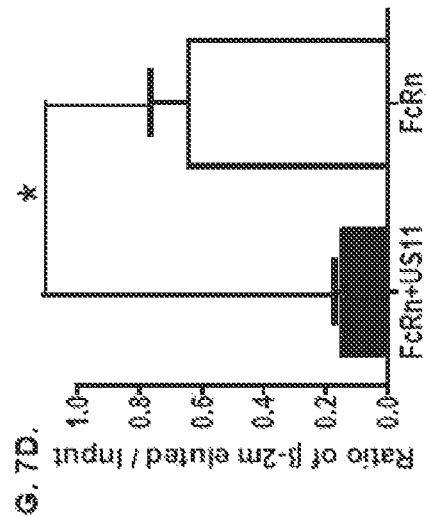
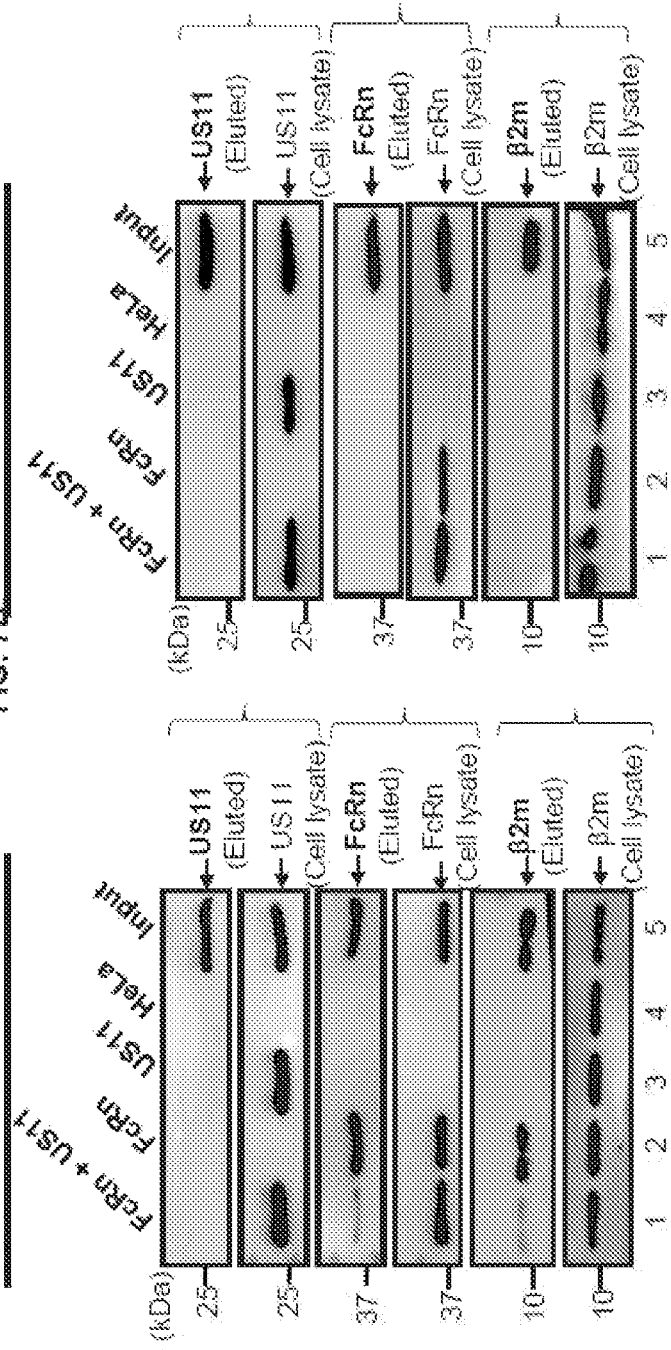
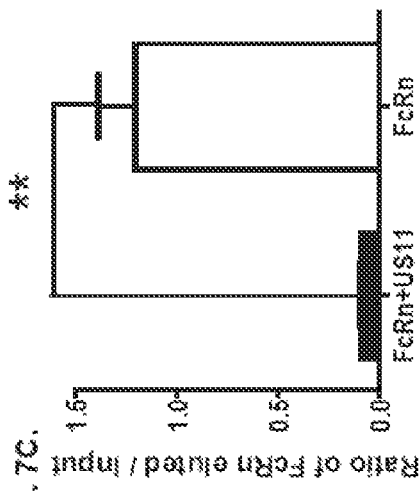

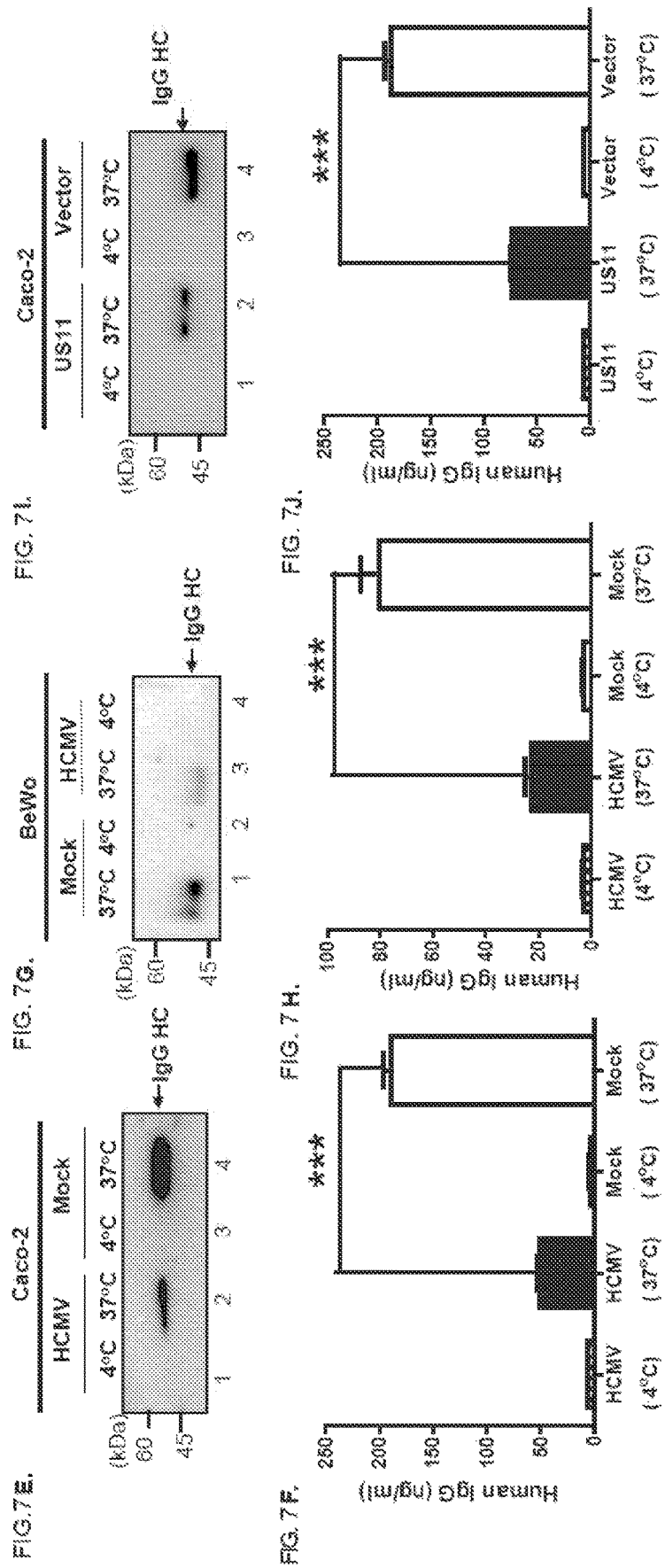

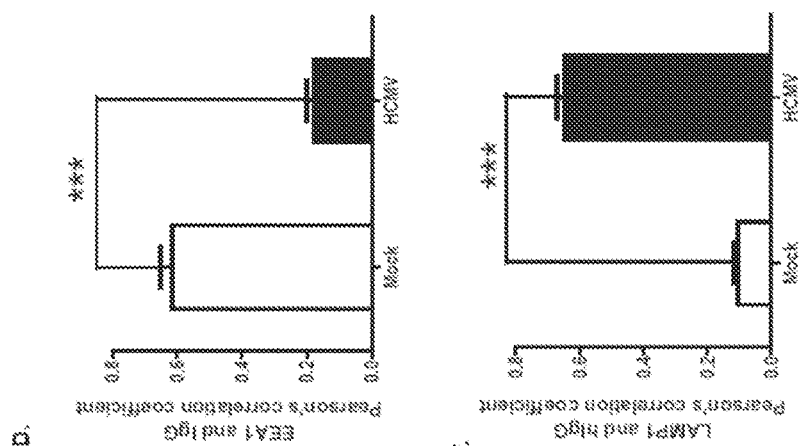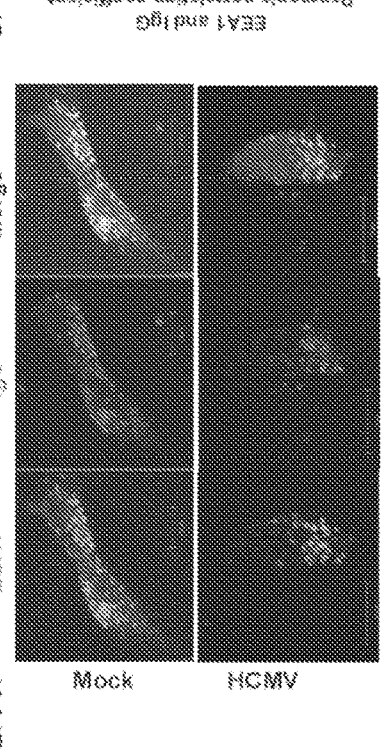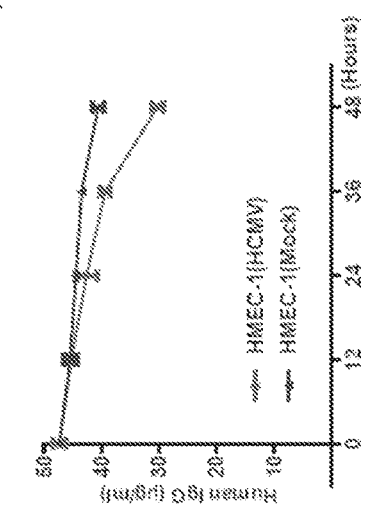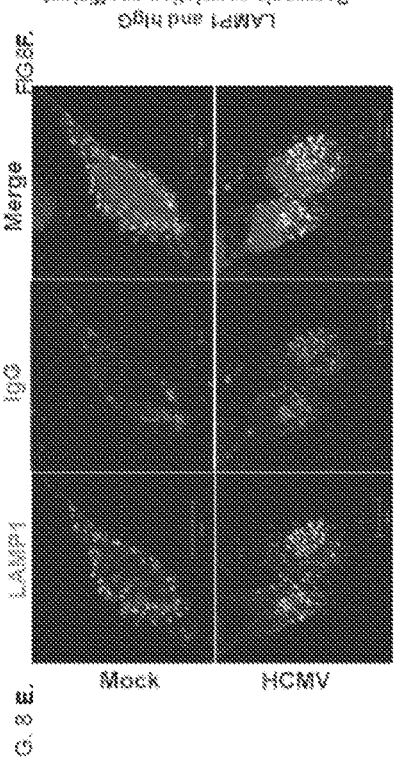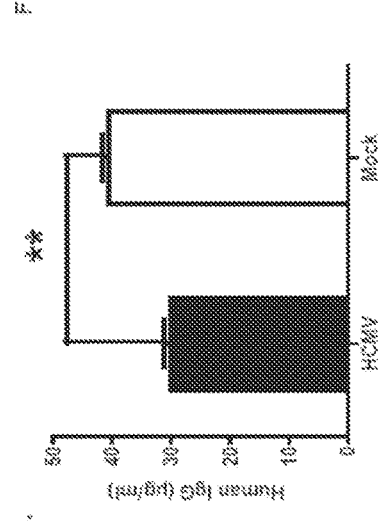

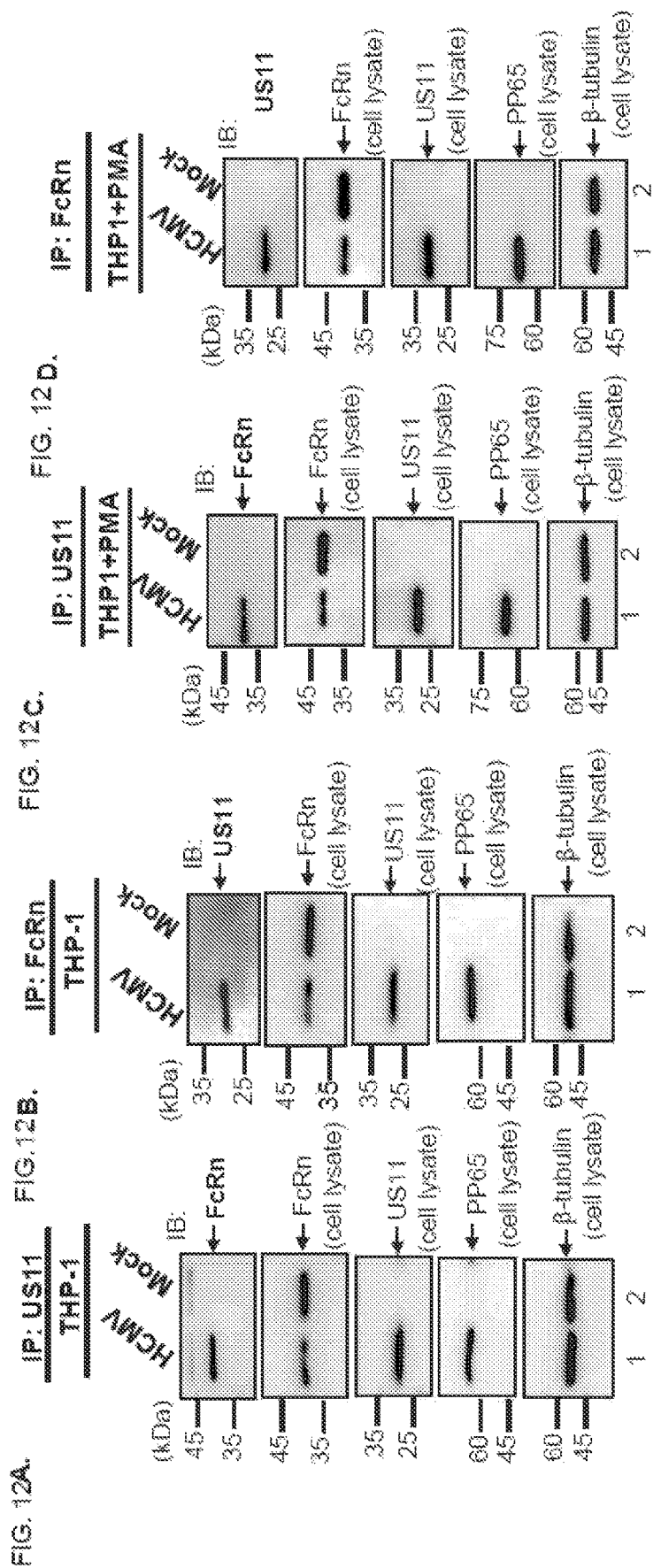

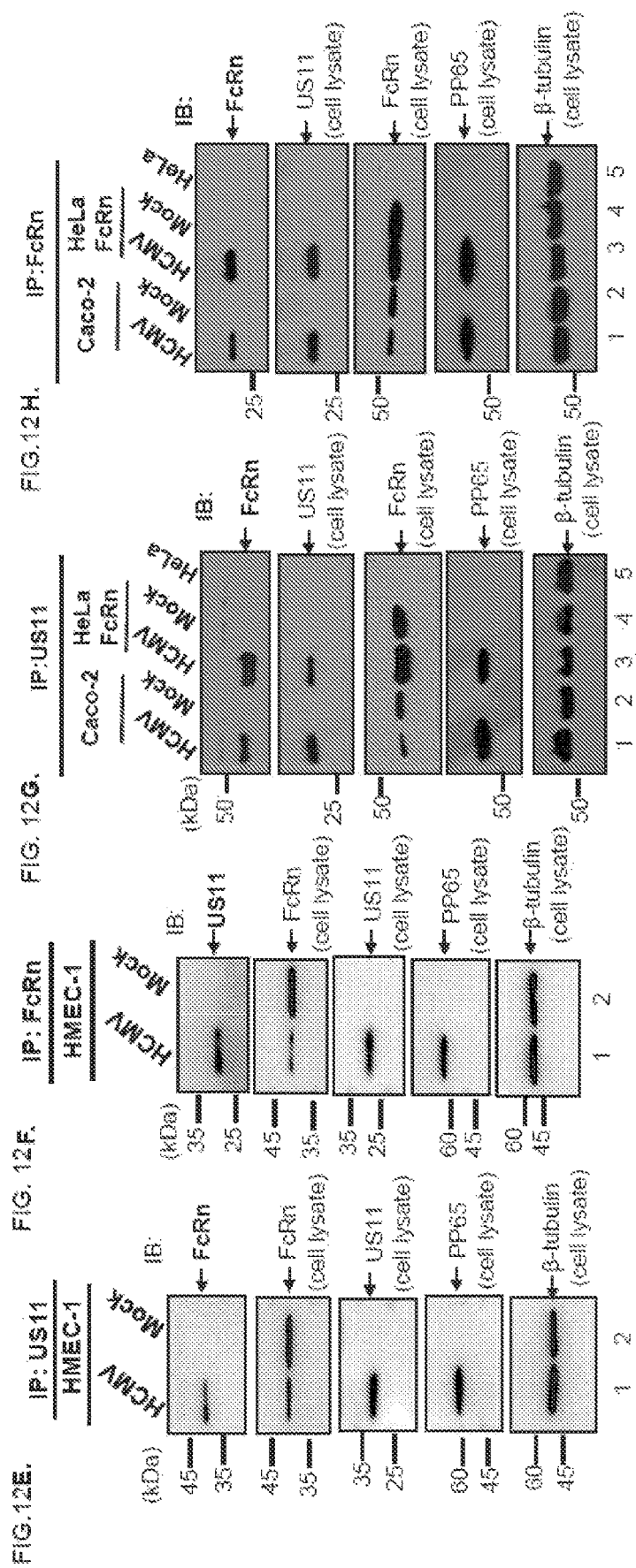

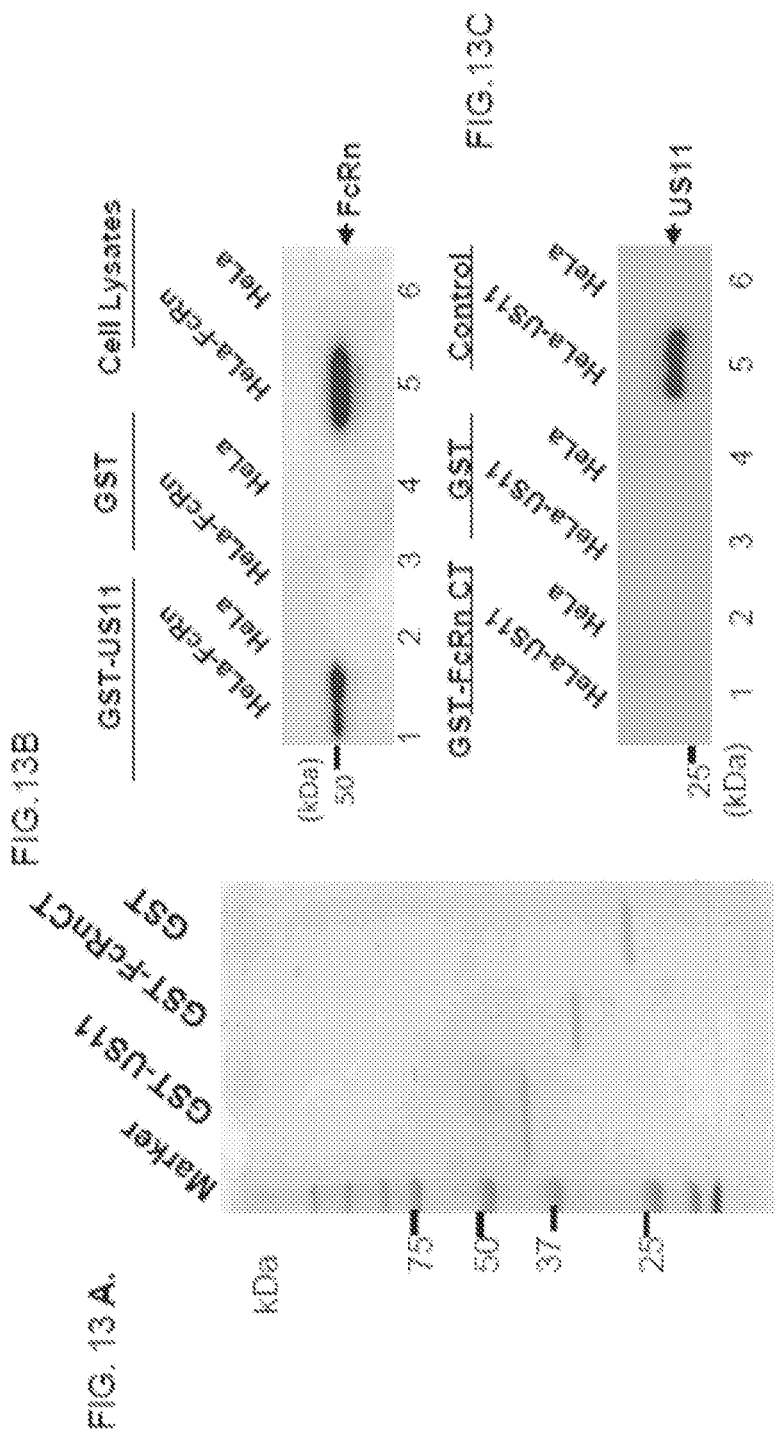

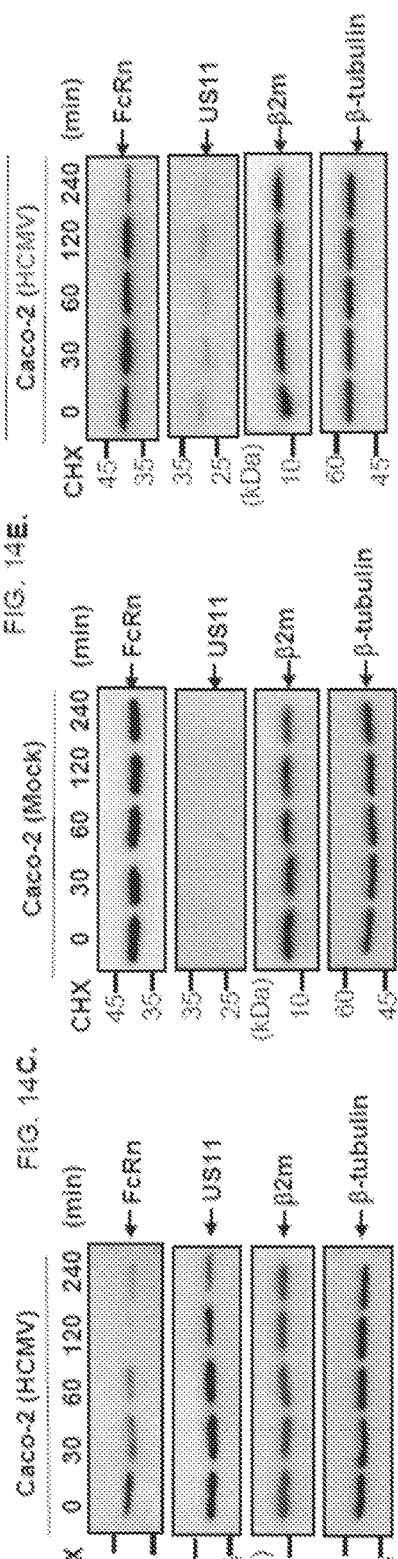

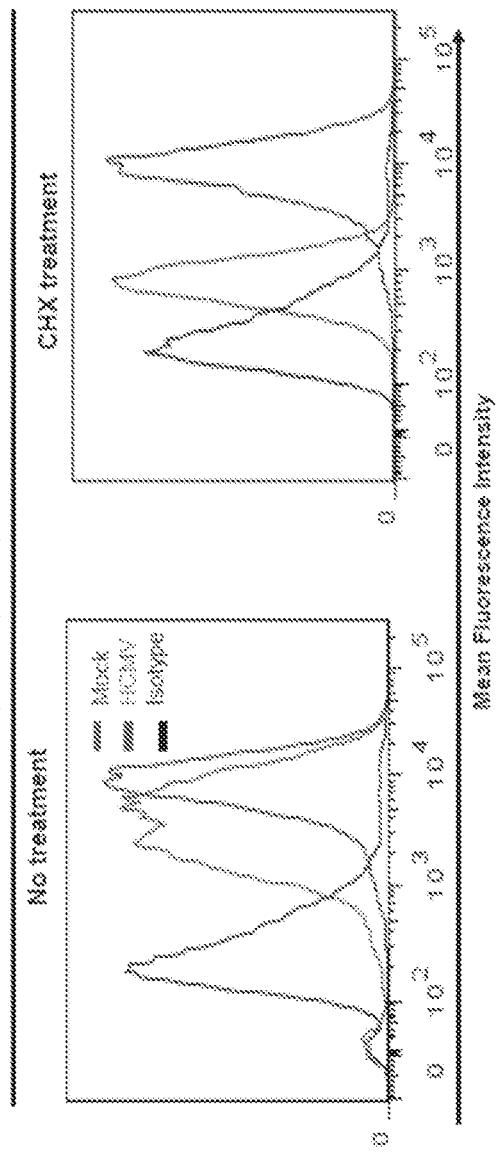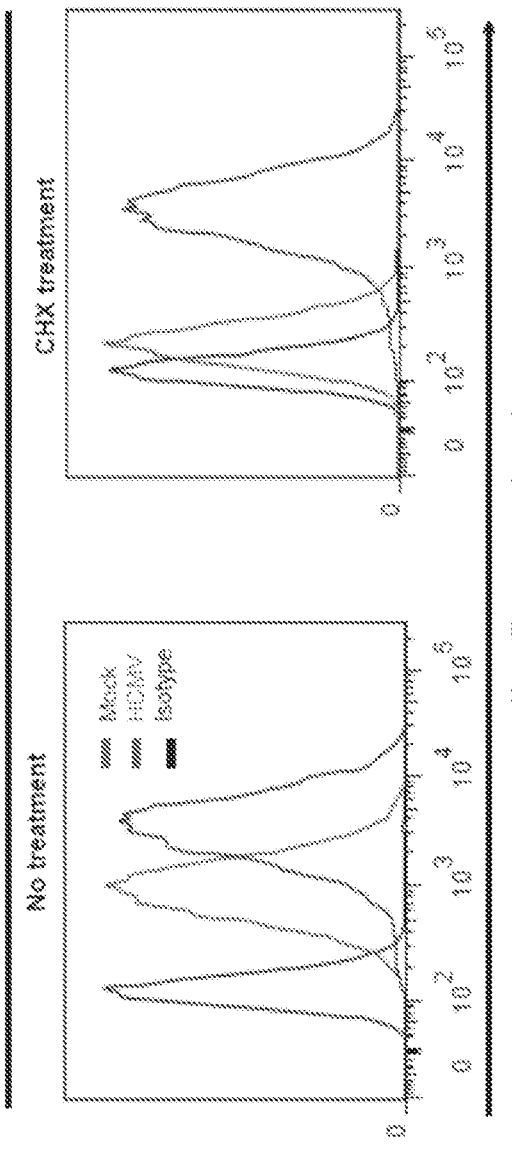
FIG. 15A.
FIG. 15B.

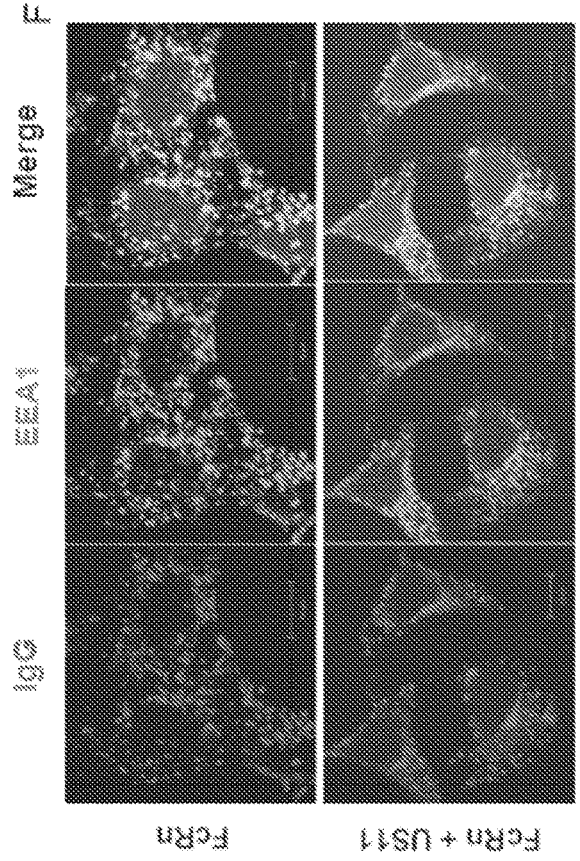
FIG. 18A.
FIG. 18B.
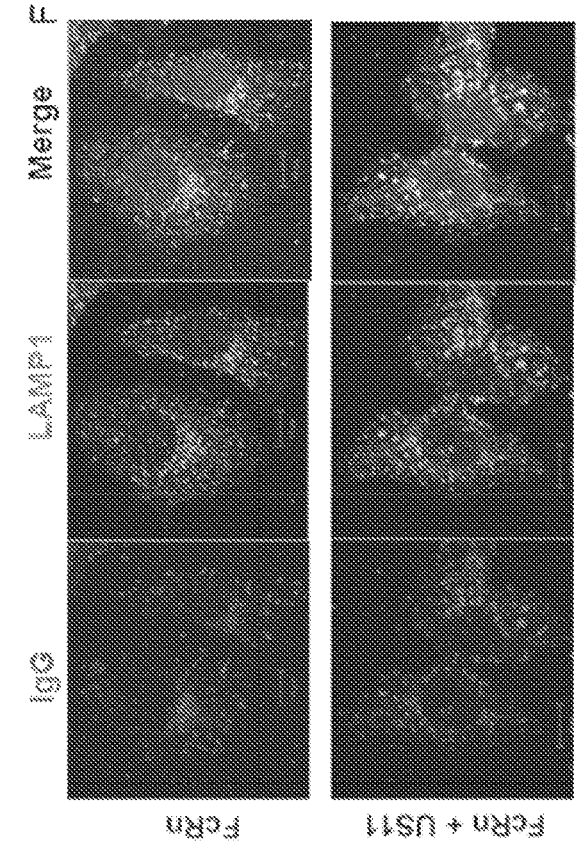
FIG. 18C.
FIG. 18D.

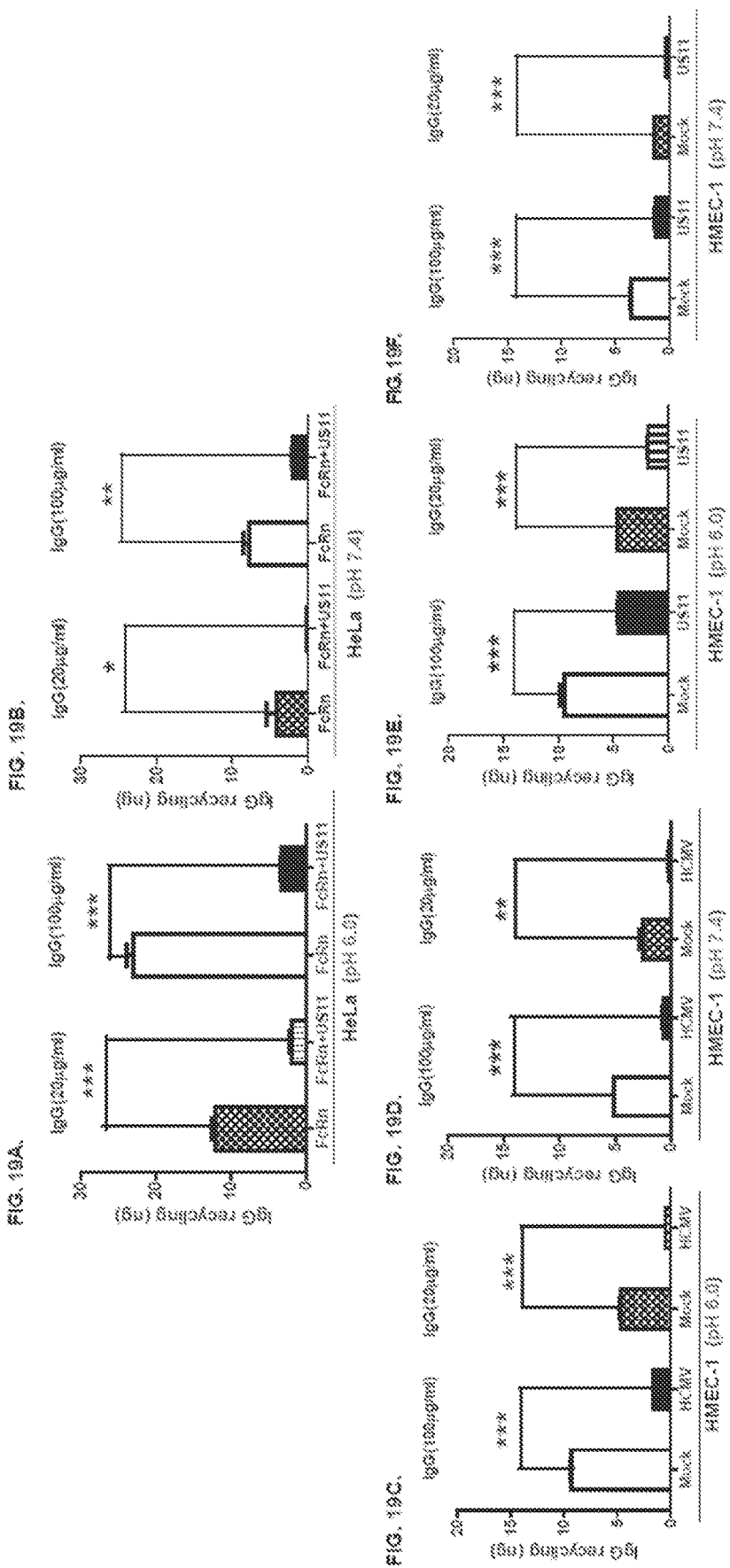

FcRn-TARGETED THERAPEUTICS FOR THE TREATMENT OF ANTIBODY-MEDIATED AUTOIMMUNE AND ALBUMIN-MEDIATED DISEASE

This application claims the benefit of U.S. application Ser. No. 16/799,605, filed Feb. 24, 2020, which claims priority to provisional application Ser. No. 62/809,284, filed Feb. 22, 2019, and provisional application Ser. No. 62/853,995 filed May 29, 2019, the entire contents of which are incorporated herein.

GOVERNMENT SUPPORT STATEMENT

This invention was made with government support under AI130712A awarded by the National Institutes of Health. The government has certain rights in the invention.

REFERENCE TO SEQUENCE LISTING

This application includes an electronically submitted sequence listing in .XLM format. The .XLM file contains a sequence listing entitled "1475-62.xml" created on Dec. 20, 2022 and is 16,005 bytes in size. The sequence listing contained in this .xlm file is part of the specification and is hereby incorporated by reference herein in its entirety.

TECHNICAL FIELD

The present disclosure is drawn to HCMV US11 based therapeutics that can be used to target and reduce the activity of the FcRn protein. The disclosure provides a method of treating auto-immune mediated and albumin-mediated diseases in a subject comprising administering to the subject a therapeutically effective amount of a pharmaceutical composition comprising HCMV US11 (herein after referred to as "US11") polypeptide, polypeptide fragments, or variants thereof. The disclosure also provides methods for preventing, or treating, infections of HCMV through administration of a US11 inhibitor. US11 containing vaccine compositions are also provided for stimulation of an anti-US11 immune response for protection against HCMV infection.

BACKGROUND

Human cytomegalovirus (HCMV) is a herpesvirus that infects humans throughout the world. While most infections with HCMV are asymptomatic, the virus can cause infectious mononucleosis. In either case the virus progresses to latency and infected persons become lifelong infectious carriers. However, both initial and reactivated HCMV infections pose a life-threatening risk in immunocompromised patients, such as transplant recipients and patients with uncontrolled HIV infection. In addition, due to its ability to infect the developing fetus in utero via placental transmission, HCMV is the leading infectious cause of congenital abnormalities worldwide (1).

HCMV has been successful in infecting humans due to its ability to evade the immune system and establish lifelong latency and persistent virus shedding. Viral infections are normally controlled through Ab-mediated and cell-mediated immunity; the latter involves CD4$^+$ and CD8$^+$ T lymphocytes and natural killer (NK) cells. Cell-mediated immunity is essential for limiting HCMV disease (2), and individuals with genetic defects affecting cell-mediated immunity are highly susceptible to severe HCMV disease (3, 4). HCMV expresses the US6 protein that inhibits T-cell activation by blocking TAP-dependent anterograde peptide transport to the endoplasmic reticulum (ER) (5-7), the US3 protein that causes newly synthesized MHC class I molecules to be retained in the ER (8, 9), the US10 protein that selectively targets HLA-G for degradation (10), and US2 and/or US11 proteins that cause selective degradation of folded MEW class I molecules that have dislocated from the ER (10-13). HCMV US2 also destroys HLA-DR-a and DM-a, two components of the MHC class II pathway, to prevent viral antigen recognition by CD4$^+$ T-cells (14). The HCMV proteins UL16, UL18, UL40, UL140, UL141, UL142, UL148A, US18, and US20 plus microRNA-UL112 inhibit NK cell activation by moderating MICA, ULBP, and MICB, HLA-E, CD112, CD155-ligands which normally engage the stimulatory NK cell receptors (15-23). By altering surface levels of T-cell and NK cell receptor ligands, HCMV interferes broadly with cell-mediated immunity.

Ab-mediated immunity is also important for suppressing HCMV infection. Anti-virus IgG antibodies neutralize virions and stimulate immune cells expressing one or more FcγRs, such as FcγRI, FcγRII and FcγRIII (24). Several reports noted the importance of antibodies for controlling infection (25); CMV immune globulin is licensed for prophylaxis of disease in solid organ transplant recipients (26) and is under study to reduce congenital CMV disease. However, latent HCMV can reactivate and is shed, even in the presence of HCMV-specific IgG (27). HCMV can circumvent neutralizing antibodies (nAb) because the heavily glycosylated viral glycoprotein N is poorly recognized (28) or the Fc portion of IgG is found in the viral envelope where it increases the efficiency of virus binding and infection in FcγR-expressing cells (29). Interestingly, the HCMV genome also encodes several decoy FcγRs, which may indirectly prevent the Fcγ-mediated effector consequences of anti-HCMV IgG antibodies (30-32).

The neonatal Fc receptor (FcRn) is composed of a membrane-bound heavy chain (HC) in non-covalent association with β$_2$-microglobulin (β$_2$m) (33, 34). This association of FcRn HC with β$_2$m is required for FcRn complex anterograde transport from the endoplasmic reticulum (ER) (35). Although FcRn shares structural characteristics with WIC class I molecules, it does not present antigenic peptides to cognate T cells due to its narrowed antigen-binding groove (36). Instead, FcRn binds IgG antibodies in a pH-dependent manner with FcRn binding to the Fc-region of IgG at a pH below 6.5 and releasing IgG at higher pHs (37). The FcRn is normally transported to early endosomes and has limited cell surface expression. Within these acidic endosomes, FcRn binds endocytosed IgG (38). Depending on the cell type, FcRn either recycles IgG back to its original cell surface, as is the case with endothelial cells, or transports IgG to the opposite cell surface as is the case with certain polarized epithelial cells in the intestine or placenta. The near neutral pH of the extracellular environment triggers the release of IgG from FcRn. Endocytosed IgG that does not bind FcRn moves to lysosomes where it is degraded (38). FcRn therefore prolongs the half-life of IgG. As an Ab transporter, FcRn helps to establish passive immunity by carrying maternal IgG across the placental syncytiotrophoblast monolayer, as well as across polarized epithelium lining the respiratory, intestinal, and genital tracts (39-41). Also, FcRn is a target for delivering drugs, therapeutics, and vaccines (42-44). In all, FcRn plays a critical role in establishing early neonatal immunity and is involved with immune responses to both natural infection and vaccination.

Little is currently known about the interaction between HCMV and FcRn. HCMV infects placental trophoblasts, epithelial cells, endothelial cells, and hematopoietic stem cells (45-47); FcRn is expressed in each of these cell types (48, 49). Among the hematopoietic cell lineage, FcRn expression is restricted to myeloid cells, including macrophages and dendritic cells (38, 42, 50). Maternal immunity is central to protection of the fetus because infection can occur when neutralizing IgG is low (47), although the role of FcRn has remained somewhat elusive (51). Because FcRn is important in passive immunity, its inactivation could lead to superinfection of an unprotected developing fetus. Here, we have identified that the HCMV membrane glycoprotein US11 specifically captures human FcRn, inhibits its Ab trafficking functions, and causes its degradation in a process known as endoplasmic reticulum-associated degradation (ERAD). This process may be involved with dampening mucosal and maternal immunity and reducing the half-life of IgG in blood and tissues.

Accordingly, methods and compositions are needed to regulate the activity of FcRn.

SUMMARY

It has been discovered that US11 protein, through its interaction with the FcRn protein, facilitates antibody degradation and suppresses antibody function. In addition, FcRn is known to bind to albumin. Accordingly, the present disclosure provides compositions and methods for inhibiting the activity of FcRn in a subject comprising administering to the subject, an effective amount of US11 in a pharmaceutically acceptable form.

In an embodiment, a method of treating a subject suffering from an antibody-mediated autoimmune disease or a risk factor for developing an antibody-mediated autoimmune disease is provided, the method comprising administering to the subject, an effective amount of US11 in a pharmaceutically acceptable form. For such treatments, the administration of US11 is designed, through its interaction with FcRn to facilitate the degradation of auto-antibodies within a subject.

In an embodiment, a method of treating a subject suffering from an albumin-mediated diseases or having a risk factor for developing an albumin-mediated diseases is provided, the method comprising administering to the subject, an effective amount of US11 in a pharmaceutically acceptable form.

In further embodiments, pharmaceutical compositions comprising US11 proteins and a pharmaceutical acceptable carrier are provided. The US11 proteins exhibit properties for use as therapeutic agents, e.g. in the treatment of antibody-mediated autoimmune and albumin-mediated diseases. In addition, certain embodiments relate to pharmaceutical compositions comprising polynucleotides encoding US11 proteins, vectors, and host cells comprising such US11 proteins.

In yet another embodiment, kits comprising the US11 pharmaceutical composition for treatment of antibody-mediated and albumin-mediated diseases are provide. Such kits contain materials useful for the treatment of antibody-mediated autoimmune and albumin-mediated diseases as described herein. The kits may comprise one or more of the following components: a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle).

In addition to the treatment of antibody-mediated autoimmune and albumin-mediated diseases the present disclosure relates to compositions and methods for prevention and/or treatment of HCMV infections. In one embodiment, such treatments are designed to reduce the expression and/or activity of US11 in infected cells. Such reduction in the activity of US11 may also be used in albumin-mediated diseases resulting from aberrant expression of activity of albumin in a subject.

In a specific embodiment, compositions are provided comprising nucleic acid molecules designed to target US11 mRNA and inhibit, silence or attenuated the expression of that RNA. Such compositions may be used in methods for prevention or treatment of HCMV infection. The terms "inhibit," "silencing," and "attenuating" can refer to a measurable reduction in expression of a target mRNA (or the corresponding polypeptide or protein) as compared with the expression of the target mRNA (or the corresponding polypeptide or protein) in the absence of an interfering RNA molecule of the present disclosure. The reduction in expression of the target mRNA (or the corresponding polypeptide or protein) is commonly referred to as "knock-down" and is reported relative to levels present following administration or expression of a non-targeting control RNA.

Such nucleic acid molecules include, for example, "antisense", "siRNA", "shRNA" or "microRNA" or "miRNA". Accordingly, the present disclosure relates to compositions that comprise nucleic acid molecules designed to target the HCMV US11 mRNA and inhibit, silence or attenuated the expression of that RNA and methods for preparing them. In such instances, the nucleic acid molecules contain µ a region of nucleotide sequence that can direct the destruction and/or translational inhibition of the targeted HCMV US11 transcript.

In yet another embodiment, vaccine formulations effective against HCMV, and methods of using the vaccines in the treatment, prevention and prophylaxis of HCMV infections in a subject are provided. The vaccine formulations of the present disclosure comprise full length and/or a portion of the US11 protein and a pharmaceutically acceptable carrier or diluent. The present disclosure provides through the use of US11 vaccines, methods of generating an immune response in a subject to a vaccine formulation of the present disclosure. In one embodiment, the present disclosure is directed to methods of generating an immune response in a subject, comprising administering an immunologically effective amount of a vaccine formulation of the present disclosure to a subject, thereby generating an immune response against HCMV in a subject. In the methods of generating an immune response of the present disclosure, the immune response is preferably a protective immune response against HCMV.

In another aspect of the embodiment, a kit containing materials useful for the treatment or prevention of HCMV infection as described below is provided. In an embodiment, the kit comprises the necessary components of a vaccine formulation that elicits an immune response to HCMV and instructions for its use is also provided herein.

BRIEF DESCRIPTION OF FIGURES

In order to better understand the subject matter that is disclosed herein and to exemplify how it may be carried out in practice, embodiments will now be described, by way of non-limiting example, with reference to the accompanying drawings. With specific reference to the drawings, it is stressed that the particulars shown are by way of example and for purposes of illustrative discussion of embodiments of the disclosure.

FIG. 1A-G. FcRn interacts with HCMV US11. FIG. 1A-B. The cell lysates from HeLa$^{FcRn+US11}$ (lane 1), HeLa$^{FcRn}$ (lane 2), HeLa$^{US11}$ (lane 3), and HeLa control cells (lane 4) were immunoprecipitated by mAb anti-HA for US11 or anti-FLAG for FcRn. The immunoprecipitates were subjected to Western blotting with anti-FLAG or HA mAb as indicated. Cell lysate from each sample with equal amounts of total protein (input, 20 µg) were blotted with the indicated Abs. C. Colocalization of FcRn and US11 in HeLa$^{FcRn+US11}$ cells. HeLa$^{FcRn}$ cells or HeLa$^{US11}$ cells were used as a control. Cells grown on coverslips were fixed with 4% paraformaldehyde and permeabilized in 0.2% Triton X-100. Subsequently, the cells were incubated with affinity-purified anti-FLAG (FcRn) or anti-HA (US11) specific mAb, followed by Alexa Fluro 488- or 555-conjugated IgG. Puncta that appear yellow in the merged images (right panel) indicate colocalization of FcRn with US11 protein. The nuclei were stained with DAPI. Scale bar represents 10 µm. FIG. 1D-E. Cell lysates from HeLa$^{HFE+US11}$ (lane 1), HeLa$^{HFE}$ (lane 2), HeLa$^{US11}$ (lane 3), and HeLa control cells (lane 4) were immunoprecipitated with mAb anti-HA for US11 or anti-FLAG for HFE, respectively. The immunoprecipitates were subjected to Western blotting with anti-FLAG or HA mAb as indicated. The cell lysates (input) were blotted as controls. FIG. 1F-G. US11 interacts with FcRn in HCMV-infected human primary umbilical vein endothelial cells (HUVEC). HUVEC were infected with HCMV at a MOI of 5. At day 2 p.i., the cell lysates from infected or mock-infected HUVEC were immunoprecipitated with anti-US11 Ab (FIG. 1F) or anti-FcRn Ab (FIG. 1G). The immunoprecipitates were subjected to 12% SDS-PAGE electrophoresis under reducing conditions, then transferred to a nitrocellulose membrane for Western blotting with anti-FcRn or US11 Ab as indicated. The cell lysates (20 µg) were blotted as controls. Immunoblots (IB) were developed with ECL.

FIG. 2A-H. US11 expression retains FcRn in the endoplasmic reticulum (ER). FIG. 2A-B. US11 reduces the trafficking of FcRn to the endosomal compartment. FIG. 2A FcRn appearance in the endosome in HeLa$^{FcRn+US11}$ and HeLa$^{FcRn}$ cells. Both cells were immunostained for FcRn and EEA1. Colocalization of two molecules appears in the figure. The nuclei were stained with DAPI. Similar images were seen in at least three independent staining experiments. Scale bar represents 10 µm. FIG. 2B. Averages of the EEA1 and FcRn colocalization coefficients in HeLa$^{FcRn+US11}$ and HeLa$^{FcRn}$ cells. Pearson's correlation coefficient was measured. 100 cells (total) were analyzed in 10 different optical regions in each experiment. FcRn trafficking to the early endosome decreases in HeLa$^{FcRn+US11}$; in comparison with HeLa$^{FcRn}$ cells (top panel). FIG. 2C-D. CD71 (transferrin receptor) trafficking to the early endosome. HeLa$^{FcRn+US11}$ and HeLa$^{FcRn}$ cells were transfected with a plasmid expressing human CD71-GFP and immunostained for EEA1. The nuclei were stained with DAPI. CD71 trafficking to the early endosome was not significantly altered in HeLaFcRn+US11 cells in comparison with HeLa$^{FcRn}$ cells (top panel). Average of the EEA1 and CD71 colocalization coefficients in US11+ and US11 cells is shown. EEA1: early endosome antigen 1. The nuclei were stained with DAPI; Colocalization of two molecules appears in figure. Scale bar represents 10 µm. Similar images were seen from at least three independent staining experiments. (FIG. 2D) Average of the EEA1 and CD71 colocalization coefficients in HeLa$^{FcRn+US11}$ and HeLa$^{FcRn}$ cells is shown. ***P<0.001; NS: no significance. FIG. 2E-F. β2m or US11 does not coimmunoprecipitate with US11 or β2m protein. Cell lysates from HeLa$^{FcRn+US11}$ (lane 1), HeLa$^{FcRn}$ (lane 2), HeLa$^{US11}$ (lane 3), and HeLa control cells (lane 4) were immunoprecipitated by anti-HA mAb (FIG. 2E), anti-β2m Ab (FIG. 2F). The immunoprecipitates and cell lysates (input) were subjected to 12% SDS-PAGE electrophoresis under reducing conditions, then transferred to a nitrocellulose membrane for blotting with anti-β2m Ab, anti-FLAG (FcRn), anti-HA (US11), as indicated. Immunoblots were incubated with HRP-conjugated secondary Ab of the corresponding species and developed with ECL. FIG. 2G-H. Sensitivity of US11-associated FcRn HC to Endo-H digestion. (FIG. 2G). Native FcRn in cell lysates (top panel) or proteins immunoprecipitated by HA mAb (bottom panel) were digested by mock (lanes 1 and 4), Endo-H (lanes 2 and 5), or PNGase F (lanes 3 and 6) for 2 h at 37° C., respectively. Proteins were analyzed on a 12% SDS-PAGE gel under reducing conditions and immunoblotted with FcRn-specific Ab. The ratio of Endo H-resistant (Endo-HR) FcRn HC to Endo H-sensitive (Endo-HS) FcRn HC from Hela$^{FcRn+US11}$ and HeLa$^{FcRn}$ cells were compared by the ratio of the band density of glycosylated FcRn to that of the deglycosylated FcRn (FIG. 2H). The band density of Endo-H sensitive or resistant FcRn (FIG. 2G, top panel, lanes 2 and 5) was quantified by the software Image Lab 5.2. The digestion experiments were independently performed three times. Star denotes statistical significance (*P<0.05). R: Resistant; S: Sensitive.

FIG. 3A-K. US11 protein mediates FcRn degradation. FIG. 3A-B. Cell surface and intracellular expression patterns of FcRn and HFE in either fixed or permeabilized US11-expressing cells were measured by flow cytometry. Cells were stained as described in Materials and Methods. The red or blue histograms represent staining of cells with anti-FLAG (FcRn or HFE)-specific Ab with or without expression of US11, and the black histograms represent cells stained with isotype-matched IgG. The staining was performed three times with similar results. The mean fluorescence intensity (MFI) is shown on the x-axis, and the relative cell number on the y-axis. Results are expressed as histograms of fluorescence intensity (log scale). FIG. 3C-F. HeLa$^{FcRn}$ cells were transfected with US11 plasmids for 24 h. HeLa$^{FcRn+US11}$ (FIG. 3C) and HeLa$^{FcRn}$ (FIG. 3D) cells were then treated with CHX (100 µg/ml) for the indicated time. These experiments were performed independently three times. FIG. 3G-K. HUVEC cells were infected with clinic strain HCMV (MOI 5) (FIG. 3G) or mock-infected (FIG. 3I) for 48 hr. The infected cells were also transfected with 20 nM US11 siRNA oligomers (FIG. 3K). 48 hr later, cells were then treated with CHX (100 µg/ml) for the indicated time. The cells were lysed after CHX treatment, protein levels were measured, and Western blotting and ECL were performed. The level of remaining endogenous FcRn (FIG. 3D or FIG. 3H) and β2m (FIG. 3F or FIG. 3J) at different time points was quantified as the percentage of the β-tubulin level. The percentage of time point 0 (min) is assigned a value of 100% and the values from other time points are normalized to this value. Each experiment was carried out three times.

FIG. 4A-I. US11 recruits FcRn to Derlin-1 and TMEM129 protein complex. FIG. 4A-C. US11 recruits FcRn to the Derlin-1 complex. US11Q192L represents a mutant US11 in which Q192 is replaced with leucine, US11$^{Q192L}$. Stable HeLa FcRn HeLa$^{FcRn+US11}$, HeLa$^{FcRn+US11\ Q192L}$, HeLa$^{US11}$, and HeLa$^{US11\ Q192L}$ cell lines were transiently transfected with a plasmid encoding myc-tagged Derlin-1. 48 h after transfection, the cell lysates (0.5 mg) were immunoprecipitated with mAb anti-FLAG for FcRn (FIG. 4A+FIG. 4C) or anti-myc for Derlin-1 (FIG. 4B). Non-transfected HeLa$^{FcRn}$ or HeLa cells were used as a negative control. Precipitated proteins (FIG. 4A, FIG. 4B, FIG. 4C) were subjected to Western blotting with the specific Ab. The precipitates were subjected to 12% SDS-PAGE electrophoresis under reducing conditions, then transferred to a nitrocellulose membrane. Immunoblots (IB) were developed with ECL, as indicated. The cell lysates (20 μg, input) were blotted as controls. FIG. 4D+FIG. 4E. FcRn in mutant US11$^{Q192L}$ transfected cells resists degradation. HeLa$^{FcRn+US11}$ and HeLa$^{FcRn+US11+}$cells were treated with CHX (100 μg/ml) for the indicated time (FIG. 4D). The cells were lysed, protein levels were measured, and Western blotting-ECL was performed. The level of remaining FcRn (FIG. 4E) at different time points was quantified as the percentage of the β-tubulin level. These experiments were performed independently three times. FIG. 4F+FIG. 4G. US11 recruits FcRn to TMEM129 complex. HeLa$^{FcRn+US}$11 (lane 1), HeLa$^{FcRn}$ (lane 2), HeLa$^{US11}$ (lane 3), and HeLa cells were transfected with Derlin-1 plasmid. 48 h later, the cell lysates were immunoprecipitated by mAb anti-FLAG for FcRn (FIG. 4F) or anti-TMEM129 Ab (FIG. 4G). The immunoprecipitates were subjected to 12% SDS-PAGE electrophoresis under reducing conditions, and then transferred to a nitrocellulose membrane for Western blotting with antibodies as indicated. The cell lysates (20 μg, input) were blotted with the indicated Abs. Immunoblots (IB) were developed with ECL. FIG. 4H+FIG. 4I. TMEM129 is involved in US11-mediated FcRn degradation. The HeLa$^{FcRn+US11}$ cells were transfected with 20 nM TMEM129 siRNA oligomers (H, bottom). 48 h later, cells were then treated with CHX (100 μg/ml) for the indicated time. The cells were lysed, protein levels were measured, and Western blotting-ECL was performed. The level of remaining FcRn (I) in TMEM129 siRNA-treated cells or mock-treated cells at different time points was quantified as the percentage of the β-tubulin level. These experiments were performed independently three times.

FIG. 5A-F. The cytoplasmic tail of FcRn contributes to US11-mediated degradation. FIG. 5A. Depiction of FcRnCT (SEQ ID NO:11), tailless FcRn (CT−/−) (SEQID NO:11) and FcRn HC deleting alanine residue 365 (365A−/−) (SEQ ID NO:11) in the cytoplasmic tail. Letter(s) in gray represent(s) the deleted amino acid(s). FIG. 5B+FIG. 5C. Tailless FcRn or FcRn 365A−/− resists degradation in the presence of US11. HeLa$^{US}$11 (FIG. 5B, top), Hel a US11+FcRn CT−/− (FIG. 5B, middle), or HeLa$^{US11+FcRn365-/-}$ cells (FIG. 5B, bottom) were treated with CHX (100 μg/ml) and chased for the indicated time in the absence of proteasome inhibitors. Cell lysates were subjected to 12% SDS-PAGE electrophoresis, then transferred to a nitrocellulose membrane. Immunoblots (IB) were done with the indicated specific Abs and developed with ECL. The β-tubulin (input) was blotted as controls. The level of wild-type FcRn, tailless FcRn, and mutant FcRn 365A−/− in HeLa$^{US11}$ cells at different time points was quantified as the percentage of the β-tubulin level. These experiments were performed three times. FIG. 5D. The US11 interacts with tailless FcRn protein. The cell lysates from HeLa$^{FcRn+US11}$ (lane 1), Hela$^{US11+FcRn\ CT-/-}$ (lane 2), and HeLa$^{control}$ (lane 3) were immunoprecipitated by anti-FLAG Ab for FcRn. The immunoprecipitates and cell lysates (input) were subjected to 12% SDS-PAGE electrophoresis, then transferred to a nitrocellulose membrane for blotting with anti-FLAG (FcRn), anti-HA (US11), as indicated. Immunoblots were incubated with HRP-conjugated secondary Ab of the corresponding species and developed with ECL. The US11 molecules that coprecipitate in the complex are indicated. FIG. 5E. The cytoplasmic tail of FcRn is required for tightly binding to Derlin-1 in the presence of US11. HeLa$^{FcRn+US11}$ (lane 1), HeLa$^{US11+FcRn\ CT-/-}$ (lane 2), and HeLa$^{US11+FcRn\ 365A-/-}$ (lane 3) cells were transfected with Derlin-1 plasmid. 48 hr later, cell lysates were immunoprecipitated with anti-FLAG Ab to detect FcRn. Immunoprecipitates and cell lysates (input) were subjected to 12% SDS-PAGE electrophoresis, and then transferred to a nitrocellulose membrane for blotting with anti-TMEM129, anti-Myc (Derlin-1), anti-FLAG (FcRn), anti-HA (US11), as indicated by arrows. Immunoblots were incubated with HRP-conjugated secondary Ab of the corresponding species and developed with ECL. FIG. 5F. The C-terminus of Derlin-1 is required for tightly binding to FcRn in the presence of US11. The HeLa$^{US11+FcRn}$ stable cells were transfected with a plasmid encoding Myc-tagged Derlin-1 (WT), Derlin-1 lacking its N-terminus (NT−/−) or C-terminus (CT−/−), respectively. 48 hr after transfection, cells were lysed in 0.5% CHAPS containing the protease inhibitors. The 500 μg of proteins from each transfectant was precipitated by rabbit anti-FLAG Ab. The immunoprecipitated products were subjected to SDS-PAGE and Western blot analysis by respective antibodies as indicated.

FIG. 6A-I. US11/Derlin-1/TMEM129/Ube2J2 protein complex induces FcRn dislocation, ubiquitylation, and degradation. FIG. 6A-D. FcRn is ubiquitinated in the presence of US11 and MG132. HeLa$^{FcRn}$ (FIG. 6A), HeLa$^{HFE}$ (FIG. 6B), HeLa$^{FcRn\ CT-/-}$ (FIG. 6C, lane 2), and HeLa$^{FcRn\ 365A-/-}$ (FIG. 6C, lane 3) cells were transfected with or without US11 plasmids for 48 hr, and cells were treated with proteasome inhibitor MG132 (50 μM) for 2 hr, as indicated. HeLa$^{FcRn}$ or HeLa$^{FcRn+US11}$ cells (FIG. 6D) were treated with CHX (100 μg/ml) and chased for the indicated time in the presence of MG132. Cell lysates (0.5 mg) were immunoprecipitated with mAb anti-FLAG for FcRn (FIG. 6A-D) or HFE (FIG. 6B). Immunoprecipitates were subjected to the electrophoresis and immunoblotting analysis to detect ubiquitin and the target proteins FcRn, HFE, US11, or β-tubulin with corresponding Abs, as indicated. Ubiquitinated proteins in the cell lysates (20 μg, FIG. 6A+B) were blotted as an internal control. FIG. 6E. Fractionation of FcRn HC. HeLa$^{FcRn}$. HeLa$^{US11+FcRn}$ cells were incubated in the presence or absence of 50 μM MG132 for 4 hr. Cells were then homogenized and the homogenates were fractionated by centrifugation (see Materials and Methods). Fractions were diluted by 1% Triton X-100 buffer. FcRn in the membrane pellet (M, lanes 1, 3, 5, 7) and supernatant (S, lanes 2, 4, 6, 8) fraction was digested by mock (top), Endo-H (middle), PNGase F (bottom) enzymes for 2 h at 37° C., respectively. Proteins were analyzed on a 12% SDS-PAGE gel and immunoblotted with FcRn-specific Ab. R: resistant; S: sensitive. FIG. 6F+FIG. 6G. TMEM129 and Ube2J2 is required for US11-induced FcRn ubiquitination. HeLa$^{FcRn+US11}$ cells were transfected with 20 nM TMEM129, Ube2J1, or Ube2J2 siRNA oligomers for 48 hr or empty vector. Efficacy of TMEM129 silencing was analyzed 72 hr after transfection. Cells were subsequently treated with 50 μM MG132 for 24 hr and then lysed. After immunoprecipitation of FcRn with anti-FLAG, immunoprecipitated complexes or 20 μg of cell lysates were analyzed by immunoblotting with the indicated antibodies, respectively. FIG. 6H+FIG. 6I. Ube2J2 are essential for US11-induced FcRn degradation and ubiquitination. HeLa$^{US11+FcRn}$ cells were transfected with 20 nM Ube2J1 (top) and Ube2J2 (bottom) siRNA oligomers for 48 hr. Cells were then treated with CHX (100 μg/ml) and chased for the indicated time. Subsequently cells were lysed in PBS with 0.5% CHAPS and protease inhibitor cocktail III. Cell lysates (20 μg) were individually probed with Abs for detection of FcRn, Ube2j, or tubulin and developed with ECL (FIG. 6H). The level of remaining FcRn (FIG. 6I) in Ube2j1 siRNA-treated cells or Ube2j2 siRNA-treated cells was quantified as the percentage of the β-tubulin level at different time points. These experiments were performed independently three times.

FIG. 7A–J. HCMV infection or US11 expression alone reduces FcRn-mediated IgG transcytosis in polarized epithelial monolayers. FIG. 7A–D. The presence of US11 reduces FcRn binding to IgG. HeLa transfectants were lysed in sodium phosphate buffer pH 6.0 (FIG. 7A) or pH 7.4 (FIG. 7B) with 0.5% CHAPS and fresh proteinase inhibitors. Approximately 0.5 mg of soluble proteins were incubated with human IgG-Sepharose at 4° C. Eluted proteins were subjected to Western blotting analysis. Proteins were probed with rabbit anti-FLAG (FcRn), anti-HA (US11), or anti-β2m Ab and developed with HRP-conjugated secondary Abs of the corresponding species and ECL was performed. Cell lysates from each sample with equal amounts of total protein were also blotted for FcRn, US11, and β2m. The location of human FcRn HC, US11, and β2m proteins are indicated by arrows. FcRn or β2m proteins were eluted from IgG at pH 6.0 (FIG. 7A). The amount of eluted FcRn (FIG. 7C) or β2m (FIG. 7D) protein from HeLa$^{FcRn}$ and HeLa$^{FcRn+US11}$ cells was compared by the ratio of the band density of eluted protein to that of input protein. The density of protein bands was quantified by the Image Lab 5.2 software. Binding experiments were independently repeated three times. FIG. 7E–H. Caco-2 cells ($2\times10^4$/well) or BeWo cells ($10^5$/well) were grown in 0.4 μm transwell plates for 8 to 10 days (Caco-2) or for 4 days (BeWo) to allow differentiation. When the transepithelial resistance of the cell monolayer reached above 600 (Caco-2) or 400 (BeWo) ohms·cm$^2$, cells were infected at the basolateral surface with HCMV (MOI 5) for 1 hr. After washing, cells were incubated for additional 48 h. Infected or mock-infected cells were loaded at the apical surface with human IgG (lanes 1-4) (0.5 mg/ml for Caco-2 or 0.25 mg/ml for BeWo) at 37° C. or 4° C., respectively. Medium was collected from the basolateral compartment 2 hr later and subjected to Western blot-ECL (FIG. 7E or FIG. 7G) or ELISA (FIG. 7F+H) analysis. FIG. 7I+FIG. 7J. Caco-2 cells transfected with either pEF6 or pEF6-US11 were grown on transwell inserts as described above. The cells were incubated for 1 hr at 37° C. or 4° C., then human IgG (0.5 mg/ml) was added to the apical surface and further incubated for 2 hr to allow transcytosis. Medium from the basolateral compartment was collected and human IgG content was measured by Western blot-ECL (FIG. 7I) or ELISA (FIG. 7J). The results are representative of at least three independent experiments. *P<0.05, P<0.01, and *P<0.001.

FIG. 8A–F. HCMV infection increases IgG catabolism in human endothelial cells. FIG. 8A+FIG. 8B. HEMC-1 cells ($5\times10^5$/2 ml) were grown in complete medium with 5% FBS with ultra-low IgG. After cells were infected with 5 MOI of HCMV or mock-infected for 48 hr, they were incubated with 50 μg/ml human IgG for 48 hr at 37° C. After washing, cells were incubated at 37° C. During the incubation, 50 μl of supernatant was sampled at 0, 12, 24, 36, and 48 hr and the IgG concentration in each sample was measured by ELISA (FIG. 8A). At 48 hr, the IgG concentration in the medium from the HCMV-infected and mock-infected cells was analyzed by t-test (FIG. 8B). The experiments were performed at least three times. FIG. 8C-F. To visualize human IgG trafficking inside infected HEMC-1 ($5\times10^4$) cells, cells were infected with 5 MOI of HCMV for 48 hr and incubated with 250 μg/ml human IgG for 1 hr at 37° C. After washing, cells were incubated in complete medium without IgG for an additional 1 hr, then fixed and stained for co-localization of human IgG with the early endosomal marker EEA1 (FIG. 8C) or lysosomal marker LAMP-1 (FIG. 8E). For Pearson's correlation coefficient measurement, 10 microscopic fields, each of which contained at least 10 cells, were measured for correlation coefficiency rate (FIG. 8D+FIG. 8F). P<0.01, and *P<0.001.

FIG. 10A. The cell lysates from HeLa$^{FcRn+US11}$ (lane 1), HeLa$^{FcRn}$ (lane 2), HeLa$^{US11}$ (lane 3), and HeLa control (lane 4) were immunoprecipitated by mAb anti-HA for US11. FIG. 10B+FIG. 10C. The cell lysates from HeLa$^{FcRn+US2}$ (lane 1), HeLa$^{FcRn}$ (lane 2), HeLa$^{US2}$ (lane 3), and HeLa control (lane 4) were immunoprecipitated by mAb anti-HA for US2 or anti-FLAG for FcRn. The immunoprecipitates were subjected to 12% SDS-PAGE electrophoresis under reducing conditions, then transferred to a nitrocellulose membrane for Western blotting with anti-TfR1, anti-FLAG (FcRn), or HA (US11) mAb as indicated. Immunoblots (IB) were developed with ECL. The 50 μg cell lysates (input) were blotted with the indicated Abs. The location of the TfR1, FcRn HC or US2 is indicated by an arrow.

FIG. 12A–H. FcRn interacts with US11 in HCMV-infected human THP-1, endothelial HMEC-1, and human intestinal Caco-2 epithelial cells. THP-1 cells were treated with 50 ng/ml PMA or left untreated for 48 hrs. THP-1 cells (FIG. 12A–D), HMEC-1 cells (FIG. 12E–F), and Caco-2 cells (FIG. 12G–H) were mock-infected or infected for 24 hrs with clinical strain HCMV at an MOI of 5. HeLa$^{FcRn}$ and HeLa cells were used as controls (FIG. 12G+FIG. 2H). The cell lysates were immunoprecipitated by US11 or FcRn specific Abs. The immunoprecipitates were subjected to 12% SDS-PAGE electrophoresis under reducing conditions, then transferred to a nitrocellulose membrane for Western blotting with anti-US11 or FcRn as indicated. Immunoblots (IB) were developed with ECL. The 20 μg cell lysates (input) were blotted with the indicated Abs. pp65, an HCMV major tegument protein, is used for monitoring viral infection. The location of the proteins is indicated by an arrow.

FIG. 13A–C. US11 interacts with FcRn through its ER-luminal domain. The cDNA fragment encoding extracellular domain of US11 or cytoplasmic tail of FcRn was fused to the GST and expressed as a GST HCMV US11 protein. Productions of GST HCMV US11 protein are described in Materials and Methods. FIG. 13A. GST, GST-US11, and GST-FcRn CT HCMV US11 protein were stained with Commassie blue and used for in vitro pull-down assays. FIG. 13B. GST-US11 proteins were incubated with the cell lysates from HeLa$^{FcRn}$ (lane 1) or FcRn-negative HeLa (lane 2) cells. GST proteins are shown as negative controls in lanes 3, 4, respectively. Cell lysates are used as loading control (lanes 5, 6). FIG. 13C. FcRn cytoplasmic tail (CT) expressed as a GST HCMV US11 protein were incubated with HeLa$^{US11}$ (lane 1), HeLa (lane 2). GST protein is a control in lanes 3 and 4. HeLa$^{US11}$ or HeLa cell lysates are used as loading control (lanes 5, 6). Beads were completely washed with buffers. In each experiment, GST-HCMV US11 protein binding was assessed by immunoblot as indicated. FIG. 14A–I. Time course effects of HCMV infection on FcRn protein and mRNA expression. FIG. 14A–E. Caco-2 cells were infected with clinical strain HCMV (MOI 5) (FIG. 14A) or mock-infected (FIG. 14C) for 48 hr. The infected cells were also transfected with 20 nM US11 siRNA oligomers (FIG. 14E). 48 hr later, cells were then treated with CHX (100 μg/ml) for the indicated time. The cells were lysed after CHX treatment, protein levels were measured, and Western blotting and ECL were performed. The level of remaining endogenous FcRn (FIG. 14B) and β2m (FIG. 14D) at different time points was quantified as the percentage of the β-tubulin level. Each experiment was carried out at least three times. FIG. 14F–FIG. 14I. Human intestinal cell line Caco-2 was mock infected (left) or infected with HCMV (MOI 5, right). Total RNA was isolated at the indicated time by TRIzol reagent and analyzed by semi-quantitative RT-PCR for FcRn mRNA. GAPDH amplification was used as an internal control. PCR amplifications were run at 34 (FIG. 14F, top) or 29 (FIG. 14H, bottom) cycles to exclude the potential saturation of PCR amplification. The relative FcRn mRNA levels (FIG. 14G or FIG. 14I) were calculated by the ratio of FcRn mRNA levels to GAPDH mRNA levels. The mRNA levels were quantified by the DNA band density (relative band volume) as measured by Image Lab 5.2.

FIG. 15A-B. Intracellular Expression of FcRn in HCMV-infected THP-1 and HMEC-1 cells. Intracellular expression of FcRn in mock- or HCMV-infected THP-1 (FIG. 15A) and HMEC-1 (FIG. 15B) cells (106) at an MOI of 5 were measured by flow cytometry. 48 hr post infection, the equal number of cells were treated with Cycloheximide (100 μg/ml) or left untreated for 4 hr. Cells were then blocked with 2% FBS supplemented with 30 μg/ml human Fc block and subsequently stained as described in Materials and Methods. Results are expressed as histograms of fluorescence intensity (log scale). The histograms represent staining of cells with anti-FcRn-specific Ab in the presence or absence of HCMV infection, and the black histograms represent cells stained with irrelevant IgG. The staining was conducted three times with similar results. The mean fluorescence intensity (MFI) is shown on the x-axis, and the relative cell number on the y-axis.

FIG. 16A. The interaction between US11 and Derlin-1 is dependent on a polar glutamine residue in the US11 transmembrane domain. HeLa$^{US11}$ or HeLa$^{US11Q192L}$ stable cells were lysed and US11 was immunoprecipitated and eluted in SDS sample buffer. Immune precipitates (top) and total lysates (bottom) were analyzed by SDS/PAGE and probed for TMEM129, Derlin-1, and US11. Derlin-1 and TMEM129 associates with wild-type US11 but association with the mutant US11-Q192L is dramatically reduced. FIG. 16B. US11-Q192L fails to induce FcRn ubiquitination. HeLa$^{FcRn}$ cells were transfected with PEF6 plasmid or pEF6-HA-US11Q192L for 24 hr. Cells were subsequently treated with 50 μM MG132 for 4 hr and then lysed in PBS with 0.5% CHAPS and protease inhibitor cocktail. After immunoprecipitation of FcRn with rabbit anti-FLAG, immunoprecipitated complexes were subjected to SDS-PAGE and analyzed by Western blot-ECL with mouse anti-ubiquitin Ab. The cell lysates (20 μg) from each sample were blotted for monitoring the levels of FcRn or US11Q192L expression.

FIG. 17A. Caco-2 cells transfected with a plasmid encoding US11. Caco-2 cells were transfected with US11 plasmid and grown on glass coverslips. 48 hr later, monolayers were fixed with 4% paraformaldehyde and permeabilized in 0.2% Triton X-100. Subsequently, the cells were incubated with HA specific Ab for US11, followed by Alexa Fluro 555-conjugated IgG. The nuclei were stained with DAPI. FIG. 17B. HCMV-infected HECM-1. HECM-1 cells were grown on glass coverslips and infected with HCMV at an MOI of 5. At day 2 p.i., monolayers were fixed with 4% paraformaldehyde and permeabilized in 0.2% Triton X-100. Subsequently, the cells were incubated with affinity-purified anti-US11 or anti-pp65 specific Ab, followed by Alexa Fluro 488- or 555-conjugated IgG. Specific staining yellow in the merged images indicates colocalization of US11 with pp65. The nuclei were stained with DAPI.

FIG. 18A–D. Human IgG trafficking inside HeLa$^{FcRn+US11}$ and HeLa$^{FcRn}$ cells. To visualize human IgG trafficking inside HeLa$^{FcRn+US11}$, HeLa$^{FcRn}$ (1×10$^5$) cells, they were incubated with 250 μg/ml human IgG for 1 hr at 37° C. After complete washing, cells were incubated with complete medium without IgG for an additional 1 hr, then fixed and stained by immunofluorescence for the co-localization of human IgG with the early endosomal marker EEA1 (FIG. 18A) or lysosomal marker LAMP1 (FIG. 18C). For Pearson's correlation coefficiency measurement, 10 scopes, each of which contains at least 10 cells, were measured for correlation coefficiency rate (FIG. 18B & FIG. 18D). ***P<0.001.

FIG. 19A–F. Human IgG recycling is significantly reduced when cells express US11 and infected with HCMV. Human IgG recycling assay was performed according to a modified method (87). HeLa$^{FcRn}$ and HeLa$^{FcRn+US11}$ cells (FIG. 19A+FIG. 19B), HMEC-1 cells were infected with 5 MOI of HCMV or mock-infected (FIG. 19C+FIG. 19D), and HMEC-1 cells were transfected with 2 μg pEF6US11 or pEF6 (mock) plasmids by Lonza Nucleofector Kit R (VCA1001) (FIG. 19E+FIG. 19F) and the cells were seeded in a 24 well plate (10$^5$ cells/well) for 48 hr. All cells were washed and starved for 1 hr in HBSS medium, and then incubated with human IgG (5 or 25 μg/250 μl) at either pH 6.0 or pH 7.4 condition for 4 hr. The cells were subsequently washed 4 times by HBSS (pH 7.4) and then incubated for additional 4 hrs at 37° C. The supernatants were sampled, and the recycled IgG was measured by ELISA. *P<0.05, P<0.01, and *P<0.001.

FIG. 21A+FIG. 21B. The cells were lysed after CHX treatment and the protein levels were measured, and the Western blotting-ECL was performed. The level of HLA-A2 was quantified as the percentage of β-tubulin content at different time points (FIG. 21C). These experiments were performed three times. FIG. 21D. Cell surface expression patterns of HLA-A2 protein in the presence of US11 were measured by flow cytometry. Results are expressed as histograms of fluorescence intensity (log scale). The histograms represent staining of HeLa$^{HLA-A2+US11}$ or HeLa$^{HLA-A2}$ cells with anti-FLAG specific Ab. The black histograms represent cells stained with isotype-matched IgG. The staining was conducted three times with similar results. The mean fluorescence intensity (MFI) is shown on the x-axis, and the relative cell number on the y-axis.

DETAILED DESCRIPTION

Definitions

Figure 2A:
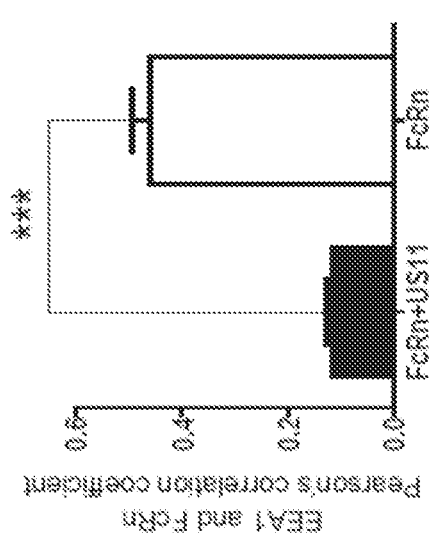

The term "autoimmune disease" as used herein means a condition or disease characterized by an overactive immune system, where the body attacks and damages its own tissues and organs. In antibody-mediated immune diseases the body produces antibodies that destroy these tissues and organs.

The term "albumin-mediated disease" as used herein means a condition or disease characterized by aberrant levels of albumin in a subject. In some embodiments the disorder may result from overexpression of albumin, while in others it may result from a deficiency of albumin. Such diseases include for example, cirrhosis and inflammation, acute infections, burns and stress from surgery or a heart attack. In disorders characterized by high levels of albumin, US11 may be administered to lower the levels of circulating albumin. In disorders characterized by low levels of albumin, inhibitors of US11 may be administered.

The terms "effective amount" or "therapeutically effective amount" as used herein have the standard meanings known in the art and are used interchangeably herein to mean an amount sufficient to treat a subject afflicted with a condition or disease (e.g., antibody-mediated autoimmune or albumin-mediated diseases) or to halt the progression of the condition or disease, or alleviate a symptom or a complication associated with the condition or disease. The exact dose will depend on the purpose of the treatment, and will be ascertainable by one skilled in the art using known techniques (e.g., Ansel et al., Pharmaceutical Dosage Forms and Drug Delivery; Lieberman, Pharmaceutical Dosage Forms (vols. 1-3, 1992), Dekker, ISBN 0824770846, 082476918X, 0824712692, 0824716981; Lloyd, The Art, Science and Technology of Pharmaceutical Compounding (1999); and Pickar, Dosage Calculations (1999)). For example, in the case of an agent to treat antibody-mediated autoimmune and albumin-mediated disease, an effective amount may be an amount sufficient to result in clinical improvement of the patient.

The terms "protein" and "polypeptide" as used herein are used interchangeably, unless specified to the contrary, and according to conventional meaning, mean a sequence of amino acids. Peptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring, e.g. variants.

The term "subject" as used herein refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human. A subject in need is a subject that is suffering from a cardiac condition or disease or that has a risk factor for developing a cardiac condition or cardiac disease.

The term "therapeutic agent" as used herein is a compound capable of producing a desired and beneficial effect.

The terms "treat," "treating" or "treatment" of any disease or disorder as used herein refer in one embodiment, to halting the progression of the condition or disease, or to ameliorating the disease or disorder (i.e., slowing or arresting or reducing the development of the disease or at least one of the clinical symptoms thereof). In another embodiment "treat," "treating" or "treatment" refers to alleviating or ameliorating at least one physical parameter including those which may not be discernible by the patient. In yet another embodiment, "treat," "treating" or "treatment" refers to modulating the disease or disorder, either physically, (e.g., stabilization of a discernible symptom), physiologically, (e.g., stabilization of a physical parameter), or both. In yet another embodiment, "treat," "treating" or "treatment" refers to preventing or delaying the onset or development or progression of the disease or disorder. As used herein, a subject is "in need of" a treatment if such subject would benefit biologically, medically or in quality of life from such treatment.

The term "vector" as used herein refers to any molecule or entity (e.g., nucleic acid, plasmid, bacteriophage or virus) used to transfer protein coding information into a host cell. Certain vectors are capable of directing the expression of nucleic acids to which they are operatively linked. Such vectors are referred to herein as "expression vectors." An "expression vector" or "expression construct" as used herein refers to a recombinant DNA molecule containing a desired coding sequence and appropriate nucleic acid control sequences necessary for the expression of the operably linked coding sequence in a particular host cell.

HCMV US11, which encodes an endoplasmic reticulum (ER) resident type-I transmembrane glycoprotein, has been shown herein to bind to the FcRn protein and inhibit the activity of said protein. Accordingly, the present disclosure provides methods for inhibiting the activity of FcRn in a subject comprising administering to the subject, an effective amount of US11 in a pharmaceutically acceptable form. As used herein, the term "HCMV US11" or "US11" refers to a protein having the following amino acid sequence (SEQ ID NO: 1):

MNLVMLILALWAPVAGSMPELSLTLFDEPPPLVETEPLPPLSDV

SEYRVEYSEARCVLRSGGRLEALWTLRGNLSVPTPTPRVYYQTLEGYADR

VPTPVEDVSESLVAKRYWLRDYRVPQRTKLVLFYFSPCHQCQTYYVECEP

RCLVPWVPLWSSLEDIERLLFEDRRLMAYYALTIKSAQYTLMMVAVIQVF

WGLYVKGWLHRHFPWMFSDQW.

Nucleic acid sequences encoding a US11 protein include those of the following nucleotide sequence (SEQ ID NO: 2):

```
  1 cagccttaca gcttttgagt ctagacaggg gaacagcctt cccttgtaag acagaatgaa
 61 ccttgtaatg cttattctag ccctctgggc cccggtcgcg ggtagtatgc ctgaattatc
121 cttgactctt ttcgatgaac ctccgccctt ggtggagacg gagccgttac cgcctctgtc
181 cgatgtttcg gagtaccgag tagagtattc cgaggcgcgc tgcgtgctcc gatcgggcgg
241 tcgactggag gctctgtgga ccctgcgcgg gaacctgtcc gtgcccacgc cgacacctcg
301 ggtgtactac cagacgctgg agggctacgc ggatcgagtg ccgacgccgg tggaggacgt
361 ctccgaaagc ctcgtcgcaa aacgctactg gctccgggac tatcgtgttc cccaacgcac
421 aaaactcgtg ttgttctact tttcccctg ccaccaatgc caaacttatt atgtagagtg
481 cgaaccccgg tgcctcgtgc cttgggttcc cctgtggagc tcgttagagg acatcgaacg
541 attattgttc gaagatcgcc gtctaatggc gtactacgcg ctcacgatta agtcggcgca
601 gtatacgctg atgatggtgg cagtgattca agtgttttgg gggctgtatg tgaaaggttg
661 gctgcaccga catttttccct ggatgttttc ggaccagtgg tgatatatag actgaagcgg
721 agtgcatctc gagtcgctcg gaaacgactc accagacttt ttgctttaac ccgaaacc
```

Such US11 proteins, also include polypeptide fragments of US11, as well as variants of the protein. Full length protein, polypeptide fragments and variants are collectively referred to herein in "US11 proteins".

Accordingly, the present disclosure provides methods for inhibiting the activity of FcRn in a subject comprising administering to the subject, an effective amount of US11 in a pharmaceutically acceptable form. The present disclosure provides methods and pharmaceutical composition for treatment of antibody-mediated autoimmune and albumin-mediated diseases by administering a US11 protein to a subject in need.

In an embodiment, a method of treating a subject suffering from an antibody-mediated autoimmune or having a risk factor for developing an antibody-mediated autoimmune disease is provided, the method comprising administering to the subject, an effective amount of US11 in a pharmaceutically acceptable form. Such auto-immune diseases include, but are not limited to ankylosing spondylitis, lupus, rheumatoid arthritis, juvenile arthritis, scleroderma dermatomyositis, behcet's disease, reactive arthritis, mixed connective tissue disease, raynaud's phenomenon, giant cell arteritis/ temporal arteritis, polymyalgia rheumatica, polyarteritis nodosa, polymyositis, takayasu arteritis, granulomatosis with polyangiitis, and vasculitis, alopecia areata, antiphospholipid antibody syndrome, autoimmune hepatitis, type 1 diabetes, celiac disease, Chron's disease, Graves' disease, Guillain-Barre syndrome, Hashimoto's disease, idiopathic thrombocytopenic purpura, inflammatory bowel disease, multiple sclerosis, myasthenia gravis, primary biliary cirrhosis, psoriasis, Sjogren's syndrome, vitiligo, bullous pemphigoid, pemphigus foliaceus, pemphigus vulgaris and epidermolysis bullosa acquisita.

In an embodiment, a method of treating a subject suffering from as albumin-mediated disease or having a risk factor for developing an albumin-mediated disease is provided, the method comprising administering to the subject, an effective amount of US11 in a pharmaceutically acceptable form. Such albumin-mediated diseases include, for example, those resulting from overexpression or underexpression of albumin.

In further embodiments, pharmaceutical compositions comprising US11 proteins and a pharmaceutical acceptable carrier are provided. The US11 proteins exhibit properties for use as therapeutic agents, e.g. in the treatment of antibody-mediated autoimmune and albumin-mediated diseases. In addition, certain embodiments relate to compositions comprising polynucleotides encoding such US11 proteins, vectors, and host cells comprising such US11 proteins. In yet another embodiment, kits comprising the US11 pharmaceutical compositions are provided.

Methods of producing US11 proteins, polypeptide fragments or variants thereof, for use in the methods disclosed herein may be made in a variety of ways. For example, solid phase synthesis techniques may be used. Suitable techniques are well known in the art, and include those described in Merrifield, in Chem. Polypeptides, pp. 335-61 (Katsoyannis and Panayotis eds. 1973); Merrifield, J. Am. Chem. Soc. 85:2149 (1963); Davis et al., Biochem. Intl. 10:394-414 (1985); Stewart and Young, Solid Phase Peptide Synthesis (1969); U.S. Pat. No. 3,941,763; Finn et al., The Proteins, 3rd ed., vol. 2, pp. 105-253 (1976); and Erickson et al., The Proteins, 3rd ed., vol. 2, pp. 257-527 (1976). Solid phase synthesis is the preferred technique of making individual peptides since it is the most cost-effective method of making small peptides.

The US11 proteins may also be made in transformed host cells using recombinant DNA techniques. To do so, a recombinant DNA molecule coding for the protein is prepared. Methods of preparing such DNA and/or RNA molecules are well known in the art. For instance, sequences coding for the protein could be excised from DNA using suitable restriction enzymes. The relevant sequences can be created using the polymerase chain reaction (PCR) with the inclusion of useful restriction sites for subsequent cloning. Alternatively, the DNA/RNA molecule could be synthesized using chemical synthesis techniques, such as the phosphoramidite method. Also, a combination of these techniques could be used.

Certain embodiments also include a vector encoding US11 in an appropriate host. The vector comprises the DNA molecule that encodes US11 operatively linked to appropriate expression control sequences. Methods of affecting this operative linking, either before or after the polypeptide-encoding DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The resulting vector comprising the protein-encoding DNA molecule is used to transform an appropriate host. This transformation may be performed using methods well known in the art.

Any of a large number of available and well-known host cells may be used in the practice of these embodiments. The selection of a particular host is dependent upon a number of factors recognized by the art. These factors include, for example, compatibility with the chosen expression vector, toxicity to the host cell of the proteins encoded by the DNA molecule, rate of transformation, ease of recovery of the proteins, expression characteristics, bio-safety and costs. A balance of these factors must be struck with the understanding that not all hosts may be equally effective for the expression of a particular DNA sequence.

Next, the transformed host is cultured under conditions so that the desired US11 proteins are expressed. Such conditions are well known in the art. Finally, the proteins are purified from the fermentation culture or from the host cells in which they are expressed. These purification methods are also well known in the art. US11 proteins thereof prepared as described herein may be purified by art-known techniques such as highperformance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification, an antibody, ligand, receptor or antigen can be used to which the US11 protein binds. In addition, size exclusion chromatography can be used to isolate US11 protein.

In a preferred embodiment, a method of producing a US11 protein is provided, wherein the method comprises culturing a host cell comprising a polynucleotide encoding the US11 protein under conditions suitable for expression of the US11 protein, and recovering the US11 protein from the host cell (or host cell culture medium). The purity of the US11 protein can be determined by any of a variety of well-known analytical methods including gel electrophoresis, high pressure liquid chromatography, and the like.

The skilled artisan will readily appreciate that the embodiments are not limited to the US11 sequences depicted herein, but also includes variants of US11. Such variants may contain deletions, substitutions or additions of one or more amino acids in the above depicted amino acid sequence of SEQ ID NO. 1 while maintaining the biological activity of naturally occurring US11 protein. Such variants include those, for example, that increase the half-life or stability of the US11 protein or increase the affinity and binding of US11 protein to the FcRn protein. Such fragments or variants may be naturally occurring or may be synthetically generated, for example, by modifying one or more of the above peptide sequences used in the methods of certain embodiments and evaluating their effects using any of a number of techniques well known in the art.

As used herein, a peptide fragment or variant has amino acid sequences that are at least about 70-75%, typically at least about 80-85%, and most typically at least about 90-95%, 97%, 98% or 99% or more homologous with the US11 protein (SEQ ID NO. 1) or peptide fragments thereof. In certain embodiments, a fragment or variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides of certain embodiments and still obtain a functional molecule that encodes a variant or derivative polypeptide with desirable characteristics.

In a US11 protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. Co., p. 224). One of skill in the art could determine which amino acid residues can be substituted, inserted, or deleted without abolishing biological activity. Assistance can be found using computer programs well known in the art, such as DNASTAR™ software. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

Fragments, or variants, or derivatives of US11 include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and mutants. Truncations or deletions of regions which change functional activity of the proteins are also variants.

Polynucleotides of certain embodiments may be obtained, for example, by solid-state peptide synthesis or using recombinant production. For recombinant production one or more polynucleotides encoding the US11 protein, e.g., as described above, are isolated and inserted into one or more vectors for further cloning and/or expression in a host cell. This polynucleotide may be isolated and sequenced using conventional procedures.

Many vectors are known in the art. Vector components may include one or more of the following: a signal sequence, an origin of replication, one or more selective marker genes (that may, for example, confer antibiotic or other drug resistance, complement auxotrophic deficiencies, or supply critical nutrients not available in the media), an enhancer element, a promoter, and a transcription termination sequence, all of which are well known in the art.

An "expression vector" or "expression construct" as used herein refers to a recombinant DNA molecule containing a desired coding sequence and appropriate nucleic acid control sequences necessary for the expression of the operably linked coding sequence in a particular host cell. An expression vector can include, but is not limited to, sequences that affect or control transcription, translation, and, if introns are present, affect RNA splicing of a coding region operably linked thereto.

Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired. Such techniques are well known in the art. (E.g., Goodey, Andrew R.; et al., Peptide and DNA sequences, U.S. Pat. No. 5,302,697; Weiner et al., Compositions and methods for protein secretion, U.S. Pat. Nos. 6,022,952 and 6,335,178; Uemura et al., Protein expression vector and utilization thereof, U.S. Pat. No. 7,029,909; Ruben et al., 27 human secreted proteins, US 2003/0104400 A1), the contents of which are hereby incorporated by reference.

A "secreted" protein refers to those proteins capable of being directed to the ER, secretory vesicles, or the extracellular space as a result of a secretory signal peptide sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

In one embodiment, a vector, preferably an expression vector, comprising one or more of the polynucleotides encoding the US11 protein of certain embodiments is provided. In other embodiments, the vector is introduced into mammalian cells, e.g., HEK293 cells to produce the US11 protein in supernatant for purification. The resulting US11 protein can then be used in pharmaceutical compositions for used for treatment of antibody-mediated autoimmune or albumin-mediated diseases. In addition, such US11 proteins may be used in vaccine formulations as disclosed below.

Methods are well known to one of skill in the art and can be used to construct expression vectors containing the coding sequence with appropriate transcriptional and translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989).

Typically, the vectors are derived from virus, plasmid, prokaryotic or eukaryotic chromosomal elements, or some combination thereof, and may optionally include at least one origin of replication, at least one site for insertion of heterologous nucleic acid, and at least one selectable marker. Embodiments are also contemplated that express US11 using artificial chromosomes, e.g., bacterial artificial chromosomes (BACs), yeast artificial chromosomes (YACs), mammalian artificial chromosomes (MACs), and human artificial chromosomes (HACs).

In such vectors, typically, a promoter region would be operably associated with a nucleic acid encoding US11 if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. In a preferred embodiment, the promoters are those promoter regions that function in cells that are known to produce autoantibodies, including for example, plasma cells and B-lymphocytes.

A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit a-globin, as well as other sequences capable of controlling gene expression in eukaryotic cells. Additional suitable transcription control regions include tissue-specific promoters and enhancers as well as inducible promoters (e.g. promoters inducible tetracyclines). Such tissue specific promoters include those that function in antibody producing cells such as plasma cells and B-lymphocytes.

The term "host cell" means a cell that has been transformed, or is capable of being transformed, with a nucleic acid and thereby expresses a gene of interest. The polynucleotides encoding the US11 protein for therapeutic use may be expressed in any appropriate host cell, preferably a mammalian cell. The host cell can be prokaryotic (bacteria) or eukaryotic (e.g., yeast, insect, plant and animal cells). A host cell strain may be chosen for its ability to carry out desired post-translational modifications of the expressed protein. Such post-translational modifications of the polypeptide include, but are not limited to, acetylation, carboxylation, glycosylation, phosphorylation, hydroxylation, sulfation, lipidation, and acylation.

Exemplary mammalian host cells are COS1 and COS7 cells, NSO cells, Chinese hamster ovary (CHO) cells, NIH 3T3 cells, HEK293 cells, HEPG2 cells, HeLa cells, L cells, MDCK, W138, murine ES cell lines (e.g., from strains 129/SV, C57/BL6, DBA-1, 129/SVJ), K562, Jurkat cells, BW5147 and any other commercially available human cell lines. Other useful mammalian cell lines are well known and readily available from the American Type Culture Collection (ATCC) (Manassas, Va., USA) and the National Institute of General Medical Sciences (NIGMS) Human Genetic Cell Repository at the Coriell Cell Repositories (Camden, N.J., USA).

In a further aspect, certain embodiments provide pharmaceutical compositions comprising US11 protein or any of the US11 peptide fragments and variants described herein, e.g., for use in any of the therapeutic methods used for treatment of antibody-mediated autoimmune and albumin-mediated diseases. In one embodiment, a pharmaceutical composition comprising a US11 protein and a pharmaceutically acceptable carrier is provided herein. Viral vectors expressing US11 protein may be used for gene therapy or cell therapy of an antibody-mediated autoimmune or albumin-mediated disease. Such vectors may be combined with a pharmaceutically acceptable carrier. In another embodiment, a pharmaceutical composition comprises any of the US11 proteins provided herein and at least one additional therapeutic agent, typically used for treatment of antibody-mediated autoimmune or albumin-mediated disease.

Further provided is a method of producing a US11 protein of certain embodiments in a form suitable for administration in vivo, the method comprising (a) obtaining US11 protein according to various embodiments, and (b) formulating the US11 protein with at least one pharmaceutically acceptable carrier, whereby a preparation of the US11 protein is formulated for administration in vivo.

Further provided is a method of producing a US11 encoding nucleic acid of certain embodiments in a form suitable for administration in vivo, the method comprising (a) obtaining a US11 encoding nucleic acid according to various embodiments, and (b) formulating the US11 encoding nucleic acid with at least one pharmaceutically acceptable carrier, whereby a preparation of the US11 encoding nucleic acid is formulated for administration in vivo.

Pharmaceutical compositions of embodiments comprise a therapeutically effective amount of one or more US11 proteins dissolved or dispersed in a pharmaceutically acceptable carrier. The preparation of a pharmaceutical composition that contains at one or more US11 proteins and optionally an additional active ingredient will be known to those of skill in the art in light of the present disclosure, as exemplified by Remington's Pharmaceutical Sciences, 18th Ed. Mack Printing Company, 1990. For human administration, it will be understood that preparations should meet sterility, pyrogenicity, general safety and purity standards as required by FDA Office of Biological Standards or corresponding authorities in other countries. Preferred compositions are lyophilized formulations or aqueous solutions.

As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it needs to be sterile for such routes of administration as injection. US11 protein of certain embodiments (and any additional therapeutic agent) can be administered by any method or any combination of methods as would be known to one of ordinary skill in the art (see, for example, Remington's Pharmaceutical Sciences, 18th Ed. Mack Printing Company, 1990, incorporated herein by reference). Parenteral administration, in particular intravenous injection, is most commonly used for administering protein or polypeptide molecules such as the US11 protein of certain embodiments. Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Parenteral compositions include those designed for administration by injection, e.g. subcutaneous, intradermal, intra-lesional, intravenous, intra-arterial, intramuscular, intrathecal or intraperitoneal injection. For injection, the US11 protein may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the US11 protein may be in powder form for constitution with a suitable vehicle, e.g., sterile pyrogen-free water, before use. Sterile injectable solutions are prepared by incorporating the US11 protein in the required amount in the appropriate solvent with various other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi.

Pharmaceutical compositions comprising US11 protein may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

US11 protein may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The pharmaceutical preparation of certain embodiments is a liquid composition, e.g. an aqueous solution. For injection purposes, the use of pure water as solvent is preferred. Other solvents which are suitable and conventional for pharmaceutical preparations can, however, also be employed. In a preferred embodiment, the pharmaceutical compositions are isotonic solutions. Further, there is no need for reconstitution at any stage of the preparation of the liquid solution formulation of these embodiments. The solution is a ready-to-use formulation.

The delivery of a therapeutic US11 to appropriate cells can occur via gene therapy ex vivo, in situ, or in vivo by use of any suitable approach known in the art. For example, for in vivo therapy, a nucleic acid encoding the desired US11 protein, either alone or in conjunction with a vector, liposome, or precipitate may be injected directly into the subject, and in some embodiments, may be injected at the site where the expression of the US11 protein is desired. For ex vivo treatment, the subject's cells are removed, the nucleic acid is introduced into these cells, and the modified cells are returned to the subject either directly or, for example, encapsulated within porous membranes which are implanted into the patient. See, e.g. U.S. Pat. Nos. 4,892,538 and 5,283,187.

A variety of techniques are available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, chemical treatments, DEAE-dextran, and calcium phosphate precipitation. Other in vivo nucleic acid transfer techniques include transfection with viral vectors (such as adenovirus, Herpes simplex I virus, adeno-associated virus, lentivirus or retrovirus) and lipid-based systems. The nucleic acid and transfection agent are optionally associated with a microparticle. Exemplary transfection agents include calcium phosphate or calcium chloride co-precipitation, DEAE-dextran-mediated transfection, quaternary ammonium amphiphile DOTMA ((dioleoyloxypropyl) trimethylammonium bromide, commercialized as Lipofectin by GIBCO-BRL)) (Felgner et al, (1987) Proc. Natl. Acad. Sci. USA 84, 7413-7417; Malone et al. (1989) Proc. Natl Acad. Sci. USA 86 6077-6081); lipophilic glutamate diesters with pendent trimethylammonium heads (Ito et al. (1990) Biochem. Biophys. Acta 1023, 124-132); the metabolizable parent lipids such as the cationic lipid dioctadecylamido glycylspermine (DOGS, Transfectam, Promega) and dipalmitoylphosphatidyl ethanolamylspermine (DPPES)(J. P. Behr (1986) Tetrahedron Lett. 27, 5861-5864; J. P. Behr et al. (1989) Proc. Natl. Acad. Sci. USA 86, 6982-6986); metabolizable quaternary ammonium salts (DOTB, N-(1-[2,3-dioleoyloxy]propyl)-N,N,N-trimethylammonium methyl sulfate (DOTAP)(Boehringer Mannheim), polyethyleneimine (PEI), dioleoyl esters, ChoTB, ChoSC, DOSC)(Leventis et al. (1990) Biochim. Inter. 22, 235-241); 3 beta [N—(N', N'-dimethylaminoethane)-carbamoyl]cholesterol (DC-Chol), dioleoylphosphatidyl ethanolamine (DOPE)/3beta [N—(N', N'-dimethylaminoethane)-carbamoyl]cholesterolDC-Chol in one to one mixtures (Gao et al., (1991) Biochim. Biophys. Acta 1065, 8-14), spermine, spermidine, lipopolyamines (Behr et al., Bioconjugate Chem, 1994, 5: 382-389), lipophilic polylysines (LPLL) (Zhou et al., (1991) Biochim. Biophys. Acta 939, 8-18), [[(1, 1, 3, 3-tetramethylbutyl) cre-soxy]ethoxy] ethyl]dimethylbenzylammonium hydroxide (DEBDA hydroxide) with excess phosphatidylcholine/cholesterol (Ballas et al., (1988) Biochim. Biophys. Acta 939, 8-18), cetyltrimethylammonium bromide (CTAB)/DOPE mixtures (Pinnaduwage et al, (1989) Biochim. Biophys. Acta 985, 33-37), lipophilic diester of glutamic acid (TMAG) with DOPE, CTAB, DEBDA, didodecylammonium bromide (DDAB), and stearylamine in admixture with phosphatidylethanolamine (Rose et al., (1991) Biotechnique 10, 520-525), DDAB/DOPE (TransfectACE, GIBCO BRL), and oligogalactose bearing lipids. Exemplary transfection enhancer agents that increase the efficiency of transfer include, for example, DEAE-dextran, polybrene, lysosome-disruptive peptide (Ohmori N I et al, Biochem Biophys Res Commun Jun. 27, 1997; 235(3):726-9), chondroitan-based proteoglycans, sulfated proteoglycans, polyethylenimine, polylysine (Pollard H et al. J Biol Chem, 1998 273 (13): 7507-11), integrin-binding peptide CYGGRGDTP (SEQ ID NO: 10), linear dextran nonasaccharide, glycerol, cholesteryl groups tethered at the 3'-terminal internucleoside link of an oligonucleotide (Letsinger, R. L. 1989 Proc Natl Acad Sci USA 86: (17):6553-6), lysophosphatide, lysophosphatidylcholine, lysophosphatidylethanolamine, and 1-oleo yl lysophosphatidylcholine.

In some situations it may be desirable to deliver the nucleic acid with an agent that directs the nucleic acid-containing vector to target cells. Such "targeting" molecules include antigen binding proteins specific for a cell-surface membrane protein on the target cell, or a ligand for a receptor on the target cell. In a specific embodiment, the targeted cells may be antibody producing cells such as plasma cells or B-lymphocytes. Where liposomes are employed, proteins which bind to a cell-surface membrane protein associated with endocytosis may be used for targeting and/or to facilitate uptake. Examples of such proteins include capsid proteins and fragments thereof tropic for a particular cell type, antigen binding proteins for proteins which undergo internalization in cycling, and proteins that target intracellular localization and enhance intracellular half-life. In other embodiments, receptor-mediated endocytosis can be used. Such methods are described, for example, in Wu et al., 1987 or Wagner et al., 1990. For review of the currently known gene marking and gene therapy protocols, see Anderson 1992. See also WO 93/25673 and the references cited therein. For additional reviews of gene therapy technology, see Friedmann, Science, 244: 1275-1281 (1989); Anderson, Nature, supplement to vol. 392, no 6679, pp. 25-30 (1998); Verma, Scientific American: 68-84 (1990); and Miller, Nature, 357: 455460 (1992).

Any of the S11 proteins, or US11 encoding nucleic acids, provided herein may be used in therapeutic methods described herein. For use in the therapeutic methods described herein, US11 proteins, or US11 encoding nucleic acids, of certain embodiments would be formulated, dosed, and administered in a fashion consistent with good medical practice. Factors for consideration in this context include the particular disorder being treated, the particular subject being treated, the clinical condition of the subject, the cause of the disease or condition, the site of delivery of the agent, the method of administration, the scheduling of administration, and other factors known to medical practitioners or those of skill in the art.

In certain embodiments the method further comprises administering to the individual a therapeutically effective amount of at least one additional therapeutic agent, e.g. an agent that is typically used to treat the antibody-mediated autoimmune and albumin-mediated diseases to be treated. A "subject" or "individual" according to any of the above embodiments is a mammal, preferably a human.

For the treatment of antibody-mediated autoimmune and albumin-mediated diseases, the appropriate dosage of US11 protein (when used alone or in combination with one or more other additional therapeutic agents) will depend on the type of disease to be treated, the route of administration, the body weight of the patient, the severity and course of the disease, whether the US11 protein is administered for preventive or therapeutic purposes, previous or concurrent therapeutic interventions, the patient's clinical history and response to the US11 protein, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The US11 proteins are suitably administered to the patient at one time or over a series of treatments subcutaneously, intravenously, intramuscularly, locally or via airway or under tongue. For repeated administrations over several days or longer, depending on the condition, the treatment would generally be sustained until a desired suppression of disease symptoms occurs.

One typical dosage would be in the range from about 1 μg/kg body weight to 1000 mg/kg body weight. In other non-limiting examples, a dose may also comprise from about 1 μg/kg body weight, about 5 μg/kg body weight, about 10 μg/kg body weight, about 50 μg/kg body weight, about 100 μg/kg body weight, about 200 μg/kg body weight, about 350 μg/kg body weight, about 500 μg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein.

Such doses may be administered intermittently, e.g. every week or every three weeks (e.g. such that the patient receives from about two to about twenty, or e.g. about six doses of the US11 protein). An initial higher loading dose, followed by one or more lower doses may be administered. However, other dosage regimens may be useful. The progress of this therapy is easily monitored by conventional techniques and assays. The US11 proteins of certain embodiments will generally be used in an amount effective to achieve the intended purpose. For use to treat or prevent a disease condition, the US11 protein of these embodiments, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

The US11 containing compositions may be administered by an initial bolus followed by a continuous infusion to maintain therapeutic circulating levels of drug product. As another example, the inventive compound may be administered as a one-time dose. Those of ordinary skill in the art will readily optimize effective dosages and administration regimens as determined by good medical practice and the clinical condition of the individual patient.

Sustained-release preparations may be prepared. Suitable examples of sustained-release preparations include semipermeable matrices of solid hydrophobic polymers containing the immunoglobulin, which matrices are in the form of shaped articles, e.g., films, or microcapsule. Examples of sustained-release matrices include polyesters, hydrogels (for example, poly (2-hydroxyethyl-methacrylate), or poly (vinyl alcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations of other embodiments may be designed to be short-acting, fast-releasing, long-acting, or sustained-releasing as described herein. Thus, the pharmaceutical formulations may also be formulated for controlled release or for slow release.

The attending physician for patients treated with US11 protein of certain embodiments would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

The US11 protein described herein may be administered in combination with one or more other agents or "therapeutic agents" for use in treatment of antibody-mediated autoimmune and albumin-mediated diseases. A US11 protein may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other.

There are a variety of drugs prescribed for patients with antibody-mediated autoimmune and albumin-mediated diseases. It's important for both patients living with such diseases and those who care for them to understand the prescribed medication, to follow the directions of usage, and to be able to recognize the possible side effects associated with the medicine.

In another aspect of the embodiment, an article of manufacture (e.g., a kit) containing materials useful for the treatment of antibody-mediated autoimmune and albumin-mediated diseases as described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle).

The label or package insert indicates that the composition is used for treating the condition of choice. The article of manufacture may comprise (a) a first container with a composition contained therein, wherein the composition comprises US11 protein; and (b) a second container with a composition contained therein, wherein the composition comprises a further therapeutic agent.

Kits in certain embodiments may further comprise a package insert indicating that the compositions can be used to treat a particular condition. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Methods for Prevention and Treatment of HCMV Infection

The present disclosure relates to compositions and methods for prevention and/or treatment of HCMV infections. In one embodiment, such treatments are designed to reduce the expression and/or activity of US11 in infected cells.

In a specific embodiment, compositions are provided comprising nucleic acid molecules designed to target US11 mRNA and inhibit, silence or attenuated the expression of that RNA. Such compositions may be used in methods for prevention or treatment of HCMV infection.

The terms "inhibit," "silencing," and "attenuating" can refer to a measurable reduction in expression of a target mRNA (or the corresponding polypeptide or protein) as compared with the expression of the target mRNA (or the corresponding polypeptide or protein) in the absence of an interfering RNA molecule. The reduction in expression of the target mRNA (or the corresponding polypeptide or protein) is commonly referred to as "knock-down" and is reported relative to levels present following administration or expression of a non-targeting control RNA.

The term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The terms "siRNA" refers to either small interfering RNA, short interfering RNA, or silencing RNA. Generally, siRNA comprises a class of double-stranded RNA molecules, approximately 20-25 nucleotides in length. Most notably, siRNA is involved in RNA interference (RNAi) pathways and/or RNAi-related pathways, wherein the compounds interfere with gene expression.

The term "shRNA" refers to any small hairpin RNA or short hairpin RNA. Although it is not necessary to understand the mechanism of action, it is believed that any sequence of RNA that makes a tight hairpin turn can be used to silence gene expression via RNA interference. Typically, shRNA uses a vector introduced into a cell genome and is constitutively expressed by a compatible promoter. The shRNA hairpin structure may also be cleaved into siRNA, which may then become bound to the RNA-induced silencing complex (RISC). This complex binds to and cleaves mRNAs which match the siRNA that is bound to it.

The term "microRNA" or "miRNA", refers to any single-stranded RNA molecules of approximately 21-23 nucleotides in length, which regulate gene expression. miRNAs may be encoded by genes from whose DNA they are transcribed but miRNAs are not translated into protein (i.e. they are non-coding RNAs). Each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression. T The present disclosure relates to compositions that comprise nucleic acid molecules designed to target US11 mRNA and inhibit, silence or attenuated the expression of that RNA and methods for preparing them. In such instances, the nucleic acid molecules contain a region of nucleotide sequence that can direct the destruction and/or translational inhibition of the targeted US11 transcript. Methods for design and expression of such nucleic acids, e.g., antisense, miRNA, siRNA and shRNA, are well known to those of skill in the art.

In an embodiment, antibodies that bind to the US11 protein may also be used inhibit the activity of the US11 protein in HCMV infected subjects.

In an embodiment, vaccine formulations effective against HCMV, and methods of using the vaccines in the treatment, prevention and prophylaxis of HCMV infections in a subject are provided. The vaccine formulations of the present disclosure comprise full length and/or a portion of the US11 protein and a pharmaceutically acceptable carrier or diluent. The skilled artisan will understand that the number, type, identity and size of the HCMV proteins, or polypeptide fragments that can be included in the vaccine formulations of the present disclosure can vary. One, two, three, four, five, six or more different portions of the US11 protein can be used in the formulations, either in combination with each other (i.e., all peptides in the formulation are derived from US11) or in combination with other peptides and/or polypeptides of HCMV.

Maternal immunity is central to protection of the fetus because infection can occur when neutralizing IgG is low. Because FcRn is important in passive immunity, its inactivation could lead to superinfection of an unprotected developing fetus. Accordingly, the use of US11 inhibitors and vaccines may be advantageously use in the treatment of pregnant females.

As indicated above, the proteins and polypeptide fragments used in the formulations disclosed herein are from HCMV and include at least one US11 polypeptide. When only a portion of a US11 protein is used in a vaccine formulation, the size of the peptide is only limited by its ability to be recognized by the immune system of the subject to which the vaccine is administered. The vaccine formulations of the present disclosure also include the use of peptides and polypeptides having at least about 70%, 75%, 80%, 85%, 90%, 91%, 92%, 93%, 94%, 95%, 96%, 97%, 98% or 99% sequence identity to US11 for use in the vaccine formulations disclosed herein. Sequence identity is determined by aligning the amino acid sequence of two peptides or proteins and calculating the number of amino acid differences over the entire length of the alignment. The skilled artisan will understand that there are a number of commercially available sequence manipulation programs for use in making such calculations, including the website of the National Center for Biotechnology Information.

The proteins and polypeptide fragments used in the vaccine formulations may be obtained through methods described above or any of the many well-established means known in the art. The skilled artisan will understand that the peptides and polypeptides can possess the native glycosylation of polypeptide, or they can lack such glycosylation, or they can have altered glycosylation.

The vaccine formulations may comprise different amounts of the particular peptides and polypeptides from which they are prepared. Further, the total amount of protein in the formulations will vary based on the particular use to which the formulations are put (e.g., administration to the subject pre- or post-exposure to HCMV), the age and size of the subject, and the general health of the subject, to name only a few factors to be considered. In general, however, the vaccine formulations will comprise sufficient US11 protein to induce an immune response in a subject to the components of the vaccine. For example, the vaccines formulations may contain between about 1 to about 1000 µg of total US11 protein per kg of body weight of the subject to which the dose of the vaccine formulation will be administered, more preferably between about 10 to about 200 µg, even more preferably between about 15 to about 100 µg.

The pharmaceutically acceptable carrier, diluent or excipient included in the vaccine formulations will vary based on the identity of the HCMV proteins, including US11, in the formulation, the means used to administer the formulation, the site of administration and the dosing schedule used. Suitable examples of carriers and diluents are well known to those skilled in the art and include water-for-injection, saline, buffered saline, dextrose, water, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, lipospheres, vesicles, particles, and liposomes. The terms specifically exclude cell culture medium. Additional carriers include cornstarch, gelatin, lactose, sucrose, microcrystalline cellulose, kaolin, mannitol, dicalcium phosphate, sodium chloride, alginic acid, croscarmellose sodium, and sodium starch glycolate.

Excipients included in a formulation have different purposes depending, for example on the nature of the vaccine formulation and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweeteners, perfuming agents, flavoring agents, coloring agents, administration aids, and combinations thereof.

Administration of the vaccine formulations may be via any of the means commonly known in the art of vaccine delivery. Such routes include intravenous, intraperitoneal, intramuscular, subcutaneous and intradermal routes of administration, as well as nasal application, by inhalation, ophthalmically, orally, rectally, vaginally, or by any other mode that results in the vaccine formulation contacting mucosal tissues.

As a specific example, intramuscular preparations can be prepared and administered in a pharmaceutically acceptable diluent such as Water-for-Injection, 0.9% saline, or 5% glucose solution. In one embodiment, the vaccine formulations exist as atomized dispersions for delivery by inhalation. The atomized dispersion of the vaccine formulation typically contains carriers common for atomized or aerosolized dispersions, such as buffered saline and/or other compounds well known to those of skill in the art. The delivery of the vaccine formulations via inhalation has the effect of rapidly dispersing the vaccine formulation to a large area of mucosal tissues as well as quick absorption by the blood for circulation. One example of a method of preparing an atomized dispersion is described in U.S. Pat. No. 6,187,344, entitled, "Powdered Pharmaceutical Formulations Having Improved Dispersibility," which is hereby incorporated by reference in its entirety.

Additionally, the vaccines and vaccine formulations may also be administered in a liquid form. When the vaccine formulation is formulated as a liquid, the liquid can be either a solution or a suspension of the vaccine formulation. There are a variety of suitable formulations for the solution or suspension of the vaccine formulation that are well known to those of skill in the art, depending on the intended use thereof. Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

The vaccine formulations of the present disclosure may also include an adjuvant. Suitable adjuvants include Freund's Complete and Incomplete Adjuvant, Titermax, Oil in Water Adjuvants, as well as Aluminum compounds where antigens, normally proteins, are physically precipitated with hydrated insoluble salts of aluminum hydroxide or aluminum phosphate. Other adjuvants include liposome-type adjuvants comprising spheres having phospholipid bilayers that form an aqueous compartment containing the vaccine candidate and protecting it from rapid degradation, and that provide a depot effect for sustained release. Surface active agents may also be used as adjuvants and include lipoteichoic acid of gram-positive organisms, lipid A, and TDM. Quil A and QS-21 (saponin-type adjuvants), monophosphoryl lipid A, and lipophilic MDP derivatives are suitable adjuvants that have hydrophilic and hydrophobic domains from which their surface-active properties arise. Compounds normally found in the body such as vitamin A and E, and lysolecithin may also be used as surface-active agents. Other classes of adjuvants include glycan analog, coenzyme Q, amphotericin B, dimethyldioctadecylammonium bromide (DDA), levamisole, and benzimidazole compounds. The immunostimulation provided by a surface active agent may also be accomplished by either developing a US11 protein with non-active portions of the cholera toxin, exotoxin A, or the heat labile toxin from *E. coli*. Immunomodulation through the use of anti-IL-17, anti IFNγ, anti-IL-12, IL-2, IL-10, or IL-4 may also be used to promote a strong Th2 or antibody mediated response to the vaccine formulation.

The present disclosure is also directed to methods of generating an immune response in a subject to a vaccine formulation disclosed herein. In one embodiment, the present disclosure is directed to methods of generating an immune response in a subject, comprising administering an immunologically effective amount of a vaccine formulation of the present disclosure to a subject, thereby generating an immune response in a subject. In each of the methods of generating an immune response of the present disclosure, the immune response is preferably a protective immune response.

An “immunologically effective amount” of a vaccine formulation is one that is sufficient to induce an immune response to vaccine components in the subject to which the vaccine formulation is administered. A “protective immune response” is one that confers on the subject to which the vaccine formulation is administered protective immunity against the HCMV from which the proteins of the formulation were obtained. The protective immunity may be partial or complete immunity.

The vaccine formulations of the present disclosure may also be used in methods of inhibiting a HCMV infection in a subject. Such methods comprise administering a therapeutically effective amount of a vaccine formulation of the present disclosure to a subject at risk of developing a HCMV infection, thereby inhibiting a HCMV infection in a subject. In a preferred embodiment, the method further comprises administering an antiviral agent to the subject at risk of developing a HCMV infection in conjunction with the administration of the vaccine formulation.

A “therapeutically effective amount” of a vaccine formulation is one that is sufficient to provide at least some reduction in the symptoms of a HCMV infection in a subject to which the vaccine formulation is administered.

As used herein, the terms “inhibit”, “inhibiting” and “inhibition” have their ordinary and customary meanings and include one or more of inhibiting HCMV. Such inhibition is an inhibition of about 1% to about 100% versus a subject to which the vaccine formulation has not been administered (with or without the additional administration of the antiviral agent). Preferably, the inhibition is an inhibition of 100%, 99%, 98%, 97%, 96%, 95%, 90%, 80%, 70%, 60%, 50%, 40%, 30%, 20%, 10%, 5% or 1%. As used herein, the inhibition lasts at least a period of days, weeks, months or years upon completing of the dosing schedule. Preferably the inhibition is for the lifespan of the subject.

The present disclosure is also directed to methods for providing prophylaxis of a HCMV infection in a subject using the vaccine formulations of the present disclosure. In one embodiment, the present disclosure is directed to methods for providing prophylaxis of a HCMV infection in a subject, comprising administering a therapeutically effective amount of a vaccine formulation of the present disclosure to a subject having a HCMV infection, thereby providing prophylaxis of a HCMV infection in a subject. In a preferred embodiment, the method further comprises administering an antiviral agent to the subject having a HCMV infection in conjunction with the administration of the vaccine formulation.

As used herein, “prophylaxis” includes inhibiting the development of a productive or progressive infection by HCMV in a subject, where the prophylaxis lasts at least 1, 5, 10, 15, 20, 25, 30, 35, 40, 45, 50, 55, 60, or more days after administration of a vaccine formulation the present disclosure (with or without the additional administration of the antimicrobial agent). Inhibition against development of a productive or progressive infection by HCMV means that the severity of a HCMV infection in a subject is reduced by about 1% to about 100% versus a subject to which a vaccine formulation of the present disclosure has not been administered (with or without the additional administration of the antiviral agent). Preferably, the reduction in severity is a 100%, 99%, 98%, 97%, 96%, 95%, 90%, 80%, 70%, 60%, 50%, 40%, 30%, 20%, 10%, 5% or 1% reduction in severity. The severity of an infection may be based on the amount of HCMV present in a subject, the length of time that HCMV can be detected in a subject, and/or the severity of a symptom of HCMV infection, among other factors.

The present disclosure is also directed to methods of treating a HCMV infection in a subject using the vaccine formulations of the present disclosure. In one embodiment, the present disclosure is directed to methods of treating a HCMV infection in a subject, comprising administering a therapeutically effective amount of a vaccine formulation of the present disclosure to a subject having a HCMV infection, thereby treating a HCMV infection in a subject. In a preferred embodiment, the method further comprises administering an antiviral agent to the subject having a HCMV infection in conjunction with the administration of the vaccine formulation.

As used herein, the terms “treating” and “treatment” have their ordinary and customary meanings, and include one or more of, ameliorating a symptom of a HCMV infection in a subject, blocking or ameliorating a recurrence of a symptom of a HCMV infection in a subject, decreasing in severity and/or frequency a symptom of a HCMV infection in a subject, as stasis, decreasing, or inhibiting replication of HCMV in a subject. Treatment means ameliorating, blocking, reducing, decreasing or inhibiting by about 1% to about 100% versus a subject to which the vaccine formulation of the present disclosure has not been administered (with or without the additional administration of the antiviral agent). Preferably, the ameliorating, blocking, reducing, decreasing or inhibiting is 100%, 99%, 98%, 97%, 96%, 95%, 90%, 80%, 70%, 60%, 50%, 40%, 30%, 20%, 10%, 5% or 1%. The treatment may begin prior to, concurrent with, or after the onset of clinical symptoms of the infection. The results of the treatment may be permanent, such as where the HCMV infection is completely cleared from the subject, or may be for a period of days (such as 1, 2, 3, 4, 5, 6 or 7 days), weeks (such as 1, 2, 3 or 4 weeks) or months (such as 1, 2, 3, 4, 5, 6 or more months).

When an antiviral agent is included in the methods of the present disclosure the antiviral agent may be administered prior to, concurrent with or after the vaccine formulation is administered to the subject. Where the antiviral agent is administered prior to or after the vaccine formulation, the period of time between when the antiviral agent and the vaccine formulation are administered may be a period of hours (such as 6, 12, 18 or 24 hours), days (such as 1, 2, 3, 4, 5, 6 or 7 days), weeks (such as 1, 2, 3 or 4 weeks) or months (such as 1, 2, 3, 4, 5, 6 or more months). The antiviral agent may be any that is effective in the treatment of a HCMV infection and may include, but is not limited to, ganciclovir, valganciclovir, cidofovir and foscarnet).

In each of the methods of the present disclosure the vaccine formulations are administered in a pharmaceutically acceptable form and in substantially non-toxic quantities. The vaccine formulations may be administered to a subject using different dosing schedules, depending on the particular use to which the formulations are put (e.g., administration to the subject pre- or post-exposure to HCMV), the age and size of the subject, and the general health of the subject, to name only a few factors to be considered. In general, the vaccine formulations may be administered once, or twice, three times, four times, five times, six times or more, over a dosing schedule. The timing between each dose in a dosing schedule may range between a few hours, six, 12, or 18 hours, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more days. The same quantity of protein in the formulation may be administered in each dose of the dosing schedule, or the amounts in each dose may vary. The identity of the particular peptides and polypeptides in the formulation may also vary or remain the same in each dose in a dosing schedule.

In another aspect of the embodiment, an article of manufacture (e.g., a kit) containing materials useful for the treatment or prevention of HCMV infection as described above is provided. In an embodiment, the kit comprises the necessary components of a vaccine formulation that elicits an immune response to HCMV and instructions for its use is also provided herein.

The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, and/or preventing HCMV infection and may have a sterile access port (for example the container may be an intravenous solution bag or a vial having a stopper pierceable by a hypodermic injection needle).

The label or package insert indicates that the composition is used for treating or preventing the HCMV infection. The article of manufacture may comprise (a) a first container with a composition contained therein, wherein the composition comprises a US11 protein; and (b) a second container with a composition contained therein, wherein the composition comprises a further therapeutic agent.

Kits in certain embodiments may further comprise a package insert indicating that the compositions can be used to treat a particular condition. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that the examples and embodiments described herein are for illustrative purposes only and that various modifications or changes in light thereof will be suggested to persons skilled in the art and are to be included within the spirit and purview of this application and scope of the appended claims.

All documents, papers and published materials referenced herein, including books, journal articles, manuals, patent applications, published patent applications and patents, are expressly incorporated herein by reference in their entireties.

EXAMPLES

Material and Methods
Cell Lines, Antibodies, Enzymes, and Viruses

Human intestinal epithelial Caco-2, human placental trophoblast BeWo, human lung fibroblast MRC-5, cervical HeLa cell lines were obtained from the American Type Culture Collection (ATCC, Manassas, Va.) and grown in complete DMEM. The human endothelial cell line HMEC-1, a dermal-derived microvasculature cell line, was provided by the Centers for Disease Control (Atlanta, GA). Human monocytic THP-1 cells (ATCC) and HMEC-1 cells were grown in RPMI 1640 (Invitrogen, Carlsbad, CA) complete medium. Complete media were supplemented with 10 mM HEPES, 10% FCS (Sigma-Aldrich, St. Louis, MO), 1% L-glutamine, nonessential amino acids, and 1% penicillin-streptomycin. To differentiate THP-1 cells into macrophages, cells were treated with 50 ng/ml phorbol-12-myristate-13-acetate (PMA) for 48 hrs. Primary human umbilical vein endothelial cells (HUVEC, ATCC PCS-100-013™) were purchased from ATCC and grown in vascular cell basal medium (PCS-100-030™) supplemented with endothelial cell growth kit-BBE (PCS-100-040™). Cells were grown in 5% $CO_2$ at 37° C.

Rabbit, mouse, or rat anti-FLAG epitope (DYKDDDDK) (SEQ ID NO: 3) was purchased from Sigma-Aldrich and BioLegend. The hybridoma 12CA5 and the clone 3F10, both of which react with the influenza hemagglutinin (HA, YPYDVPDYA) (SEQ ID NO: 4) epitope, were purchased from ATCC and Roche. Rabbit anti-Myc (EQKLISEEDL) (SEQ ID NO: 5) Ab and mouse anti-Myc $IgG_{2a}$ (clone 9B11) were from Cell Signaling. Mouse anti-human FcRn $IgG_{2a}$ (clone B-8), mouse anti-ubiquitin $IgG_1$ (clone P4D1), and rabbit anti-TfR1 Abs were from Santa Cruz. Mouse anti-$\beta_2$m hybridoma (BBM1) was purchased from ATCC. Rabbit anti-β-tubulin Ab was purchased from Sigma-Aldrich. Affinity-purified polyclonal Ab against the cytoplasmic tail of human FcRn was described previously (52). Affinity-purified polyclonal Ab against US11 was produced in mice as described below. Rabbit anti-TMEM129 polyclonal Ab was purchased from Sigma-Aldrich. Mouse anti-MHC class I (clone W6/32) Ab was from Enzo Life Sciences (East Farmingdale, NY). Mouse anti-early endosomal Ag-1 (EEA1) and mouse anti-LAMP-1 were obtained from BD Biosciences (San Jose, CA). Mouse anti-HCMV pp65 IgG2a Ab and rabbit anti-$\beta_2$m Ab were was purchased from Abcam (Cambridge, UK). HRP-conjugated goat anti-mouse, rabbit, rat or human IgG Fc secondary Ab were purchased from Southern Biotech (Birmingham, AL) or from Bethyl (Hamburg, Germany). Alexa Fluor 488-, Alexa Fluor 555-, and Alexa Fluor 633-conjugated secondary Abs were purchased from Life Technologies (Carlsbad, CA.).

The HCMV AD169 strain was purchased from ATCC. An HCMV clinical strain, designated for CMV Bethesda BAL, was isolated from bronchoalveolar lavage fluid in a patient who signed consent on an Institution Review Board approved protocol (014-0161) at the National Institute of Allergy and Infectious Diseases, National of Institutes of Health, Bethesda, MD. The virus was passaged less than 5 times in MRC-5 cells before use in these experiments. 10-14 days post-infection, cell-free virus was harvested by sonicating cell pellets, and the cellular debris was removed by centrifugation at 6,000 relative centrifugal force (rcf) for 20 min. Virus was concentrated by centrifugation at 20,000 rcf for 2 hr through a 20% sucrose cushion. Virus titer was determined by quantifying $TCID_{50}$ in MRC-5 (ATCC) cells using the Reed-Muench method. The US11 gene of the CMV Bethesda BAL was sequenced and the sequence is available in the Genbank with an accession number MK647994.

Viral Infection of Human HeLa, THP-1, HMEC-1, BeWo, Caco-2, and Primary HUVEC Cells HeLa, THP-1, HMEC-1, BeWo, primary HUVEC, and Caco-2 cell monolayers were infected with the HCMV clinical strain through the addition of virus at a high MOI of 5 or 10. Prior to infection, cells were washed once with Dulbecco's phosphate-buffered saline (PBS). After the addition of virus, infection proceeded for 2 hr at 37° C. in an atmosphere of 5% $CO_2$. After washing three times with DPBS, infected cells were cultured with fresh complete medium at 37° C. in an atmosphere of 5% $CO_2$.

Construction of Protein Expression Vectors and Site-Directed Mutagenesis of US11

All primers used for cloning or mutagenizing the genes in this study are summarized (Table 1).

The construction of human $\beta_2 m$ and FcRn expression plasmids, pcDNA$\beta_2 m$, and pcDNA-FLAGFcRn was previously described (50). HLA-$A_2$cDNA was amplified from HeLa total RNA by RT-PCR and was cloned into pcDNA-Flag via Hind III and Xba I restriction site cloning. Homeostatic iron regulator (HFE) encoding the human hemochromatosis protein was amplified from pCMV-Sport-HFE and cloned into pcDNA-Flag using Hind III and Xba I restriction site cloning. An FcRn mutant without the cytoplasmic tail, FcRn CT–/–, or FcRn mutant deleted for amino acid 365 in its C-terminus, FcRn 365A–/–, were amplified from pcDNA-FLAGFcRn and subsequently cloned into pcDNA-Flag using Not I and Xba I double digestions. To construct pSectag2-Derlin-1, Derlin-1 was amplified from HeLa cDNA and its C-terminus was fused to a Myc epitope. The DNA fragment was digested with Xba I and Xho I (underlined) and ligated into the plasmid pSectag2, which was pre-digested with Nhe I (isocaudomer of Xba I) and Xho I enzymes. A Derlin-1 mutant deleted for amino acids 1-66 in its N-terminus (NT–/–) or deleted for amino acids 526-756 in its C-terminus (CT–/–) was amplified from pSectag2-Derlin-1 and subsequently cloned into pSecTag Hygro A plasmid using Xba I and Xho I double digestions. The pTFR1-GFP plasmid was a gift from Dr. Gary Banker (Oregon Health and Science University, Portland, OR).

The purified HCMV AD169 DNA was only used as a template for synthesis of HCMV genes, US11 or US2. In brief, the pEF6-US11 and pEF6-US2 constructs were constructed by fusing an HA epitope to the N-terminus of either HCMV US11 or the C-terminus US2 gene by the PCR primer pairs listed in Table 1. The N-terminal HA tag was inserted between the US11 signal peptide and the US11 ORF. All DNA fragments were digested with BamH I and Xba I (underlined) and ligated into the plasmid pEF6 to generate the plasmid pEF6-US11 or pEF6-US2. A US11 mutant was generated by mutation of a polar amino acid, glutamine (Q) 192, within the US11 transmembrane domain to a hydrophobic leucine (L) residue using a site-directed mutagenesis kit (Takara, Mountain View, CA). The US11 DNA in the pEF6 expression vector was used as a template. The oligonucleotide was used for the change of a glutamine (Q) 192 to a leucine (L) residue, base substitutions are underlined. The resultant plasmids were designed for pcDNAUS11Q192L. To construct a pGex4T1-US11, a PCR primer pair was used to amplify a truncated 438 bp DNA fragment encoding the extracellular domain of US11 gene. In the above cloning, the primer introduced a BamH I or Not I site (underlined) to facilitate subcloning of the DNA fragment into the pGEX4T-1 (Amersham Pharmacia Biotech, Piscataway, NJ) expression vector. All constructs were sequenced to verify the fidelity of amplification, cloning, and mutations. All oligonucleotides used in this study are summarized (Table 1).

Production of Affinity-Purified FcRn- and US11-Specific Ab

Production of affinity-purified FcRn-specific Abs was previously described (52). Production of affinity-purified glutathione S-transferase (GST) HCMV US11 protein was done as previously described (52). In brief, recombinant GST-US11 proteins were produced in BL21 cells (Invitrogen) following treatment with 0.2 mM IPTG (isopropyl-β-D-thiogalactopyranoside) for 16 hr. To produce anti-US11 antibodies, we immunized a mouse with the purified GST-US11 HCMV US11 protein and Freund's adjuvant. Anti-US11 antibodies were then affinity purified from the immunized mouse sera. The animal experiment was approved by the University of Maryland Institutional Animal Care and Use Committee.

Semi-Quantitative RT-PCR Analysis

Semiquantitative RT-PCR was performed according to the manufacturer's instructions. In brief, Caco-2 cells ($5\times10^5$) were infected with HCMV (MOI 5) or mock-infected for 48 hr, and then cells were treated with CHX (100 µg/ml) from 30 to 240 min. Total RNA was isolated using TRIzol (Invitrogen). First-strand cDNAs were obtained from total RNA (100 ng) using a SuperScript™ III Reverse Transcriptase kit (ThermoScientific). Then the cDNAs were used as the template for PCR amplification by human FcRn (5'-GTACCTGAGCTACAATAGCCTG-3' (SEQ ID NO: 6), 5'-CACGGAAAAGCCAGGGCTGCTG-3' (SEQ ID NO: 7) or GAPDH (5'-TGGCGTCTTCACCACCATGGAG-3' (SEQ ID NO: 8), 5'-AGTTGTCATGGATGACCTTGGCC-3' (SEQ ID NO: 9)) specific primers. 29 or 34 cycles of PCR amplification were performed in a 20-µl volume. Each cycle consisted of denaturation at 94° C. for 30 s, annealing at 58° C. for 30 s, and extension at 72° C. for 30 s. An additional 10 min was applied for the final extension. PCR products were resolved on 1.5% agarose gels and visualized by staining with ethidium bromide. Integrated density values for the FcRn bands were normalized to the GAPDH values to yield a semiquantitative assessment by densitometric intensity analyses.

Transfection and Protein Expression

The stable cell line, HeLa$^{FcRn}$, has been described previously (50). HeLa, HeLa$^{FcRn}$ and Caco-2 cells were transfected with either empty vector or the recombinant plasmid along with PolyJet transfection reagent (SignaGen Laboratories, Rockville, MD). Single transfectants were selected with G418 (1 mg/ml). Double transfectants were selected with G418 plus either Blasticidin (5 µg/ml) or Hygromycin B (200 µg/ml). Positive clones were tested for protein expression with Western blot using anti-FLAG, anti-HA, and anti-Myc antibodies. Successful transfectants were maintained in complete DMEM medium containing G418 (400 μg/ml) Blasticidin (3 μg/ml). For transient transfections, cells were transfected with 2 μg of plasmids. The level of protein expression was examined 48 hr post-transfection by Western blot. All transfected cells used in this study are summarized (Table 2).

Silencing of the US11, TREM129, and Ube2j Gene Expression by siRNA

Pre-designed siRNA products were synthesized from Genewiz (South Plainfield, NJ), including HCMV US11, human TREM129, and Ube2j1 or Ube2j2 (Table 3). Transfection of siRNA oligonucleotides corresponding to US11, TREM129, or Ube2j genes was carried out using Lipofectamine 2000 transfection agent (Invitrogen) at a final concentration of 20 nM mixed siRNA oligomers per well. Mock control was transfected without adding the mixed siRNA oligomers. The US11 and TMEM129 genes were targeted with two non-overlapping siRNAs to enhance effectiveness. For US11 knockdown in primary HUVEC cells by siRNA, cells were transfected with 20 nM siRNA oligomers per well using Nucleofection kit V (Lonza) 24 hrs before HCMV infection. Knockdown efficiency was confirmed by Western blot.

IgG Binding Assay

A human IgG binding assay was performed as previously described (50). Cells were lysed in PBS (pH 6.0 or 7.4) with 0.5% CHAPS (Sigma-Aldrich) and protease inhibitor cocktail (Calbiochem) mixture on ice for 1-2 hr. The soluble proteins (0.5-1 mg) were incubated with human IgG-Sepharose (Rockland Immunochemicals, Pottstown, PA) at 4° C. overnight. Unbound proteins were washed off with PBS (pH 6.0 or 7.4) containing 0.5% CHAPS. Adsorbed proteins were boiled with Laemmli Sample buffer at 95° C. for 5 min. The soluble fractions were subjected to Western blot analysis as described below.

Immunoprecipitation, Gel Electrophoresis, Western Blotting

Cell lines, transfectants, or HCMV- or mock-infected cells ($5 \times 10^6$) were lysed in PBS with 0.5% CHAPS and protease inhibitor cocktail III (Roche, Branchburg, NJ). The cell lysates were centrifuged at 6000 rpm at 4° C. to remove cell debris. Protein concentrations were determined by the Bradford method (Bio-Rad Laboratories). Immunoprecipitations were performed, as described previously (53). The cell lysates (400 μl) were incubated with 100 μl of a protein G agarose slurry plus 5 μg of primary Abs specific for each protein at room temperature for 2 hrs. The protein G beads were washed by 0.5% CHAPS buffer five times.

The cell lysates or the protein G beads were boiled with 2× Laemmli sample buffer at 95° C. and resolved on a 12% SDS-PAGE gel under reducing conditions. Proteins were transferred onto a nitrocellulose membrane (Schleicher & Schuell, Keene, NH) by semi-dry transfer (Bio-Rad Laboratories, Hercules, CA). All blocking, incubation and washing were performed in 5% non-fat milk and 0.05% Tween 20 in PBS. The membranes were blocked, probed separately with a specific primary Ab, washed, and then probed with an HRP-conjugated secondary Ab for 2 hr. Proteins were visualized using Immobilon Western Chemiluminescent HRP Substrate (Millpore, Billerica, MA). Chemiluminescence signal acquisition and densitometry analysis were conducted using the Image Lab, version 5.2 in a Chemi-Doc XRS imaging system (Bio-Rad Laboratories, Hercules, CA).

Analysis of N-Linked Glycosylation

N-linked glycosylation was analyzed as described previously (53). In brief, native FcRn in cell lysates or the proteins immunoprecipitated by HA murine antibodies were digested with endo-β-N-acetylglucosaminidase H (Endo H; New England Biolabs) in digestion buffer (100 mM sodium acetate, pH 5, 150 mM NaCl, 1% Triton X-100, 0.2% SDS, 0.5 mM PMSF) or with peptide: N-glycosidase F (PNGase F; New England Biolabs) in 50 mM sodium phosphate, pH 7.5, with 1% NP-40. A mock digestion without enzymes was performed as a control. All digestions were performed for 2 hr at 37° C. Proteins were analyzed on a 12% SDS-PAGE gel under reducing conditions and immunoblotted as previously described.

Cell Fractionation

Cell Fractionation was done as the previously described (85). After HeLa$^{FcRn}$ and HeLa$^{FcRn+us11}$ cells were incubated with or without MG132 (50 μM) at 37° C. for 4 hr, cells were then pelleted and lysed by three freeze—thaw cycles. Membrane fractions were pelleted from supernatants by ultracentrifugation at 100,000×g (Beckman XL80, 28700 rpm) for 2 hr. Soluble (cytosolic) fractions were collected and diluted in 1% Triton X-100. Pellet (membrane) fractions were washed by PBS and resuspend in 1% Triton X-100 for further analysis.

Confocal Immunofluorescence

Immunofluorescence was performed as previously described (52). Briefly, cells were cultured on coverslips for 24 hr at 37° C. Subsequent procedures were done at room temperature. The cells were rinsed in PBS, fixed in cold 4% paraformaldehyde (Sigma-Aldrich) in PBS for 20 min, and quenched with glycine for 10 min. After two washes with PBS, the coverslips were permeabilized in solution (PBS containing 0.2% Triton X-100) for 5 min and then blocked with blocking buffer containing 3% normal goat serum (NGS) for 30 min. Antibodies diluted in blocking buffer were added onto the coverslips and incubated for 1 hr. Cells were then incubated with Alexa Fluor 488 or 555-conjugated goat secondary antibodies in blocking buffer. Cell nuclei were stained with DAPI (4', 6-Diamidino-2-Phenylindole, Dihydrochloride) for 15 mins. After each step, cells were washed three times with 0.1% Tween 20 in PBS. Coverslips were mounted on slides using the ProLong antifade kit (Molecular Probes) and examined using a Zeiss LSM 510 confocal fluorescence microscope. Images were processed using LSM Image Examiner software (Zeiss, Thornwood, NY). Quantitative colocalization measurements were performed using Zeiss LSM 510 Examiner Software. Pearson's correlation coefficient was calculated for describing the co-localization correlation of the intensity distributions between two channels, as previously described (86). In each quantitative experiment with the transfected HeLa or infected HMEC-1 cells, 100 representative cells were analyzed. A value of $p<0.05$ was considered significant.

Quantitative Cycloheximide (CHX) Chase Assay

Cells were treated with CHX (100 μg/ml) (Calbiochem, San Diego, CA) for different time periods, lysed, and protein levels were measured by Bradford assay. Each cell lysate (20 μg) was analyzed by Western blotting with corresponding antibodies. The levels of remaining FcRn, HLA-A2, and β2m at different time points were calculated as the percentage of β-tubulin (an internal control). The percentage of time point 0 (min) was assigned a value of 100% and the values from other time points were normalized to this value. The expression levels of proteins were quantified by the band density (relative band volume) measured by software Image Lab 5.2. The degradation experiments were repeated in triplicate.

Flow Cytometry

Surface and intracellular expressions of FcRn were examined in either fixed or permeabilized HeLa transfected, THP-1 cells, or HMEC-1 cells by flow cytometry. Cells were washed with PBS, and if necessary, detached by 10% EDTA. For cell surface staining, after blocking by 2% FBS, cells were incubated with rat anti-FLAG Ab for 1 hr on ice to minimize internalization. For intracellular staining, cells, were first treated with cycloheximide (100 µg/ml) or left untreated as a control for 4 hrs. Subsequently, they were incubated with Fixing/Permealizing Buffer (BD CytoFix/ CytoPer Kit) for 20 min. THP-1 cells were also treated with 30 µg/ml human Fc block (BD) for 10 mins at room temperature. After washing and blocking with 2% FBS, cells were incubated with anti-FLAG Ab or anti-FcRn Ab for 1 hr on ice. For all staining, cells were incubated with isotype-matched control rat Abs to determine the background fluorescence. After washing with PBS, the cells were incubated with Alexa Fluor 488-conjugated secondary Abs for 1 hr on ice. Cells were fixed with 2% paraformaldehyde overnight and analyzed using a FACSAria (Becton Dickinson, Franklin Lakes, NJ) and FlowJo software (Tree Star).

Detection of Protein Ubiquitination in Cultured Cells

Cultured cells were transfected with plasmids expressing US11 along with a FLAG-tagged version of FcRn, HFE, and HLA-A2. 48 hr later, cells were treated with 50 µM MG132 (Calbiochem) for 2 hr and subsequently lysed in PBS with 0.5% CHAPS and protease inhibitor cocktail. The proteins (500-1000 µg) were incubated with anti-FLAG murine Ab and protein G beads overnight at 4° C. After the immunoprecipitates were washed three times with PBS containing 0.05% Tween 20 (PBST), they were heated with Laemmli sample buffer at 95° C. and the eluted products were further analyzed by SDS-PAGE and Western blot analysis to detect ubiquitin and the targeted proteins with respective antibodies.

Enzyme-Linked Immunosorbent Assay (ELISA)

Human IgG was quantified using an ELISA kit (Bethyl Laboratories, Montgomery, TX). ELISA plates (Nalge Nunc, Rochester, NY) were coated with goat anti-human IgG-Fc Ab (10 µg/ml) overnight at 4° C. Plates were washed three times with PBST and then blocked with 2% FBS in PBS for 1 hr at room temperature. Plates were washed with PBST three times and incubated with either an IgG standard or the transcytosis samples diluted in 2% FBS for 2 hr at 25° C. Plates were washed for five times with PBST and incubated with HRP-conjugated goat anti-human IgG-Fc Ab (0.1 µg/ml) for 1 hr. After plates were washed with PBST seven times, tetramethylbenzidine and hydrogen peroxide were added to initiate the colorimetric reaction; 100 µl of 1M sulfuric acid was added to stop the reaction. The colorimetric reaction was read at 450 nm using a Victor III microplate reader (Perkin Elmer, Bridgeville, PA).

In Vitro Human IgG Transcytosis

IgG transcytosis was performed as previously described (39-41). BeWo cells, Caco-2 cells or Caco-2 cells transfected with either pEF6 alone or pEF6-US11 were grown on 0.4 µm Transwell filter inserts (Corning Costar, Corning, NY) to form a monolayer that exhibited a transepithelial electrical resistance (TEER) of 600 ohms/cm² for Caco-2 cells and 400 ohms/cm2 for BeWo cells, measured using planar electrodes (World Precision Instruments, Sarasota, FL). Prior to infection, Caco-2 or BeWo cell monolayers were washed twice with PBS and then were mock-infected or infected with the HCMV clinical strain at an MOI of 10 for 2 hr. After washing, cells were incubated for 48 hr at 37° C. in an atmosphere of 5% $CO_2$. TEER was assessed immediately after adding fresh complete medium to verify that monolayers had remained intact during the infection procedure. Human IgG was added to the apical surface of the cells at a final concentration of 0.5 mg/ml (Caco-2 cells) or 0.25 mg/ml (BeWo cells) and monolayers were incubated for 2 hr at either 4° C. or 37° C. For detecting human IgG, an aliquot of the basolateral medium was concentrated using a 0.5 ml Amicon Ultra 10K centrifugal filter (Millipore, Billerica MA). ELISA was used to quantify human IgG according to the manufacturer's instructions (Bethyl Laboratories, Montgomery, TX). Transported IgG proteins were analyzed by Western blot-ECL or ELISA.

In Vitro Human IgG Protection

Human IgG protection assay was performed in either HEMC-1 cells ($2.5 \times 10^5$/ml) or HeLa$^{FcRn+US11}$, HeLa$^{FcRn}$, and HeLa cells ($10^6$) that were cultured in complete medium containing 5% FBS with ultra-low IgG. After cells were infected with HCMV at an MOI of 5 or control for 48 hr, they were incubated with 50 µg/ml of IgG for additional 48 hrs. The supernatant (50 µl) was subsequently sampled at 0, 12, 24, 36, and 48 hrs and stored at 4° C. for ELISA. To visualize IgG trafficking inside infected HEMC-1 cells ($5 \times 10^4$), we infected them with HCMV at an MOI of 5 for 48 hr and then incubated them with 250 µg/ml IgG for 1 hr at 37° C. To visualize IgG trafficking inside US11$^+$ cells, HeLa$^{FcRn+US11}$ and HeLa$^{FcRn}$ cells were also incubated with 250 µg/ml IgG for 1 hr at 37° C. After washing, cells were incubated for an additional 1 hr in complete medium containing 5% FBS with ultra-low IgG, and then fixed and stained by immunofluorescence for co-localization of IgG with the early endosomal marker EEA1 or lysosomal marker LAMP1. For Pearson's correlation coefficient measurement, 10 microscopic fields, each of which contained at least 10 cells, were measured for correlation coefficiency rate. Statistics The differences between groups were tested by Student's t-test with a significance level of 0.05. Data are expressed as mean±SD.

Results

HCMV Glycoprotein US11 Interacts with FcRn

Genes encoding HCMV proteins, US2, US3, US6, US10, US11, UL16, and UL18 were cloned by PCR amplification of viral DNA. Probing was then done for interactions between FcRn and each individual HCMV protein. HeLa$^{FcRn}$ cells were transfected with plasmids encoding each of the HA-tagged HCMV cDNAs. It was found US6, US11, and UL16 interacted with FcRn. Due to its strong binding to FcRn and affecting FcRn stability, the US11 and FcRn interaction was characterized in this study.

Figures 10A, 10B, 10C:
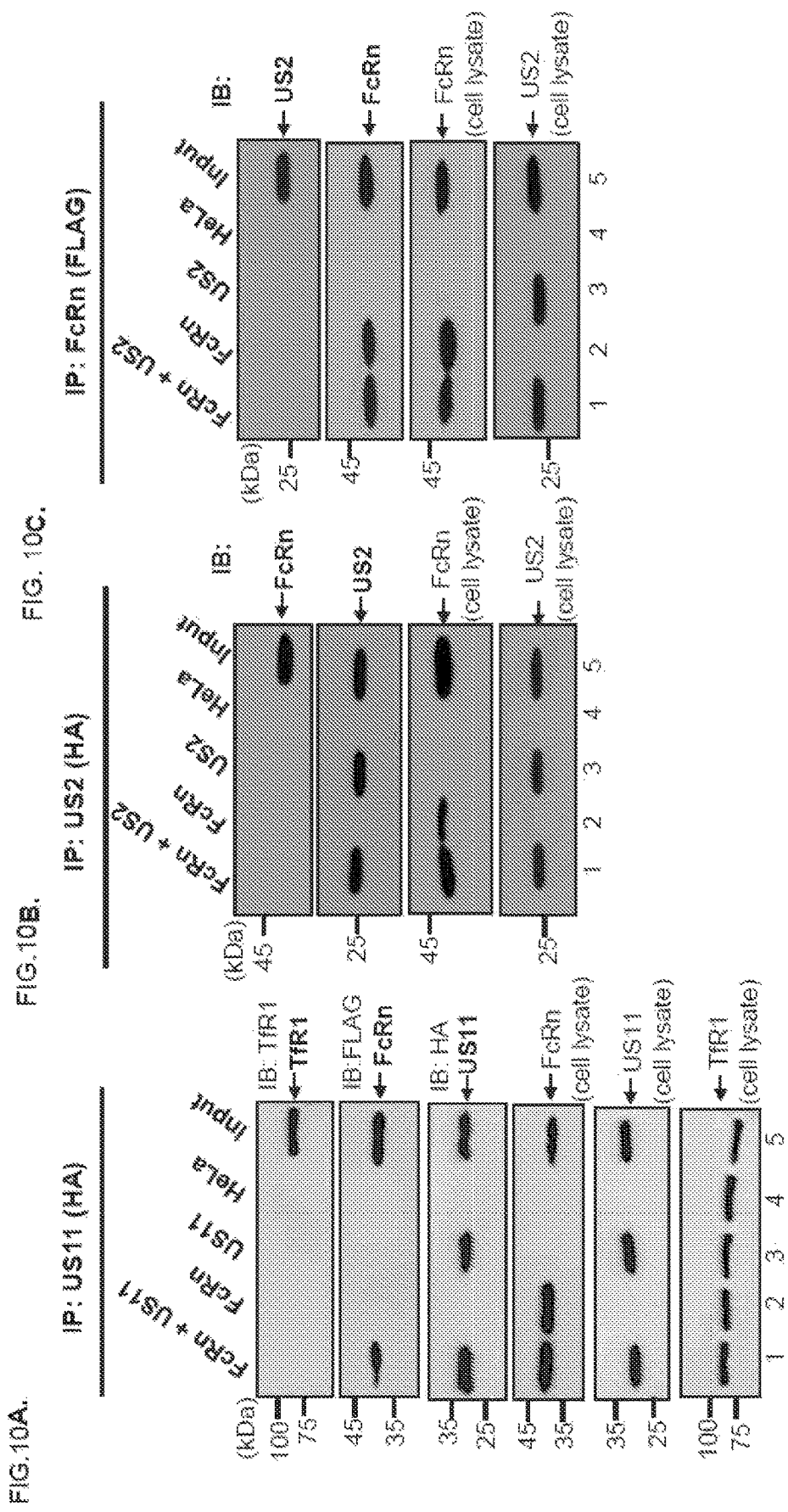
FIG. 10A–C. US11 does not interact with endogenous transferrin receptor 1 (TfR1) and FcRn does not interact with the HCMV US2.

HeLa$^{FcRn}$ or HeLa cells were transfected with plasmids encoding HA-tagged US11 cDNA. Cells lysed with CHAPS buffer were used for immunoprecipitation with either anti-FLAG (for FcRn) (FIG. 1A) or anti-HA (for US11) (FIG. 1B) mAb. Using Western blotting with anti-HA and anti-FLAG Ab, it was shown that the anti-FLAG Ab coimmunoprecipitated US11 protein (FIG. 1A) and the anti-HA Ab coimmunoprecipitated FcRn heavy chain (HC) (FIG. 1B). The co-localization between FcRn and US11 using confocal microscopy (FIG. 1C) was analysed. FcRn appeared in a punctate or vesicular pattern within HeLa$^{FcRn}$ cells, while US11 was highly colocalized with FcRn in HeLa$^{FcRn+US11}$ cells (FIG. 1C). To identify the specificity of this interaction, FcRn was co-expressed with US2, and US11 with HFE at similar levels in HeLa cells. HFE possesses MHC class I-like structure. An interaction between US11 and HEFwas not detected (FIGS. 1D & 1E), US11 and endogenous transferrin receptor (TfR1) (FIG. 10A), or FcRn and US2 (FIGS. 10B & 10C) in a reciprocal immunoprecipitation experiment, indicating a high degree of interaction specificity between FcRn and US11.

Figure 11:
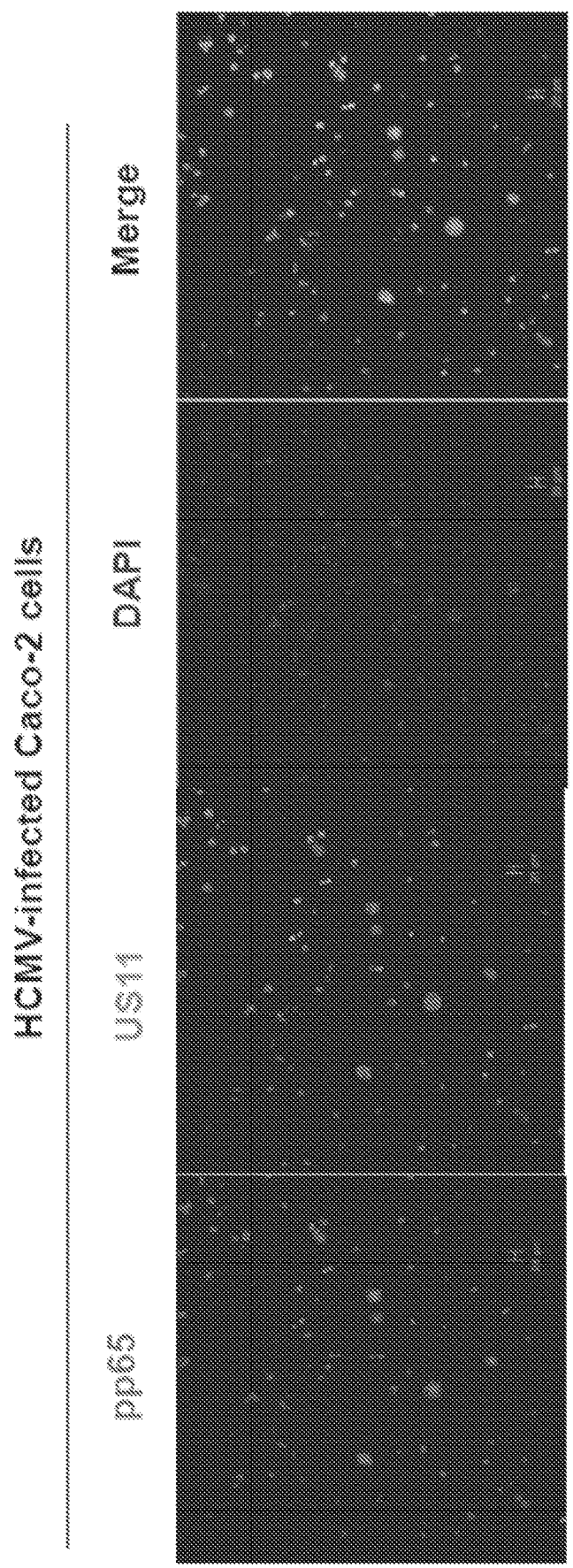
FIG. 11. HCMV-infected Caco-2 cells. Caco-2 cells were grown on glass coverslips and infected with HCMV at an MOI of 5. At day 2 p.i., monolayers were fixed with 4% paraformaldehyde and permeabilized in 0.2% Triton X-100. Subsequently, the cells were incubated with affinity-purified anti-US11 or anti-pp65 specific Ab, followed by Alexa Fluro 488- or 555-conjugated IgG. Staining appears in the merged images and indicates colocalization of US11 with pp65. The nuclei were stained with DAPI.

To further characterize the interaction between FcRn and US11, several types of human cells were infected, including primary human umbilical vein endothelial cells (HUVEC), endothelial HMEC-1, THP-1 cells, and human intestinal epithelial Caco-2, with clinical strain HCMV at an MOI of 5. Successful infection was confirmed by quantifying expression levels of phosphoprotein 65 (PP65), an abundantly produced HCMV protein (FIG. 11). At day 2 post-infection (p.i.), cell lysates from infected or mock-infected cells were immunoprecipitated with anti-US11 Ab (FIG. 1F) or anti-FcRn Ab (FIG. 1G) in primary HUVEC cells. It was then determined that anti-US11 Ab co-immunoprecipitated with FcRn HC in infected cells (FIG. 1F). Similarly, anti-FcRn Ab was also found to co-immunoprecipitate with US11 protein in infected cells (FIG. 1G). It was found that this interaction between US11 and FcRn was also present in either monocytic THP-1 (FIGS. 12A & 12B) or PMA-differentiated macrophage-like THP-1 cells (FIGS. 12C & 12D), human endothelial HMEC-1 (FIGS. 12E & 12F), and human intestinal epithelial Caco-2 (FIGS. 12G & 12H). These results indicate that that FcRn and US11 specifically interact with each other during HCMV infection in multiple cell types.

A GST-tagged US11 and GST-tagged cytoplasmic tail (CT) FcRn proteins (FIG. 13A) were designed. The purified GST-US11 or GST-FcRn CT protein was used for immunizing mice or rabbits to produce US11- or FcRn-specific antibodies that were affinity-purified as previously described (52). To better understand the interaction between US11 and FcRn, both type I transmembrane glycoproteins, pull-down assays were used. It was found that GST-US11, captured human FcRn (FIG. 13B) from HeLa$^{FcRn}$ cells, while a GST HCMV US11 protein containing only the cytoplasmic tail of FcRn failed to pull down US11 from HeLa$^{US11}$ cells (FIG. 13C). The results support our hypothesis that the main site of contact between US11 and FcRn is between their extracellular domains.

US11 Expression Reduces FcRn Trafficking to the Early Endosomal Compartment by Retaining FcRn in the Endoplasmic Reticulum (ER)

Figure 2B:
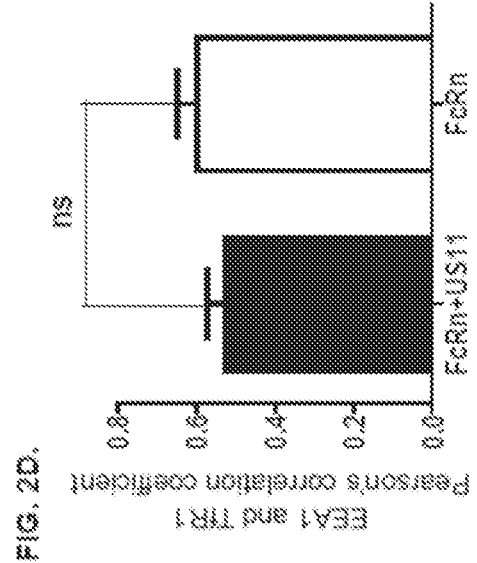
Figure 2C:
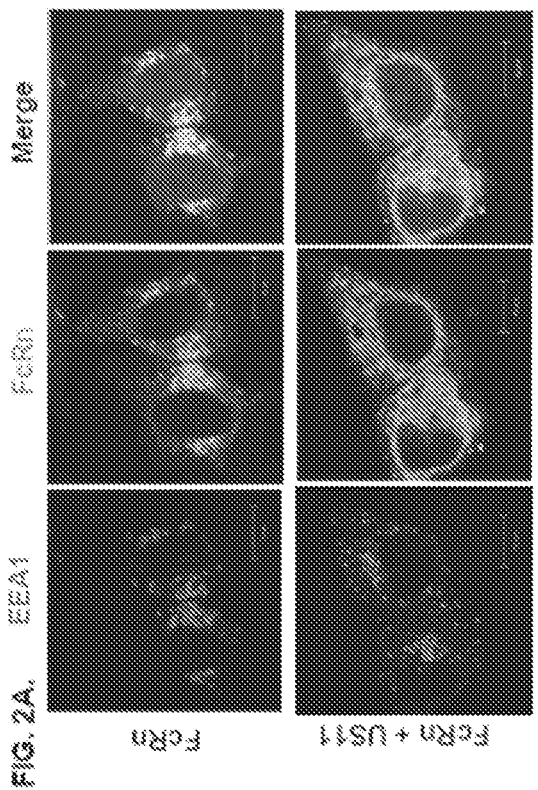
Figure 2D:
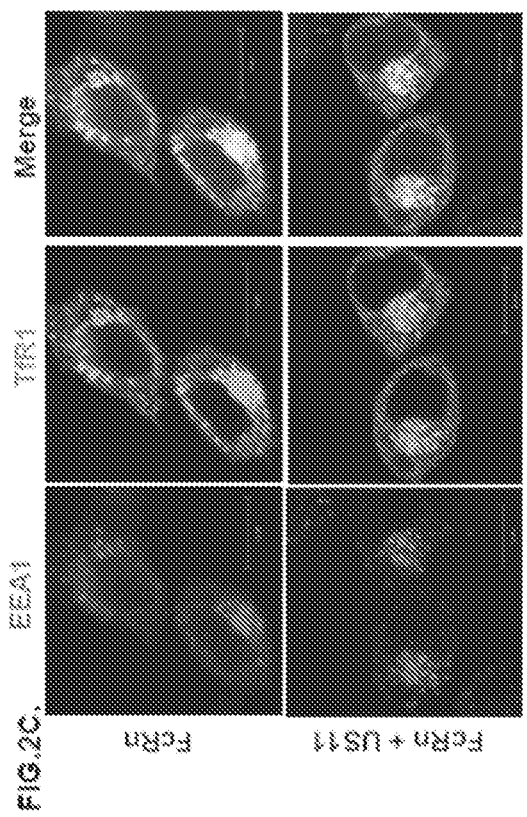

In most cell types, most FcRn resides in acidic endosomes, with limited presence on the cell surface. In early endosomes, FcRn binds pinocytosed or endocytosed IgG (38). It was hypothesized that FcRn distribution in the endosome would be affected by the interaction of US11 with FcRn HC. A stable cell line HeLa$^{FcRn+US11}$ was constructed expressing both the FcRn and US11 and compared the cellular distribution of FcRn between HeLa$^{FcRn}$ and HeLa$^{FcRn+US11}$ cells. In HeLa$^{FcRn+US11}$ cells, co-localization of FcRn and the early endosomal marker EEA1 was significantly decreased compared with control HeLa$^{FcRn}$ cells (FIGS. 2A & 2B). This suggests that US11 expression impairs FcRn endosomal trafficking. The reduction of colocalization between FcRn and EEA1 is unlikely due to the decreased expression of FcRn in HeLa$^{FcRn+US11}$ cells because the same HeLa$^{FcRn}$ cell line was used for transfecting the US11 expression plasmid and for control cells to monitor the level of FcRn expression. Although the over-expression of FcRn does not affect its intracellular trafficking pattern (52, 53), the over-expression of US11 may cause extensive remodeling of intracellular membranes. To investigate this possibility, the co-localization of transferrin receptor (TfR1, CD71) with EEA1 was compared between HeLa$^{FcRn}$ and HeLa$^{FcRn+US11}$ cells (FIG. 2C). It was found there were no significant difference in co-localization of TfR1 with EEA1 between HeLa$^{FcRn}$ and HeLa$^{FcRn+US11}$ cells (FIG. 2D), suggesting that the potential remodeling of cellular membranes by the over-expression of US11 may not affect endogenous protein trafficking. Together, these data confirm that the routing of FcRn to endosomes in human epithelial cells is significantly reduced by US11.

Figures 2E, 2F, 2G, 2H:
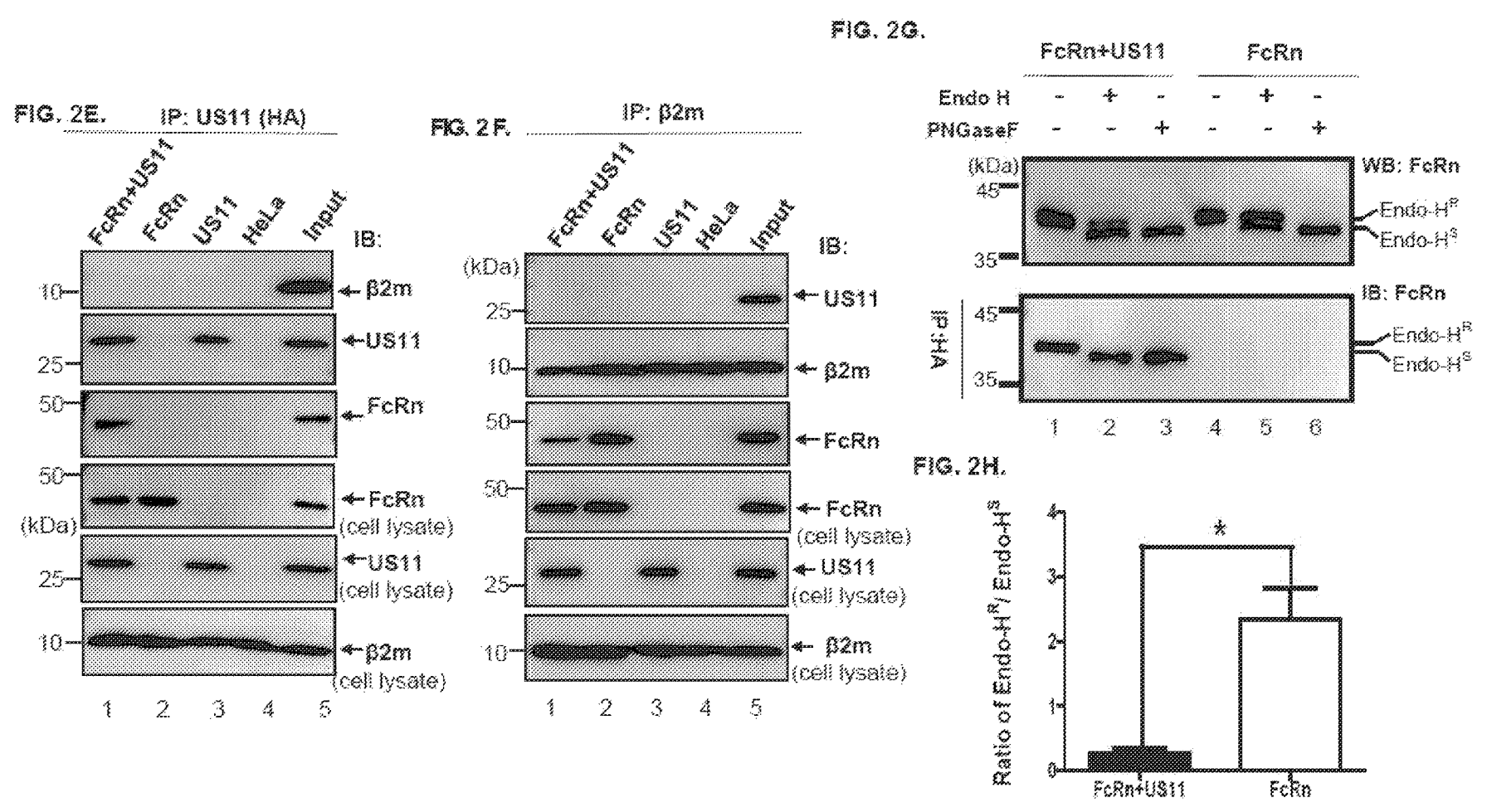

The functional FcRn molecule consists of the HC bound to $\beta_2$m. To further characterize the interaction between FcRn and US11, the interactions between US11 and these subunits were tested. Lysates from HeLa$^{FcRn+US11}$ were immunoprecipitated with anti-HA (for US11) or anti-$\beta_2$m Ab and blotted with anti-$\beta_2$m (BBM1) Ab to detect $\beta$2m (FIG. 2E) or anti-HA Ab to detect US11 (FIG. 2F). Immunoprecipitates were sequentially blotted with Abs against US11, FcRn, or $\beta_2$m (BBM1 mAb). Anti-HA Ab failed to co-immunoprecipitate $\beta_2$m (FIG. 2E). Similarly, $\beta_2$m mAb did not pull down US11 (FIG. 2F). However, an Ab against either HA or $\beta_2$m co-immunoprecipitated FcRn HC. These data strongly suggest that HCMV protein US11 interacts with $\beta_2$m-free FcRn HC.

Figures 21A, 21B:
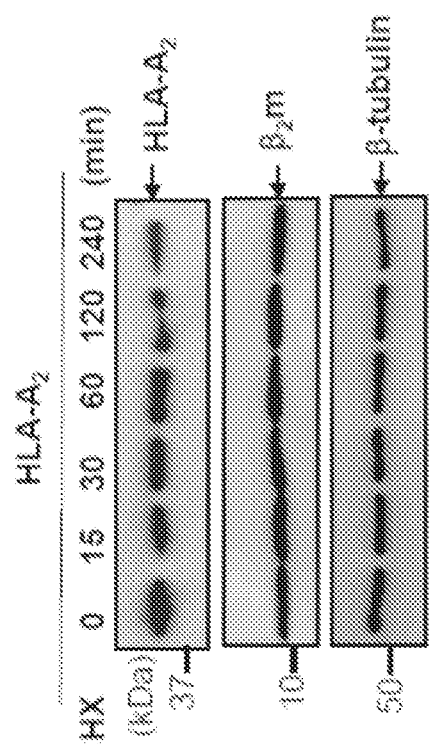
FIG. 21A-D. US11 expression facilitates MHC class I degradation in a cycloheximide (CHX) chase assay. HeLa$^{HLA-A2+US11}$ and HeLa$^{HLA-A2}$ cells were treated with CHX (100 µg/ml) for the indicated time.

Structural studies of FcRn have revealed a single N-linked glycosylation site (54). To identify the glycosylation status of FcRn in US11$^+$ cells, cell lysates were treated with either Endo H glycosidase, which cleaves high mannose oligosaccharides formed only in the ER, or with PNGase amidase, which cleaves hybrid and complex oligosaccharides formed in both the ER and Golgi complex. FcRn HC from HeLa$^{FcRn+US11}$ cells was much more sensitive to Endo H digestion than FcRn from HeLa$^{FcRn}$ cells (FIG. 2G, top panel). As expected, FcRn from both cell lines was sensitive to PNGase F digestion. It was then tested the Endo H sensitivity of FcRn in anti-US11 immunoprecipitates from HeLa$^{FcRn+US11}$ cells. As shown in FIG. 2G (lower panel), FcRn HC (lane 2) in a US11 immunoprecipitation from HeLa$^{FcRn+US11}$ cells demonstrated a mobility similar to FcRn HC after PNGase F digestion (lane 3). The full sensitivity of FcRn HC to Endo H digestion conforms to an ER-specific glycosylation pattern of FcRn within the FcRn/US11 complex (FIG. 21I). Overall, these findings suggest that US11 is capable of retaining FcRn in the ER. This strongly supports our conclusion that the known failure of newly synthesized FcRn to assemble with $\beta_2$m, undergo maturation, and transit to the Golgi complex during HCMV infection is due to its physical association with US11.

US11 is Necessary for FcRn Protein Degradation During HCMV Infection

Figure 3A:
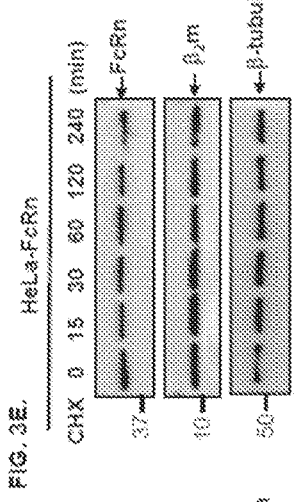
Figure 3B:
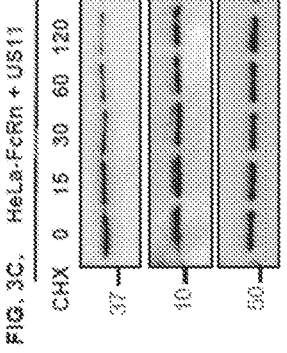

To examine how US11 affects FcRn expression, the expression levels of surface and intracellular FcRn were compared in HeLa$^{FcRn}$ or HeLa$^{FcRn+US11}$ cells using flow cytometry. It was found that US11 diminished both the surface and intracellular expression level of FcRn (FIG. 3A). In contrast, US11 affected neither the surface nor the intracellular expression level of HFE under the same conditions (FIG. 3B), suggesting a specific downregulation of FcRn by US11.

Figure 3C:
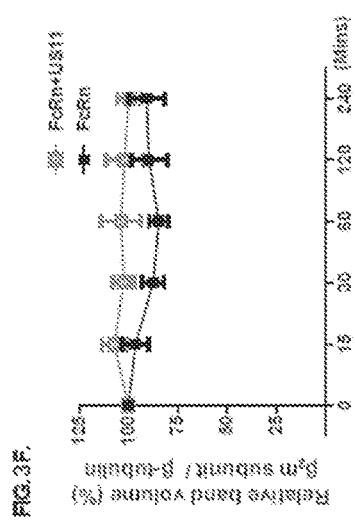
Figure 3D:
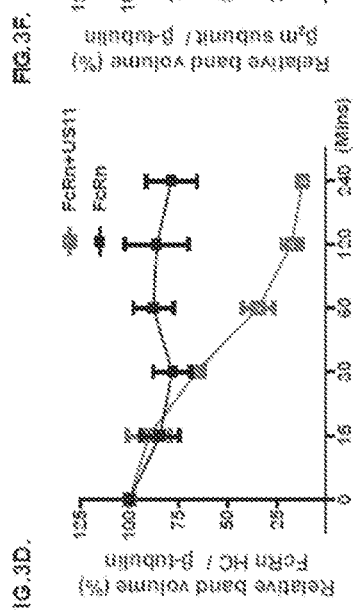
Figure 3E:
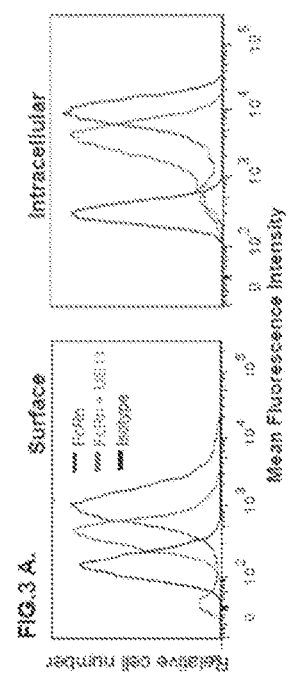
Figure 3F:
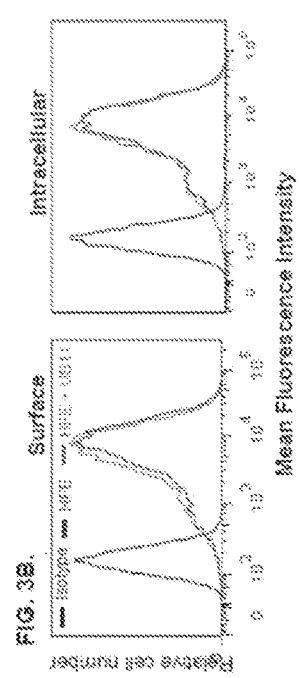

A protein's steady-state level depends on the rates of protein synthesis and degradation. To specifically monitor the rate of FcRn HC degradation, a quantitative cycloheximide (CHX) chase assay was performed. HeLa$^{FcRn+US11}$ (FIG. 3C) and HeLa$^{FcRn}$ (FIG. 3E) cells were treated with CHX (100 µg/ml) and FcRn protein intensity detected in Western blot was measured by an NIH Imager for the indicated times. In HeLa$^{FcRn+US11}$ cells, the expression of US11 induced a significant and time-dependent decrease in FcRn protein levels (FIG. 3C & 3D) in comparison with that of HeLa$^{FcRn}$ cells (FIG. 3E). Expressed FcRn protein in US11$^+$cells also had a shorter half-life, compared to the long-term stability of FcRn in US11 negative cells. Therefore, US11 stimulated FcRn protein turnover (FIG. 3D), further indicating that US11 promotes FcRn protein degradation. In contrast, a significant change was not detected in the levels of β2m (FIG. 3F), suggesting that the effect of US11 on FcRn levels was not due to either US11- or CHX-induced cytotoxicity.

Figures 14F, 14G, 14H, 14I:
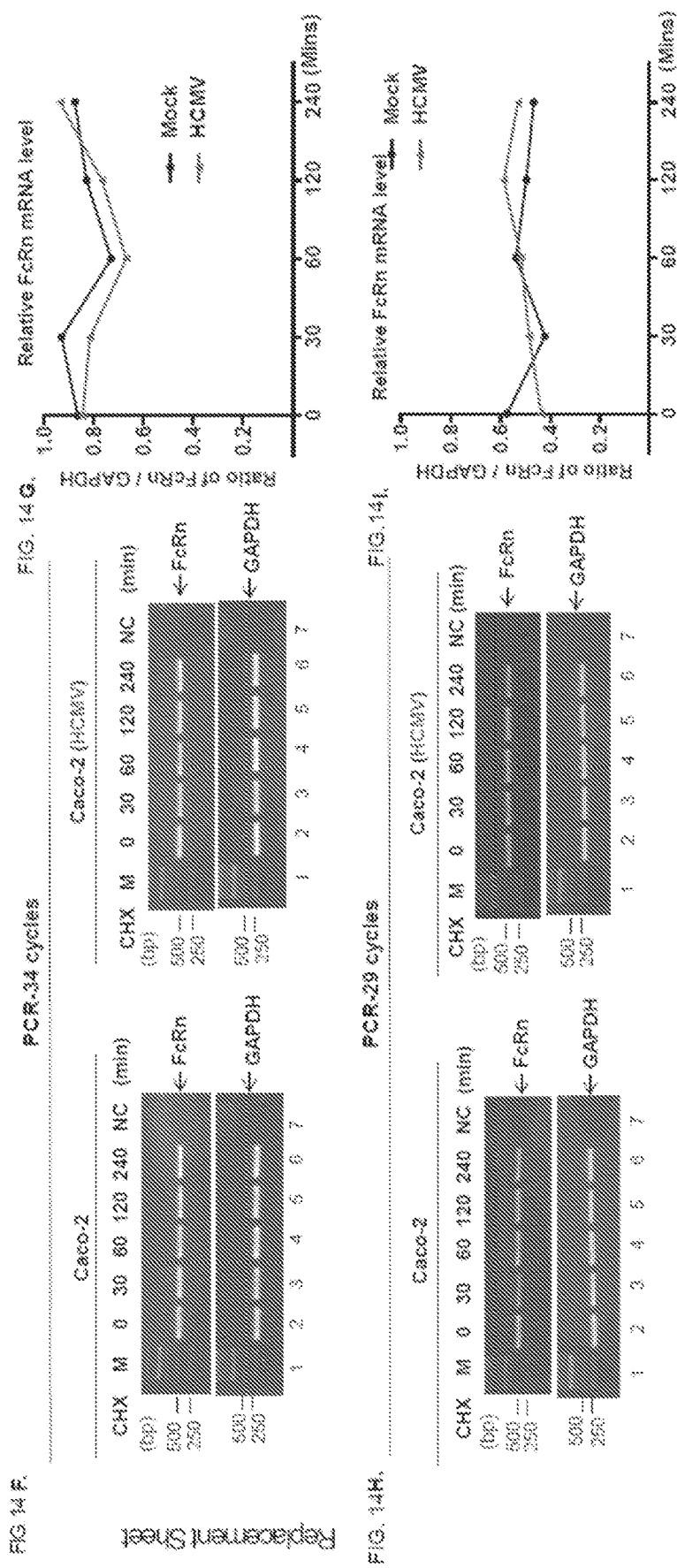

To identify whether this effect of US11 on endogenous FcRn is seen during HCMV infection, primary umbilical vein endothelial cells (HUVEC) or human intestinal Caco-2 epithelial cells which endogenously express FcRn (39) were infected. 48 hr post-infection, a quantitative CHX chase was performed, as described previously, on the infected HUVEC or Caco-2 cells. Compared to mock-infected controls (FIG. 3I & FIG. 14C), the expression levels of FcRn HC were significantly decreased in HCMV-infected HUVEC cells (FIGS. 3G & 3H) or Caco-2 cells (FIGS. 14A & 14B). IT was also detected that FcRn mRNA levels did not change in Caco-2 cells (FIG. 14F–I); these results indicate that FcRn is not regulated by HCMV at the transcriptional level. This FcRn down-regulation during infection was further supported by HCMV-infected human intestinal Caco-2 epithelial cells or by measuring intracellular levels of FcRn in HCMV-infected THP-1 and HMEC-1 cells using flow cytometry. It was found that HCMV infection reduced the expression level of intracellular FcRn in both THP-1 (FIG. 15A) and HMEC-1 cells (FIG. 15B). To identify the role of US11 in this process, two independent US11 RNA-mediated interference (siRNA) species were used to knock-down US11 in HCMV-infected cells. It was found that FcRn degradation was significantly reduced in US11 siRNA-treated HUVEC (FIGS. 3K & 3H) or Caco-2 (FIGS. 14B & 14E), although β₂m levels were unaffected in HUVEC cells (FIGS. 3K & 3J) or Caco-2 cells (FIGS. 14D & 14E). It was also noticed that the FcRn level at 240 min post chase (FIG. 3K & FIG. 14E) was moderately restored by US11 siRNA in virus infected cells in comparison with mock-infected cells (FIG. 3I & FIG. 14C). It is likely that this result was associated with the incomplete blocking of US11 expression by US11 siRNA, which was shown in a US11 blot (FIG. 3K & FIG. 14E, middle panels). Taken together, these results strongly suggest that US11 is required for decreasing the intracellular concentration of FcRn during HCMV infection.

US11 Recruits Derlin-1 and TMEM-129 to Engage FcRn

Previous studies have shown that US11 interacts with Derlin-1 (55, 56) and Derlin-1 facilitates movement of misfolded proteins through the ER membrane (57). Derlin-1 was identified as a potential partner of the FcRn-US11 complex. The US11-Derlin-1 interaction is dependent on a polar glutamine residue (Q192) in the US11 transmembrane domain (58). To identify interactions between FcRn, US11, and Derlin-1, HeLa$^{FcRn}$ cells were transfected with plasmids encoding Derlin-1 and either a wild-type or mutant US11 Q192L. Using an anti-FLAG Ab against FcRn, US11 and Derlin-1 (FIG. 4A, lane 1) were coimmunoprecipitated, or mutant US11 without Derlin (FIG. 4A, lane 2). Using an anti-Myc Ab against Derlin-1, coimmunoprecipitation of both FcRn HC and US11 (FIG. 4B, lane 1) wa observed, but failed to pull down FcRn in the presence of mutant US11 Q192L (FIG. 4B, lane 2), verifying that Derlin-1 is incapable of binding mutant US11 Q192L. Furthermore, anti-FLAG Ab against FcRn did not coimmunoprecipitate Derlin-1 in the absence of US11 (FIG. 4C, lane 1). Conversely, the FcRn levels were maintained in HeLa$^{FcRn+US11\ Q192L}$ cells during the CHX treatment, suggesting that the observed FcRn decrease is mediated through interactions between US11 and Derlin-1 (FIGS. 4D & 4E). Together, these data demonstrate that the Derlin-1 binding activity of US11 is required for FcRn degradation.

Figure 16B:
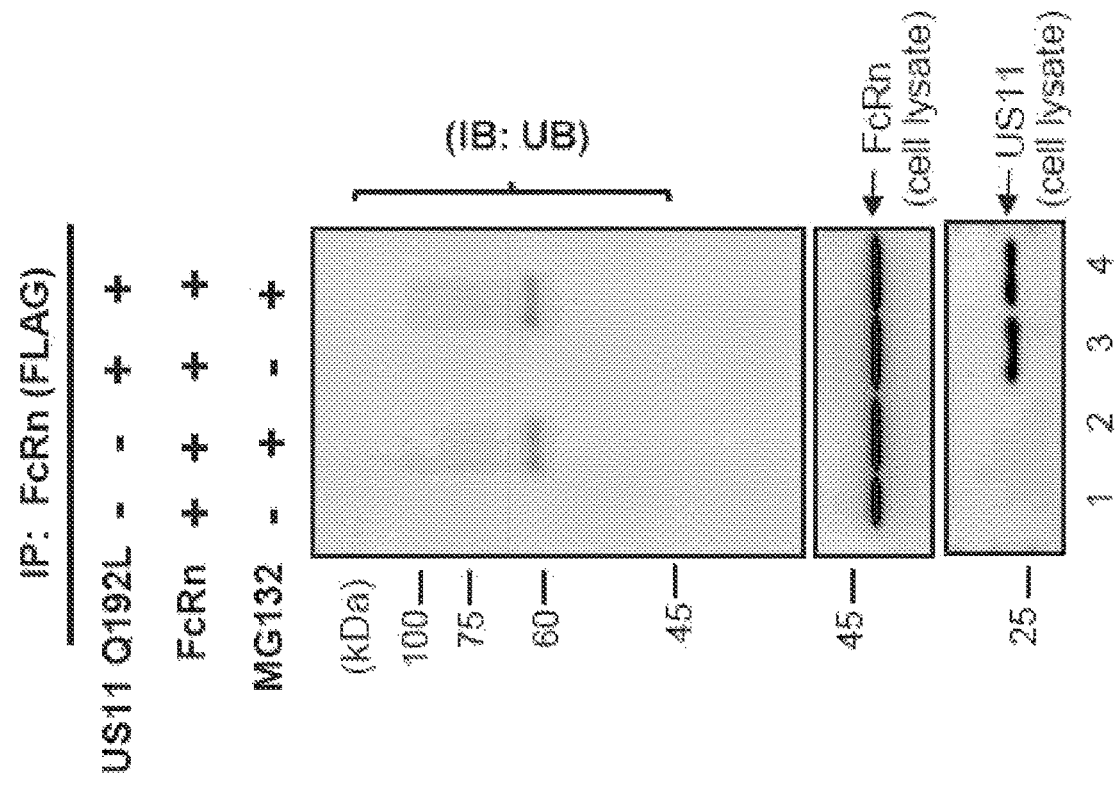
FIG. 16A–B.
Figure 16A:
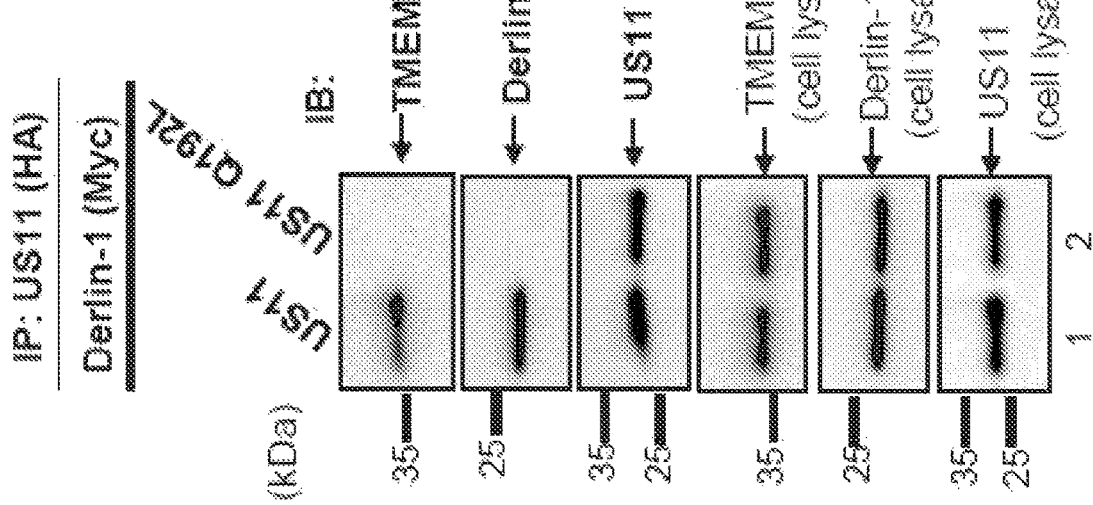

Derlin-1 is known to interact with the E3 ligases. A thorough screening of the candidate ligases in the presence of both US11 and Derlin-1 showed that the E3 ligase TMEM129 (59, 60) was recruited to the FcRn/US11/Derlin-1 complex (FIGS. 4F & 4G). In the absence of US11 expression, immunoprecipitation of FcRn failed to pull down TMEM129 (FIG. 4F, lane 2). In addition, TMEM129 was capable of directly pulling down Derlin-1 in HeLa$^{FcRn}$ cells without US11 (FIG. 4G, lane 2), suggesting that the binding of TMEM129 to Derlin-1 is US11-independent. The recruitment of TMEM129 to the FcRn/US11 complex is through Derlin-1, as the wild type US11 coprecipitated with TMEM129 while the Derlin-binding mutant US11 Q192L failed to pull down TMEM129 (FIG. 16A).

With this information in hand, it was further decided to identify the role of TMEM129 in the down-regulation of FcRn in HeLa$^{FcRn+US11}$ cells. It was found that depletion of TMEM129 using siRNA (FIG. 4H, bottom) reduced the loss of FcRn expression in HeLa$^{FcRn+US11}$ cells (FIGS. 4H & 4I), suggesting that TMEM129 is critical for US11-mediated degradation of FcRn. It was therefore concluded that TMEM129 is recruited to the FcRn/US11 complex via Derlin-1 and is responsible for US11-mediated FcRn degradation.

The cytoplasmic tail of FcRn HC is necessary for US11-mediated degradation

It has been shown that the extracellular domains of US11 and FcRn interact with each other (FIG. 13B+FIG. 13C). It is unknown whether the cytoplasmic tail of FcRn plays a role in US11-mediated degradation. To elucidate the involvement of the cytoplasmic tail (CT) of FcRn HC during US11-mediated degradation, a mutant FcRn with a truncated cytoplasmic tail was generated, FcRn-tailless (FIG. 5A), leaving five residues allowing the proper insertion of the protein into the membrane (52). It has been shown that similarly truncated FcRn HC behaves like full-length FcRn HC with respect to folding, assembling with β₂m, and pH-dependent binding to IgG (52). To examine whether deletion of the FcRn CT affects US11-induced degradation, HeLa$^{US11}$ cells were transfected with either a WT FcRn or FcRn-tailless (FIG. 5B). The fate of both proteins was further examined using a CHX-chase experiment. In the absence of proteasome inhibitor, WT FcRn HC was degraded by 60 min post-chase (FIGS. 5B & 5C). This was in marked contrast with tailless FcRn, which persisted in the presence of US11 (FIGS. 5B & 5C). To identify the critical region within the FcRn CT that is responsible for its degradation, a series of C-terminal FcRn deletion mutants were constructed and examined their susceptibility to US11-mediated degradation. It was found that deletion of a single C-terminal alanine residue affected its susceptibility to US11-induced degradation in a manner like that observed after deleting the entire FcRn CT (FIGS. 5B & 5C). Indeed, the half-life of FcRn-365A–/– was comparable with that of FcRn-tailless in HeLa$^{US11}$, while the alanine deletion also rendered FcRn resistant to US11-induced degradation (FIGS. 5B & 5C). It was therefore demonstrated that the FcRn cytoplasmic tail is necessary for its degradation.

It has been shown that FcRn HC interacts with Derlin-1 via US11 (FIG. 4A), and that US11 binds to Derlin-1 via its transmembrane domain (FIG. 4B). To gain a deeper understanding of how the FcRn CT is involved during US11-induced degradation of FcRn HC, it was next determined how FcRn CT interacts with US11 and Derlin-1. Using co-precipitation (FIG. 5D), it was found that the FcRn tailless mutant maintained an interaction with US11. However, FcRn tailless had a markedly reduced interaction with Derlin-1 (FIG. 5E; compare lanes 1 and 2). In addition, it was found that FcRn-365A−/− also had a similarly decreased interaction with Derlin-1 (FIG. 5E, compare lanes 1 and 3). Finally, immunoprecipitation of FcRn tailless failed to precipitate TMEM129, suggesting that the interaction between FcRn CT and Derlin-1 is also important for TMEM129 recruitment (FIG. 5E). When HeLa$^{US11+FcRn}$ cells were transfected with a plasmid encoding Derlin-1, Derlin-1 lacking its N-terminus (NT−/−) or C-terminus (CT−/−), and FcRn was immunoprecipitated, it was found that the C-terminus of the Derlin-1 was required for tight binding to FcRn in the presence of US11 (FIG. 5F, lane 3). Taken together, these results suggest that the cytoplasmic tail of FcRn HC is required for US11-induced degradation, perhaps via its interaction with Derlin-1.

The US11/Derlin-1/TMEM129/Ube2J2 Protein Complex Induces FcRn Dislocation, Ubiquitination, and Subsequent Degradation Ubiquitination of a protein substrate is a critical step in protein degradation (62). It was then investigated whether US11 regulates FcRn turnover through a ubiquitination-dependent mechanism. HeLa$^{FcRn}$ cells were transfected with either WT or a mutant US11Q192L incapable of binding Derlin-1. It was found that US11 specifically induced FcRn ubiquitination in the presence of proteasome inhibitor, MG132 (FIGS. 6A & 6B). However, the mutant US11 Q192L failed to trigger FcRn ubiquitination (FIG. 16B), suggesting that the Derlin-1 binding activity of US11 is required for FcRn ubiquitination. Furthermore, FcRn tailless (FIG. 6C, lane 2) and FcRn CT365A−/− (FIG. 6C, lane 3) exhibited significantly less ubiquitination in comparison with WT FcRn (FIG. 6C, lane 1), indicating that the cytoplasmic tail of FcRn is necessary for US11-induced FcRn ubiquitination.

FcRn proteins were also detected as both slow and fast migrating bands (FIG. 6C, lane 1, middle). To verify this, a CHX chase analysis was performed. It was found that FcRn from HeLa$^{FcRn+US11}$ cells migrated slowly during early chase time points (FIG. 6D, lane 4) and faster (FIG. 6D, lanes 5-6) during later time points in cell lysates in the presence of both US11 and proteasome inhibitor. It was reasoned this faster migrating band might represent removal of the FcRn glycan by cytosolic N-glycanase. To determine whether this was the case, HeLa$^{FcRn+US11}$ or HeLa$^{FcRn}$ cells were subjected to a subcellular fractionation and used the extracts from either the pellet (membrane) or supernatant (cytosol) for blotting analysis of FcRn. Using Endo H or PNGase F digestion, it was found that the slower migrating form of FcRn detected in the membrane fractions of HeLa$^{FcRn}$ corresponded to Endo H-resistant protein (FIG. 6E, middle). However, FcRn HC from HeLa$^{FcRn+US11}$ cells was much more sensitive to Endo H digestion (FIG. 6E, middle), and some FcRn was present in the membrane fraction only and displayed normal maturation into a slower migrating form. As shown in FIG. 6E (middle), the faster migrating bands (lanes 3 & 4) from the membrane and cytosol fractions of HeLa$^{FcRn+US11}$ cells had a mobility similar to the sensitive bands from Endo H digestion. As expected, FcRn from either source was sensitive to PNGase F digestion (FIG. 6E, bottom). It was therefore concluded that the two forms of FcRn represent a glycosylated version, which co-fractionates with the ER membrane, and a cytosolic, non-glycosylated version of FcRn. The origin of this non-glycosylated FcRn form could be due to dislocation of FcRn from the ER; the cytosolic N-glycanase removes the glycan from the FcRn. The cytosolic, non-glycosylated form of FcRn may represent an intermediate before its degradation because it accumulated only in the presence of MG132 inhibitor.

The E3 ligase TMEM129 contains an atypical RING domain with intrinsic protein E3 ubiquitin ligase activity (59, 60). To show that TMEM129 is necessary for FcRn ubiquitination, TMEM129 expression was knocked down (FIG. 6F, middle, lane 2). FcRn was immunoprecipitated and it was found that the robust FcRn ubiquitination induced by US11 (FIG. 6F, top, lane 1) was abrogated in TMEM129 siRNA-treated cells (FIG. 6F, top, lane 2). The atypical RING-C2 domain of TMEM129 creates a binding platform for E2 conjugating enzymes. Previous studies (59, 60) implied that Ube2J1 or Ube2J2 is a potential player in the TMEM129-mediated ubiquitination of FcRn, thus their roles were further elucidated using knock-downs. It was observed that knock-down of Ube2J2, but not Ube2J1, nearly abolished US11-induced FcRn ubiquitination (FIG. 6G, top, lane 1) and rescued FcRn from degradation in HeLa$^{FcRn+US11}$ cells (FIGS. 6H & 6I). It was concluded that the E3 ligase TMEM129 recruits Ube2J2 for US11-induced ubiquitination of FcRn, leading to its eventual ER dislocation and proteasome degradation.

HCMV Infection or US11 Expression Reduces FcRn-Mediated IgG Transcytosis in Polarized Human Epithelial Cell Monolayers To examine whether HCMV infection or US11 alone affects FcRn-mediated IgG transcytosis across polarized epithelial cells, it was first tested whether the association of FcRn with US11 affects FcRn binding to IgG. FcRn is known to bind IgG at pH below 6.5 and to release IgG at neutral and basic pH (37); an association between FcRn HC and $\beta_2$m is important for pH-dependent IgG binding (35). Lysates from HeLa cells expressing FcRn and/or US11 were incubated with IgG-Sepharose at either pH 6.0 or pH 7.4; lysates from HeLa$^{FcRn}$ cells were used as a positive control. Eluates and cell lysates were subjected to analysis by Western blot. As expected, FcRn from HeLa$^{FcRn}$ cells bound IgG at pH 6.0 (FIG. 7A, lane 2), but not at pH 7.4 (FIG. 7B, lane 2). Similarly, β2m from the IgG binding eluates was detected at pH 6.0 (FIG. 7A, lane 2), but not at pH 7.4 (FIG. 7B, lane 2). US11 proteins were not detected in the FcRn binding eluates of IgG beads at pH 6.0 (FIG. 7A, lane 1). Furthermore, FcRn and β2m levels (FIG. 7A, lane 1) eluted from IgG beads were remarkably decreased in HeLa$^{FcRn+US11}$ cells when compared to in HeLa$^{FcRn}$ cells alone (FIG. 7A, lane 2). These data strongly suggest that the association of US11 with FcRn HC interferes with FcRn binding to IgG. Hence, when US11 binds FcRn, it prevents the formation of the FcRn/β2m complex, causes FcRn HC to translocate from the ER (FIGS. 6C & 6D) and consequently blocks functional binding to IgG.

FcRn transports IgG in polarized epithelial cells between the apical and basolateral sides of the cell (39, 41). HCMV is also known to infect Caco-2 cells at the basolateral membrane (63). The possibility that HCMV-infected Caco-2 epithelial cells have altered IgG transcytosis was explored. Human IgG Abs were added to the apical surface of a Caco-2 cell monolayer at 37° C. and then measured IgG transport into the opposite basolateral chamber using cells infected with HCMV in the basolateral surface. After 2 hr, intact human IgG applied to the apical side was transported across the mock-infected monolayer (FIG. 7E, lane 4; FIG. 7F). IgG transport at 37° C. from the apical to basolateral side was significantly (P<0.001) decreased or blocked in HCMV-infected Caco-2 cells (FIG. 7E, lane 2, FIG. 7F) when compared to mock-infected cell monolayers. It was also shown that IgG transport from the apical to basolateral direction was significantly decreased (P<0.001) or blocked in HCMV-infected placental epithelial BeWo cells (FIG. 7G, lane 3; FIG. 7H) as compared with mock-infected BeWo cell monolayers (FIG. 7G, lane 1; FIG. 7H).

Figure 17A:
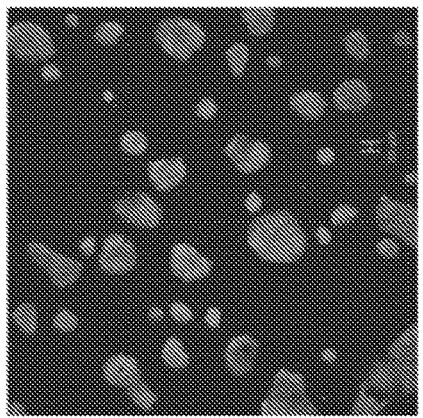
FIG. 17A-B.

Infecting Caco-2 monolayers with HCMV for 48 hr may result in leakage of the IgG Ab. To further show whether US11 expression alone reduces IgG transcytosis, US11 Caco-2 cells were stably expressed (FIG. 17A). Then, human IgG Ab (0.5 mg/ml) was added apically into the Caco-2$^{US11}$ cell monolayer and further incubated for 2 hr to allow for transcytosis. The basolateral medium was then collected and human IgG was measured using Western blot (FIG. 7I) or ELISA (FIG. 7J). As seen in Caco-2$^{US11}$ cells, human IgG transport from the apical to basolateral direction was significantly decreased (P<0.001) in US11-expressing cells (FIG. 7I, lane 2; FIG. 7J) as compared with mock-transfected cell monolayers (FIG. 7I, lane 4; FIG. 7J). Human IgG was not transported at 4° C. in HCMV-infected Caco-2 (FIG. 7E, lane 4) or BeWo cells (FIG. 7G, lane 4), and US11-expressing Caco-2 cells (FIG. 7I, lane 1), suggesting that trans-epithelial flux of IgG Abs by passive diffusion across intercellular tight junctions or monolayer leaks did not contribute to the amount of detected IgG. Hence, it was concluded that US11 inhibits IgG transport across polarized epithelial cells.

US11 Expression Facilitates IgG Degradation

FcRn plays a critical role in IgG homeostasis by recycling IgG away from a catabolic pathway in the vascular endothelium, thereby extending its lifespan in the circulation and ensuring long-lasting protective immunity after infection or immunization (38, 64). FcRn resides primarily in early acidic endosomal vesicles (65, 66) and binds IgG that enters the cell by pinocytosis or endocytosis. Subsequently, FcRn efficiently recycles IgG back to the plasma membrane, whereby the near-neutral pH of the extracellular environment causes IgG release from FcRn. Any pinocytosed or endocytosed IgG that is not salvaged in this manner is efficiently trafficked to the lysosomes for degradation (38, 64). If US11 acts by preventing FcRn binding to IgG and trafficking to the endosome, it should consequently accelerate IgG degradation by promoting the trafficking of pinocytosed IgG to the lysosomes for degradation.

Figure 17B:
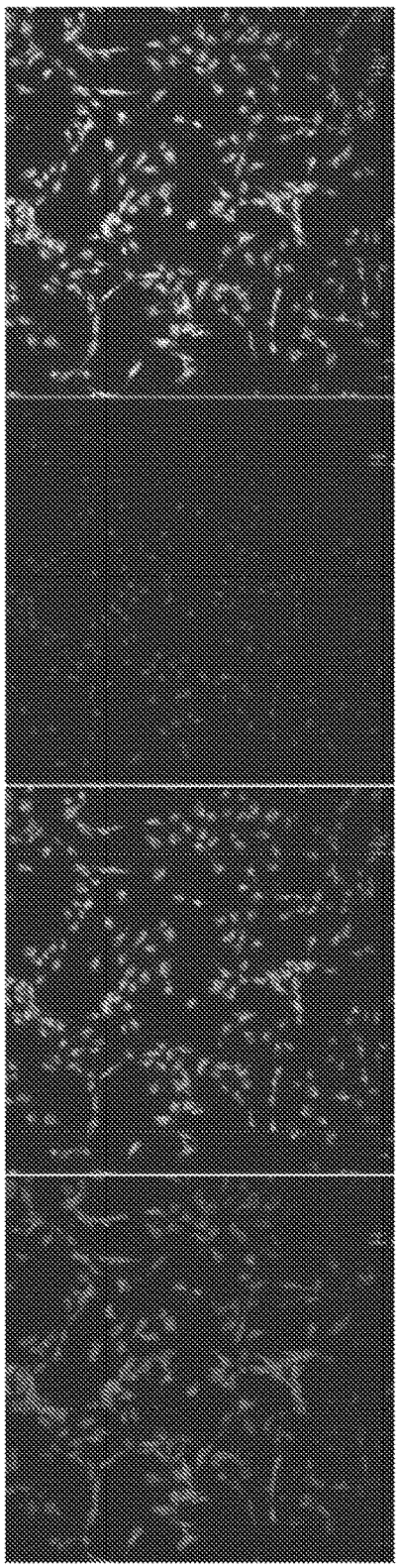

To test this hypothesis, HCMV-infected human endothelial HMEC-1 cells (FIG. 17B) were incubated with human IgG. After washing, the IgG in the supernatant was subsequently measured using ELISA. It was found that after a 48 hour incubation, the level of IgG that was recycled was significantly reduced (P<0.01) in HCMV-infected HMEC-1 cells in comparison with that in mock-infected cells (FIG. 8A & 8B). To further elucidate this process, HCMV-infected HMEC-1 cells were stained with anti-EEA1 mAb to visualize IgG trafficking to the endosome. IgG Ab was detected in the endosome of mock-infected HMEC-1 cells, but much less in the HCMV-infected HMEC-1 cells (FIGS. 8C & 8D). To further investigate the fate of IgG Ab, anti-lysosome-associated membrane glycoprotein-1 (LAMP-1), a lysosomal marker, was used to track IgG trafficking to lysosomal sites. Lysosomal transport of IgG Ab was negligible in IgG-treated mock-infected HMEC-1 cells during the incubation period (FIG. 8E). However, co-localization (FIG. 8E, yellow) of LAMP-1 and IgG Ab was more prominent in HCMV-infected HMEC-1 cells, suggesting that HCMV infection promotes lysosomal trafficking of IgG. Pearson's correlation coefficient analysis indicated significant colocalization of IgG Ab with endosomal (FIG. 8D) but much less lysosomal (FIG. 8F) markers in mock-infected HMEC-1 cells when compared with HCMV-infected HMEC-1 cells. Human IgG trafficking patterns in HCMV-infected HMEC-1 cells were verified in IgG-treated HeLa$^{FcRn+US11}$ cells (FIG. 18). The IgG degradation accelerated by US11 expression or HCMV infection was further verified in IgG recycling experiments, as HCMV infection or US11 expression significantly reduced the IgG recycling in either HMEC-1 cells or HeLa$^{FcRn}$ cells (FIG. 19). Taken together, these data strongly suggest that US11 prevents FcRn endosomal trafficking, ultimately resulting in the delivery of IgG to lysosomes for degradation.

Proteins trafficking through the secretory pathway must fold into their native state in the ER before progressing onwards (67, 68). Misfolded proteins are translocated across the ER-membrane, destined for cytosolic proteasome degradation in a process known as ER-associated degradation (ERAD) (69). Many pathogens including HCMV, exploit the ERAD system to nullify important components of the host immune system (70, 71). HCMV is a ubiquitous herpesvirus capable of establishing latency with episodic reactivation. It can cause life-threatening illness in immunocompromised patients, including transplant recipients, HIV+ patients, and developing fetuses. The success of HCMV to infect a large proportion of the world's population is due at least in part to its ability to evade the cellular immune system, and it was found that the virus also inhibits Ab responses. FcRn, the only Fc receptor known to protect and transport IgG across cellular barriers, plays a critical role in the development of immunity at all stages of life (38). It was initially hypothesized that HCMV infection impeded FcRn trafficking from the ER, leading to its absence in the acidic endosomal compartment and rendering it unable to bind IgG. In this study, it was demonstrated that HCMV infection causes FcRn degradation through an ERAD mechanism and thus, removes a critical feature of host immunity.

It was first determined that the HCMV protein US11 colocalizes with FcRn in transfected HeLa or HCMV-infected cells. This observation led us to measure a specific interaction between US11 and FcRn in transfected HeLa and HCMV-infected primary HUVEC, intestinal Caco-2 cells, endothelial HMEC-1 cells, and macrophage-like THP-1 cells. Our results in THP-1 cells were especially encouraging, because cells in the monocyte lineage are known to be a reservoir for latent HCMV infection. Early immature glycosylation patterns on the US11-FcRn complex were identified, suggesting that the complex is retained in the ER and supporting the observation that US11 is an ER resident protein (72). It was then observed that the presence of US11 correlates with an absence of FcRn in early endosomes. It was also determined that US11 interacts with nascent FcRn HC but not with FcRn-$\beta_2$m, suggesting that US11 captures newly synthesized FcRn HC before it binds $\beta_2$m. The exact molecular interactions between US11 and FcRn have yet to be fully characterized, but it seems that the US11 luminal domain targets the extracellular domain of FcRn, and the contribution of a critical residue to this interaction will be investigated. The possibility of generating a US11 mutant HCMV virus to verify a US11-FcRn interaction was explored. However, it was found that the HCMV genome encodes at least two additional proteins US6 and UL16 that interact with FcRn HC. These additional HCMV proteins may affect FcRn function and make the experiments more complexed in studying the impact of US11 on FcRn functions in US11 mutant virus-infected cells.

Figure 20:
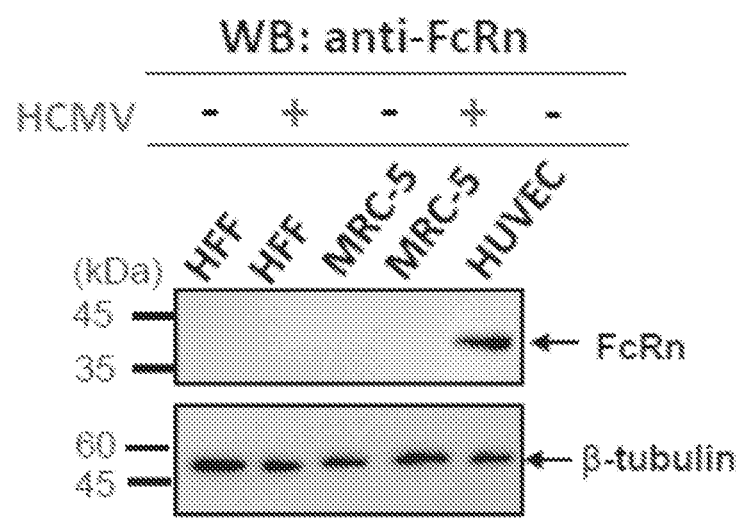
FIG. 20. Detection of FcRn expression in fibroblasts. The human foreskin fibroblasts (HFF) and fetal lung fibroblast-like MARC-5 cells were infected with HCMV at an MOI of 5. At day 2 p.i., the cell lysates (20 μg) from infected (lanes 2 & 4) or mock-infected (lanes 1 & 3) cells were subjected to 12% SDS-PAGE electrophoresis under reducing conditions, then transferred to a nitrocellulose membrane for Western blotting with anti-FcRn Ab. The cell lysates (20 µg) from the HUVEC cell line (lane 5) were blotted as controls. Immunoblots (IB) were developed with ECL. There was a failure to detect FcRn protein expression in the MRC-5 and HFF cell lines by Western blot analysis; HCMV infection also did not induce FcRn expression in the MRC-5 and HFF cell lines. Both MRC-5 and HFF cell lines were originally purchased from ATCC.

To identify whether the binding of US11 was sufficient for FcRn degradation, we generated a mutant cell line expressing FcRn tailless, a truncated protein that retained its interaction with US11. Interestingly, we observed no degradation of FcRn tailless, even in the presence of US11 binding, suggesting that US11 is not sufficient for FcRn degradation and the FcRn cytosolic tail is necessary for trafficking into the degradative ERAD pathway. To identify additional binding partners, we generated mutant forms of US11 and tested their ability to activate FcRn degradation using CHX chase experiments. It was discovered that a mutant US11 that failed to interact with Derlin-1 was incapable of causing FcRn degradation. It was also observed that deletion of the Derlin-1 cytosolic tail in its C-terminus also prevented it from tightly binding to FcRn HC. It was postulate that the interaction of the FcRn and Derlin-1 cytoplasmic tails may allow both molecules to engage ER dislocation machinery. It was therefore determined that the formation of an FcRn/US11/Derlin-1 complex is critical for FcRn degradation. Fielding et al. reported that HCMV downregulated cell surface or intracellular FcRn expression in HFF fibroblast cell line, which was detected by mass spectrometry (23). Although we were able to detect FcRn expression in human primary endothelial cell line HUVEC, we failed to detect FcRn expression by Western blot analysis in both uninfected or HCMV infected human foreskin fibroblasts (HFF) and fetal lung fibroblast-like MARC-5 cells (FIG. 20). This discrepancy may be caused by the protein detection method or the low level of FcRn expression in the HFF cells. More experiments need to be done to verify the finding by Fielding et al. (23).

It was observed that FcRn, following its capture by Derlin-1, is quickly dislocated, ubiquitinated and released from the ER into the cytosol. Derlin-1 is known to interact with E3 ubiquitination ligases. Although Derlin-1 interacts with a range of E3 ligases, its durable interaction with TMEM129 made TMEM129 a strong candidate for the final ubiquitination of FcRn. Structural analysis of TMEM129 identified it as a possible member of the RING family of E3 ligases (59, 60). It was demonstrated that the knockdown of TMEM129 and its cognate E2 UbE2J2 abolishes FcRn ubiquitination and prevents its degradation, even in the presence of US11. It was found that the E3 ligases Hrdl/Gp78, RMA-1, and TRC8 could not substitute for TMEM129, which may indicate that TMEM129 is necessary for US11-induced FcRn protein degradation. It is suggested that the major role of US11 is to facilitate FcRn binding to Derlin-1, leading to TMEM129-mediated ubiquitination of FcRn and its subsequent proteasomal degradation in the cytosol. Thus, US11 harnesses a Derlin-1/TMEM129-dependent pathway that is responsible for FcRn degradation.

The effects of US11 on FcRn-mediated IgG transport and protection were characterized. It was observed that US11 reduces FcRn-mediated IgG transport in epithelial monolayers and accelerates IgG catabolism in human endothelial cells. As HCMV infection cycles through periods of latency and reactivation, the long-lasting humoral immune responses are generated through the production of IgG. FcRn normally supports passive immunity in the neonate by facilitating transfer of maternal IgG Ab across the placenta. Post-delivery, FcRn continues to support an effective immune response against infection by transporting IgG across polarized epithelium lining mucosal surfaces (39-41). FcRn therefore contributes to a lifelong IgG-mediated immunity. For HCMV to evade immunity and be shed despite a potent immune response, it is suggested that it must have developed a mechanism to inhibit FcRn. It was found that expression of US11 in cells reduced the ability of FcRn to transport IgG across epithelial surfaces and resulted in reduced half-life of the molecule. This observation could help explain the association of HCMV with severe congenital infection (73). It is proposed that US11 may help HCMV avoid contact with IgG by accelerating the catabolism of FcRn. This property of HCMV would be especially important after virus reactivation in order to maintain long-term infection and shedding in its host.

FcRn is normally glycosylated prior to assuming its active conformation. These glycation moieties may inhibit entry into the proteasome. It is postulated that N-glycanase likely removes these glycans following FcRn dislocation from the ER. During the studies, a deglycosylated form of FcRn was detected only in the cytosol (FIG. 6E). Because the deglycosylated FcRn intermediates are not observed in the absence of proteasomal inhibitors, this suggests that the dislocation from the ER and proteasomal degradation may be tightly coupled. This assumption is supported by evidence that the C-terminal region of Derlin-1 interacts with the cytosolic proteasomal protein AAA ATPase p97 (74, 75). Therefore, it is suspected that p97 may interact with Derlin-1-bound FcRn HC to provide the activation energy necessary for FcRn extraction from the ER membrane into the cytosol for proteasomal degradation. The results imply that the cytosolic region of FcRn is involved in ERAD substrate binding and this interaction is critical for the Derlin-1-mediated dislocation of FcRn to the cytosol during US11-induced FcRn degradation.

Figure 21C:
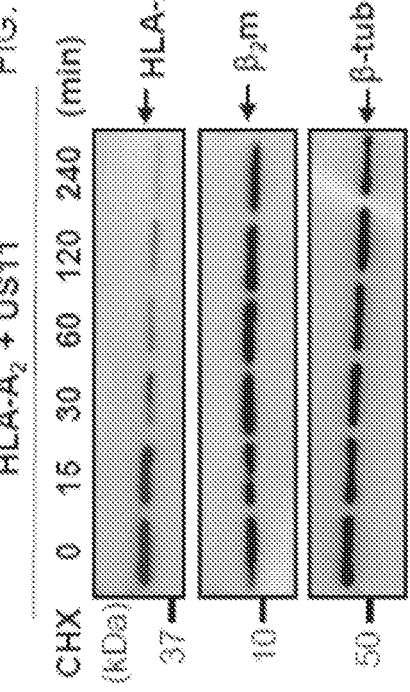
Figure 21D:
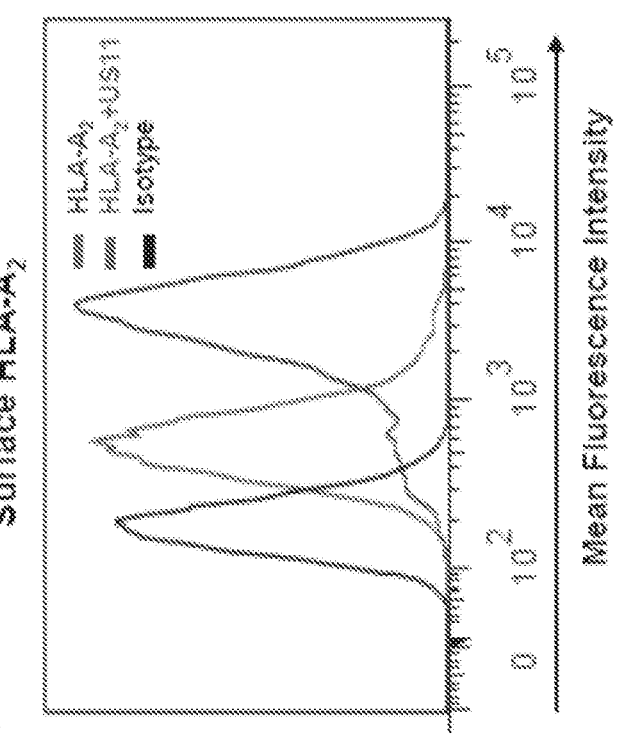
Figure 22:
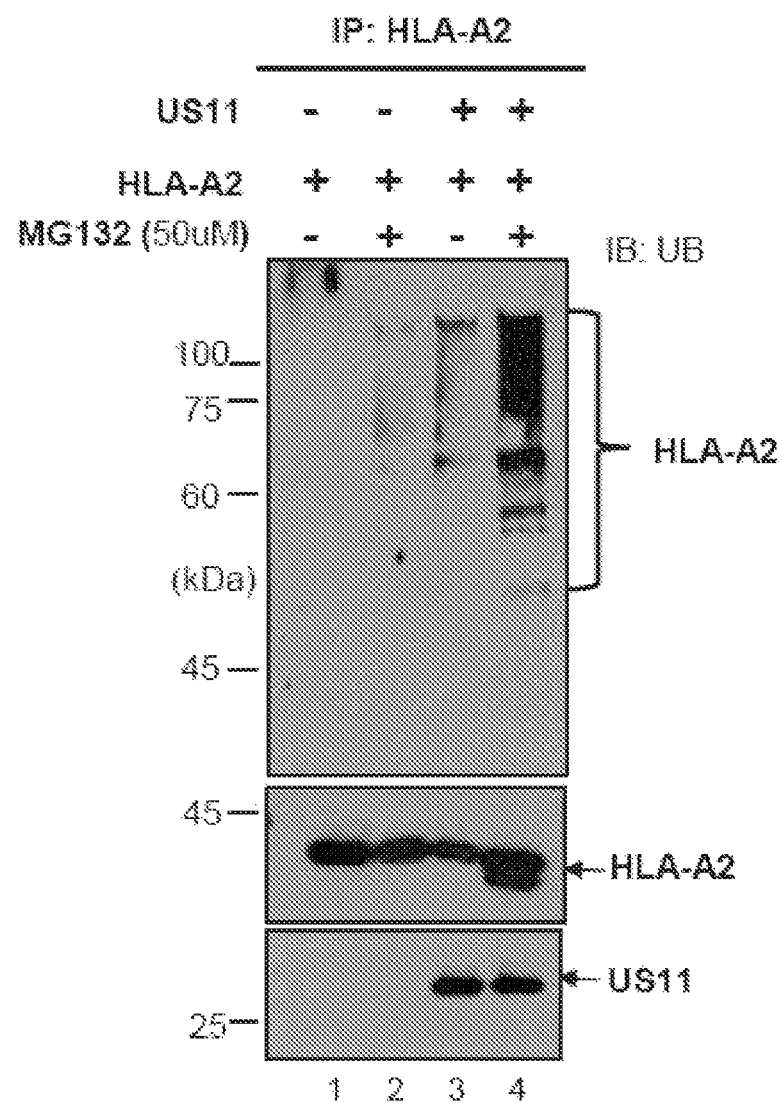
FIG. 22. MHC class I is ubiquitinated in the presence of US11 expression and MG132 treatment. The HeLa$^{HLA-A2+US11}$ and HeLa$^{HLA-A2}$ cells were treated with proteasome inhibitor MG132 (50 µM) for 2 hr, as indicated. The HeLa$^{HLA-A2+US11}$ and HeLa$^{HLA-A2}$ cells were lysed. The cell lysates (0.5 mg) were immunoprecipitated with mAb anti-FLAG for HLA-A2. The immunoprecipitates were subjected to the electrophoresis and immunoblotting analysis to detect ubiquitin and the target proteins HLA-A2 or US11, as indicated.

US11 has previously been shown to degrade MHC class I molecules through a Derlin-1/TMEM129 mediated ERAD system, thereby hindering the recognition of infected cells by $CD8^+$ cytotoxic T cells (11, 76). This finding has been verified in the present study (FIGS. 21 & 22). However, our discovery of US11-mediated FcRn degradation is unexpected because FcRn has limited homology with MHC-I molecules. To degrade MHC-I, US11 binds to the ER luminal domain of MHC-I HC and to the transmembrane domain of Derlin-1 (56), leading to the ubiquitination of MHC-1 by TMEM129 (59, 60). The last two amino acids valine and alanine at the C-terminus of the MHC-I molecules are conserved (77) and may be the target of Derlin-1 recognition (78). Previous studies reported the HCMV protein US2 (79) can also induce rapid degradation of newly synthesized MHC-I in contrast to the US11-mediated FcRn degradation described here. It has been found that HCMV US2 fails to induce FcRn degradation. It is suspected that HCMV is likely to possess multiple immune-modulating proteins to degrade MHC-I molecules due to their highly polymorphic nature but FcRn is relatively non-polymorphic. Most surprisingly, it has been found that this US11-mediated ERAD degradation mechanism evades both cellular and humoral immunity, thus providing HCMV an efficient option to evade the human immune responses in a broad sense.

The precise sites of ubiquitination in US11-induced FcRn degradation remain undefined. Human FcRn contains a single lysine residue in its cytoplasmic tail (54)—whether this lysine residue is critical for FcRn ubiquitination merits further investigation. Ubiquitination is known to occur at nonlysine residues, including serine, threonine, and cysteine (80, 81). Both serine and threonine residues appear in the cytoplasmic tail of FcRn (54) leading to the possibility of multiple ubiquitin acceptor sites. In addition, the E3 ubiquitin ligase TMEM129 contains an atypical RING-C2 domain that may be able to ubiquitinate a combination of lysine and non-lysine residues. A pattern of non-standard ubiquitination would be consistent with the activity of TMEM129's cognate E2, Ube2J2, which is recruited by the MHVγ68 mK3 viral E3 ligase for ubiquitination of MHC-I on nonlysine residues (81). US11 has also been observed to degrade MHC-I molecules that do not contain lysine residues (82), further supporting our notion that TMEM129-dependent ubiquitination of FcRn HC may occur on a combination of lysine and nonlysine residues. Second, it is proposed that US11 inhibits intracellular trafficking of FcRn, leading to decreased IgG transcytosis and increased IgG catabolism. These mechanisms cannot be currently tested in vivo as HCMV is highly species-specific and no animal model is available. Cytomegalovirus strains exist that infect mice and guinea pigs and it will be interesting to know whether these strains also cause FcRn degradation. Third, Hansen et. al. previously reported that approximately 50% of rhesus macaques vaccinated with rhesus cytomegalovirus (RhCMV) vectors expressing simian immunodeficiency virus (SIV) proteins were capable of controlling infection with the highly pathogenic SIVmac239 strain (83). This result appears paradoxical, due to HCMV US11's potent ability to reduce MHC-I levels, alter antigen presentation, and inhibit FcRn. However, it remains to be seen whether RhCMV US11 has a related function to that of HCMV US11. Finally, FcRn has an important role in the development of autoimmune disease (84) because it prolongs the half-life of autoreactive IgG. Thus, HCMV US11 might serve as a treatment for patients with autoimmune disease by blocking FcRn function and facilitating the destruction of autoreactive IgG.

Figure 9:
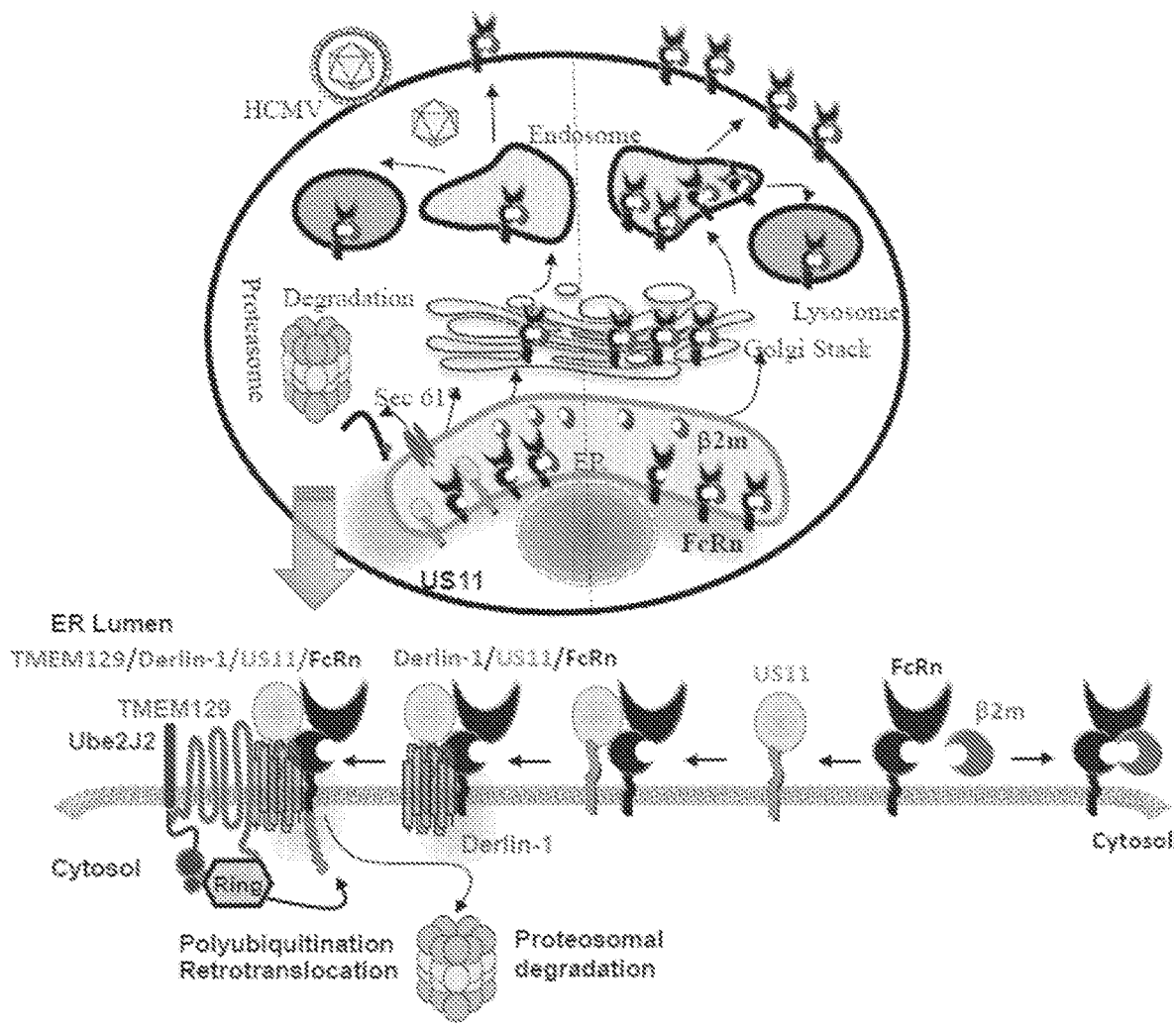
FIG. 9. Model for US11 interaction with FcRn. In uninfected cells (right), FcRn traffics to the endosome and reaches the cell surface through the secretory pathway and recycles between the plasma membrane and endosomes via endocytosis. In HCMV-infected cells or in cells expressing US11 (left), a portion of the β$_2$m-free FcRn HC molecules is associated with US11 in the ER. US11-bound FcRn is rapidly ubiquitinated by TMEM129 E3 ligase and subsequently dislocated to the cytosol for proteasomal degradation. TMEM129 is recruited to US11 via Derlin-1. The portion of FcRn engaged by US11 is targeted for proteasome degradation by ER 'dislocation'.

In conclusion, a mechanism is defined by which US11 suppresses humoral immunity through the inhibition of FcRn. A mechanism for the role of US11 as a humoral immune suppressor is therefore introduced. A model is proposed which details how HCMV US11 dislocates FcRn to the cytosol for subsequent proteasomal degradation (FIG. 9). The present characterization of HCMV US11-induced FcRn ubiquitination as a target by the ERAD system therefore not only uncovers a function for the ERAD pathway, but may better help in understanding HCMV pathogenesis, treating viral diseases, and designing effective vaccines. Due to the global prevalence of HCMV infection and the important roles for FcRn in IgG transport and catabolism, this study may impact work in multiple fields including infectious disease, rheumatology, and oncology.

REFERENCES

1. Rawlinson W D, et al. Congenital cytomegalovirus infection in pregnancy and the neonate: consensus recommendations for prevention, diagnosis, and therapy. Lancet Infect Dis. 2017; 17:e177-e188.
2. Klenerman P, Oxenius A. T cell responses to cytomegalovirus. Nat Rev Immunol. 2016; 16:367-77.
3. Biron C A, Byron K S, Sullivan J L. Severe herpesvirus infections in an adolescent without natural killer cells. N Engl J Med. 1989; 320:1731-1735.
4. Kuijpers T W, et al. Human NK cells can control CMV infection in the absence of T cells. Blood. 2008; 112:914-915
5. Ahn K, et al. The ER-luminal domain of the HCMV glycoprotein US6 inhibits peptide translocation by TAP. Immunity. 1997; 6:613-621.
6. Hengel H, et al. A viral ER-resident glycoprotein inactivates the MHC-encoded peptide transporter. Immunity. 1997; 6:623-632.
7. Lehner P J, Karttunen J T, Wilkinson G W, Cresswell P. The human cytomegalovirus US6 glycoprotein inhibits transporter associated with antigen processing-dependent peptide translocation. Proc Natl Acad Sci USA. 1997; 94:6904-6809.
8. Jones T R, et al. Human cytomegalovirus US3 impairs transport and maturation of major histocompatibility complex class I heavy chains. Proc Natl Acad Sci USA. 1996; 93:11327-11333.
9. Ahn K, et al. Human cytomegalovirus inhibits antigen presentation by a sequential multistep process. Proc Natl Acad Sci USA. 1996; 93:10990-10995.
10. Park B, Spooner E, Houser B L, Strominger J L, Ploegh H L. The HCMV membrane glycoprotein US10 selectively targets HLA-G for degradation. J Exp Med. 2010; 207:2033-2041.
11. Wiertz E J, et al. The human cytomegalovirus US11 gene product dislocates MEW class I heavy chains from the endoplasmic reticulum to the cytosol. Cell. 1996; 84:769-779.
12. Jones T R, Sun L. Human cytomegalovirus US2 destabilizes major histocompatibility complex class I heavy chains. J Virol. 1997; 71:2970-2979.
13. Machold R P, Wiertz E J, Jones T R, Ploegh H L. The HCMV gene products US11 and US2 differ in their ability to attack allelic forms of murine major histocompatibility complex (MHC) class I heavy chains. J Exp Med. 1997; 185:363-366.
14. Tomazin R, et al. Cytomegalovirus US2 destroys two components of the MHC class II pathway, preventing recognition by CD4+ T cells. Nat Med. 1999; 5:1039-1043.
15. Farrell H E, et al. Inhibition of natural killer cells by a cytomegalovirus MHC class I homologue in vivo. Nature. 1997; 386:510-514.
16. Dunn C, et al. Human cytomegalovirus glycoprotein UL16 causes intracellular sequestration of NKG2D ligands, protecting against natural killer cell cytotoxicity. J Exp Med. 2003; 197:1427-1439.
17. Tomasec P, et al. Downregulation of natural killer cell-activating ligand CD155 by human cytomegalovirus UL141. Nat Immunol. 2005; 6:181-188.
18. Chalupny N J, Rein-Weston A, Dosch S, Cosman D. Down-regulation of the NKG2D ligand MICA by the human cytomegalovirus glycoprotein UL142. Biochem Biophys Res Commun. 2006; 346:175-181.
19. Stern-Ginossar N, et al. Host immune system gene targeting by a viral miRNA. Science. 2007; 317:376-381.
20. Kim Y, et al. Human cytomegalovirus UL18 utilizes US6 for evading the NK and T-cell responses. PLoS Pathog. 2008; 4:e1000123.
21. Nachmani D, Stern-Ginossar N, Sarid R, Mandelboim O. Diverse herpesvirus microRNAs target the stress-induced immune ligand MICB to escape recognition by natural killer cells. Cell Host Microbe. 2009; 5:376-385.
22. Prod'homme V, et al. Human cytomegalovirus UL141 promotes efficient downregulation of the natural killer cell activating ligand CD112. J Gen Virol. 2010; 91:2034-2039.
23. Fielding C A, et al. Control of immune ligands by members of a cytomegalovirus gene expansion suppresses natural killer cell activation. Elife. 2017; 6. pii: e22206.
24. Nimmerjahn F, Ravetch J V. Fcgamma receptors as regulators of immune responses. Nat Rev Immunol. 2008; 8:34-47.
25. Klein M, Schoppel K, Amvrossiadis N, Mach M. Strain-specific neutralization of human cytomegalovirus isolates by human sera. J Virol. 1999; 73: 878-886.

26. Bowden R A, et al. Cytomegalovirus immune globulin and seronegative blood products to prevent primary cytomegalovirus infection after marrow transplantation. N Engl J Med. 1986; 314:1006-1010.
27. Ross S A, et al. Cytomegalovirus reinfections in healthy seroimmune women. J Infect Dis. 2010; 201:386-389.
28. Kropff B, et al. Glycoprotein N of human cytomegalovirus protects the virus from neutralizing antibodies. PLoS Pathog. 2012; 8:e1002999.
29. Manley K, et al. Human cytomegalovirus escapes a naturally occurring neutralizing Ab by incorporating it into assembling virions. Cell Host Microbe. 2011; 10:197-209.
30. Atalay R, et al. Identification and expression of human cytomegalovirus transcription units coding for two distinct Fcgamma receptor homologs. J Virol. 200; 76:8596-8608.
31. Sprague E R, et al. The human cytomegalovirus Fc receptor gp68 binds the Fc CH2-CH3 interface of immunoglobulin G. J Virol. 2008; 82:3490-3499.
32. Corrales-Aguilar E, et al. Human cytomegalovirus Fcγ binding proteins gp34 and gp68 antagonize Fcγ receptors I, II and III. PLoS Pathog. 2014; 10(5):e1004131.
33. Simister N E, Mostov K E. An Fc receptor structurally related to WIC class I antigens. Nature. 1989; 337:184-187
34. Burmeister W P, Gastinel L N, Simister N E, Blum M L, Bjorkman P J. Crystal structure at 2.2 A resolution of the MHC-related neonatal Fc receptor. Nature. 1994; 372: 336-343.
35. Zhu X, et al. The heavy chain of neonatal Fc receptor for IgG is sequestered in endoplasmic reticulum by forming oligomers in the absence of beta2-microglobulin association. Biochem J. 2002; 367:703-714.
36. Zeng Z, et al. Crystal structure of mouse CD1: An WIC-like fold with a large hydrophobic binding groove. Science. 1997; 277:339-345.
37. Raghavan M, Gastinel L N, Bjorkman P J. The class I major histocompatibility complex related Fc receptor shows pH-dependent stability differences correlating with immunoglobulin binding and release. Biochemistry. 1993; 32:8654-8660.
38. Roopenian D C, Akilesh S. FcRn: the neonatal Fc receptor comes of age. Nat Rev Immunol. 2007; 7:715-725.
39. Dickinson B L, et al. Bidirectional FcRn-dependent IgG transport in a polarized human intestinal epithelial cell line. J Clin Invest. 1999; 104:903-911.
40. Spiekermann G M, et al. Receptor-mediated immunoglobulin G transport across mucosal barriers in adult life: functional expression of FcRn in the mammalian lung. J Exp Med. 2002; 196:303-310.
41. Li Z, et al. Transfer of IgG in the female genital tract by WIC class I-related neonatal Fc receptor (FcRn) confers protective immunity to vaginal infection. Proc Natl Acad Sci USA. 2011; 108:4388-4393.
42. Kuo T T, et al. Neonatal Fc receptor: from immunity to therapeutics. J Clin Immunol. 2010; 30:777-789.
43. Ye L, Zeng R, Bai Y, Roopenian D C, Zhu X. Efficient mucosal vaccination mediated by the neonatal Fc receptor. Nat Biotechnol. 2011; 29:158-163.
44. Sockolosky J T, Szoka F C. The neonatal Fc receptor, FcRn, as a target for drug delivery and therapy. Adv Drug Deliv Rev. 2015; 91:109-124.
45. Maciejewski J P, et al. Infection of hematopoietic progenitor cells by human cytomegalovirus. Blood. 1992; 80:170-178.
46. Plachter B, Sinzger C, Jahn G. Cell types involved in replication and distribution of human cytomegalovirus. Adv Virus Res. 1996; 46:195-261.
47. Maidji E, Genbacev O, Chang H T, Pereira L. Developmental regulation of human cytomegalovirus receptors in cytotrophoblasts correlates with distinct replication sites in the placenta. J Virol. 2007; 81:4701-4712.
48. Firan M, et al. The MHC class I-related receptor, FcRn, plays an essential role in the maternofetal transfer of gamma-globulin in humans. Int Immunol. 2001; 13:993-1002.
49. Ward E S, Zhou J, Ghetie V, Ober R J. Evidence to support the cellular mechanism involved in serum IgG homeostasis in humans. Int Immunol. 2003; 15:187-195.
50. Zhu X, et al. MHC class I-related neonatal Fc receptor for IgG is functionally expressed in monocytes, intestinal macrophages, and dendritic cells. J Immunol. 2001; 166: 3266-3276.
51. Maidji E, McDonagh S, Genbacev O, Tabata T, Pereira L. Maternal antibodies enhance or prevent cytomegalovirus infection in the placenta by neonatal Fc receptor-mediated transcytosis. Am J Pathol. 2006; 168:1210-1226.
52. Ye L, et al. The MHC class II-associated invariant chain interacts with the neonatal Fc gamma receptor and modulates its trafficking to endosomal/lysosomal compartments. J Immunol. 2008; 181:2572-2585.
53. Zhu X, et al. Calnexin and ERp57 facilitate the assembly of the neonatal Fc receptor for IgG with beta 2-microglobulin in the endoplasmic reticulum. J Immunol. 2005; 175:967-976.
54. Story C M, Mikulska J E, Simister N E. A major histocompatibility complex class I-like Fc receptor cloned from human placenta: possible role in transfer of immunoglobulin G from mother to fetus. J Exp Med. 1994; 180:2377-2381.
55. Ye Y, Shibata Y, Yun C, Ron D, Rapoport T A. A membrane protein complex mediates retro-translocation from the ER lumen into the cytosol. Nature. 2004; 429: 841-847.
56. Lilley B N, Ploegh H L. A membrane protein required for dislocation of misfolded proteins from the ER. Nature. 2004; 429:834-840.
57. Mehnert M, Sommer T, Jarosch E. Derl promotes movement of misfolded proteins through the endoplasmic reticulum membrane. Nat Cell Biol. 2014; 16:77-86.
58. Lilley B N, Tortorella D, Ploegh H L. Dislocation of a type I membrane protein requires interactions between membrane-spanning segments within the lipid bilayer. Mol Biol Cell. 2003; 14:3690-3698.
59. van den Boomen D J, et al. TMEM129 is a Derlin-1 associated ERAD E3 ligase essential for virus-induced degradation of MHC-I. Proc Natl Acad Sci USA. 2014; 111:11425-11430.
60. van de Weijer M L, et al. A high-coverage shRNA screen identifies TMEM129 as an E3 ligase involved in ER-associated protein degradation. Nat Commun. 2014; 5:3832.
61. von Heijne G. Control of topology and mode of assembly of a polytopic membrane protein by positively charged residues. Nature. 1989; 341:456-458.
62. Kostova Z, Tsai Y C, Weissman A M. Ubiquitin ligases, critical mediators of endoplasmic reticulum-associated degradation. Semin Cell Dev Biol. 2007; 18:770-779.
63. Esclatine A, Lemullois M, Servin A L, Quero A M, Geniteau-Legendre M. Human cytomegalovirus infects 64. Ward E S, Ober R J. Chapter 4: Multitasking by exploitation of intracellular transport functions the many faces of FcRn. Adv Immunol. 2009; 103:77-115.
65. Ober R J, Martinez C, Vaccaro C, Zhou J, Ward E S. Visualizing the site and dynamics of IgG salvage by the MHC class I-related receptor, FcRn. J Immunol. 2004; 172:2021-2029.
66. Tesar D B, Tiangco N E, Bjorkman P J. Ligand valency affects transcytosis, recycling and intracellular trafficking mediated by the neonatal Fc receptor. Traffic. 2006; 7:1127-1142.
67. Hegde R S, Ploegh H L. Quality and quantity control at the endoplasmic reticulum. Curr Opin Cell Biol. 2010; 22:437-446.
68. Guerriero C J, Brodsky J L. The delicate balance between secreted protein folding and endoplasmic reticulum-associated degradation in human physiology. Physiol Rev. 2012; 92:537-576.
69. Olzmann J A, Kopito R R, Christianson J C. The mammalian endoplasmic reticulum-associated degradation system. Cold Spring Harb Perspect Biol. 2013; 5. pii: a013185.
70. Randow F, Lehner P J. Viral avoidance and exploitation of the ubiquitin system. Nat Cell Biol. 2009;11:527-534.
71. Isaacson M K, Ploegh H L. Ubiquitination, ubiquitin-like modifiers, and deubiquitination in viral infection. Cell Host Microbe. 2009; 5:559-570.
72. Lee S O, et al. Functional dissection of HCMV US11 in mediating the degradation of MHC class I molecules. Biochem Biophys Res Commun. 2005; 330:1262-1267.
73. Hamprecht K, Maschmann J, Jahn G, Poets C F, Goelz R. Cytomegalovirus transmission to preterm infants during lactation. J Clin Virol. 2008; 41:198-205.
74. Greenblatt E J, Olzmann J A, Kopito R R. Derlin-1 is a rhomboid pseudoprotease required for the dislocation of mutant α-1 antitrypsin from the endoplasmic reticulum. Nat Struct Mol Biol. 2011; 18:1147-1152.
75. Ye Y, Meyer H H, Rapoport T A. The AAA ATPase Cdc48/p97 and its partners transport proteins from the ER into the cytosol. Nature. 2001; 414:652-656.
76. Loureiro J, Ploegh H L. Antigen presentation and the ubiquitin-proteasome system in host-pathogen interactions. Adv Immunol. 2006; 92:225-305.
77. Barel M T, et al. Amino acid composition of alpha1/alpha2 domains and cytoplasmic tail of MHC class I molecules determine their susceptibility to human cytomegalovirus US11-mediated down-regulation. Eur J Immunol. 2003; 33:1707-1716
78. Cho S, Kim B Y, Ahn K, Jun Y. The C-terminal amino acid of the MHC-I heavy chain is critical for binding to Derlin-1 in human cytomegalovirus US11-induced MHC-I degradation. PLoS One. 2013; 8:e72356. doi: 10.1371
79. Chevalier M S, Daniels G M, Johnson D C. Binding of human cytomegalovirus US2 to major histocompatibility complex class I and II proteins is not sufficient for their degradation. J Virol. 2002; 76:8265-8275.
80. Cadwell K, Coscoy L. Ubiquitination on nonlysine residues by a viral E3 ubiquitin ligase. Science. 2005; 309:127-130.
81. Wang X, Ye Y, Lencer W, Hansen T H. The viral E3 ubiquitin ligase mK3 uses the Derlin/p97 endoplasmic reticulum-associated degradation pathway to mediate down-regulation of major histocompatibility complex class I proteins. J Biol Chem. 2006; 281:8636-8344.
82. Hassink G C, Barel M T, Van Voorden S B, Kikkert M, Wiertz E J. Ubiquitination of MHC class I heavy chains is essential for dislocation by human cytomegalovirus-encoded US2 but not US11. J Biol Chem. 2006; 281: 30063-30071.
83. Hansen S G, et al. Cytomegalovirus vectors violate CD8+ T cell epitope recognition paradigms. Science. 2013; 340:1237874.
84. Akilesh S, et al. The MHC class I-like Fc receptor promotes humorally mediated autoimmune disease. J Clin Invest. 2004; 113:1328-1333.
85. Burr M L, et al. HRD1 and UBE2J1 target misfolded MHC class I heavy chains for endoplasmic reticulum-associated degradation. Proc Natl Acad Sci USA. 2011; 108:2034-2039.
86. Bai Y, et al. Intracellular neutralization of viral infection in polarized epithelial cells by neonatal Fc receptor (FcRn)-mediated IgG transport. Proc Natl Acad Sci USA. 2011; 108:18406-18411.
87. Grevys A, et al. A human endothelial cell-based recycling assay for screening of FcRn targeted molecules. Nat Commun. 2018; 9:621.

What is claimed is:

1. A pharmaceutical composition comprising an engineered, purified human cytomegalovirus (HCMV) US11 protein and a pharmaceutically acceptable carrier, wherein said HCMV US11 protein is not associated with a HCMV virion.

2. The pharmaceutical composition of claim 1, wherein the HCMV US11 protein is a polypeptide of SEQ ID NO:1, a polypeptide having at least about 90% or more homology with the HCMV US11 protein of SEQ ID NO: 1 or a polypeptide fragment thereof that retains the ability to inhibit the activity of FcRn.

3. The pharmaceutical composition of claim 1, wherein the HCMV US11 protein is associated with a lipid based composition.

4. The pharmaceutical composition of claim 1, wherein the HCMV US 11 protein is delivered by way of a cell engineered to express an HCMV US11 protein.

5. The pharmaceutical composition of claim 1, further comprising an agent that targets the HCMV US11 protein to a target cell.

6. The pharmaceutical composition of claim 1, wherein said pharmaceutical composition results in a reduction in production of autoantibodies when administered to a subject suffering from an antibody-mediated autoimmune disease.

7. The pharmaceutical composition of claim 1, for use in treatment of an albumin-mediated disease.

8. The pharmaceutical composition of claim 6, further comprising a second therapeutic useful for treatment of the antibody-mediated autoimmune disease.

9. The pharmaceutical composition of claim 6, wherein the antibody-mediated autoimmune disease is selected from the group consisting of ankylosing spondylitis, lupus, rheumatoid arthritis, juvenile arthritis, scleroderma dermatomyositis, Behcet's disease, reactive arthritis, mixed connective tissue disease, Raynard's phenomenon, giant cell arteritis/temporal arteritis, polymyalgia rheumatica, polyarteritis nodosa, polymyositis, Takayasu arteritis, granulomatosis with polyangiitis, vasculitis, alopecia areata, antiphospholipid antibody syndrome, autoimmune hepatitis, type 1 diabetes, celiac disease, Crohn's disease, Graves' disease, Guillain-Barre syndrome, Hashimoto's disease, idiopathic thrombocytopenic purpura, inflammatory bowel disease, multiple sclerosis, myasthenia gravis, primary biliary cirrhosis, psoriasis, Sjogren's syndrome, vitiligo, bullous pemphigoid, pemphigus foliaceus, pemphigus vulgaris, and epidermolysis bullosa acquisita.

10. A pharmaceutical composition comprising an engineered, purified HCMV US11-encoding nucleic acid and a pharmaceutically acceptable carrier, wherein said HCMV US11-encoded nucleic acid is not associated with a HCMV virion.

11. The pharmaceutical composition of claim 10, wherein the HCMV US11-encoding nucleic acid encodes for a polypeptide of SEQ ID NO:1, a polypeptide having at least about 90% or more homology with the HCMV US11 protein of SEQ ID NO:1 or a polypeptide fragment thereof that retains the ability to inhibit the activity of FcRn.

12. The pharmaceutical composition of claim 10, wherein the engineered, purified HCMV US11-encoding nucleic acid is associated with a vector.

13. The pharmaceutical composition of claim 12, wherein the vector is a viral vector.

14. The pharmaceutical composition of claim 10, wherein the HCMV US11-encoding nucleic acid is associated with a lipid based composition.

15. The pharmaceutical composition of claim 10, wherein the HCMV US11-encoding nucleic acid is within a cell engineered to express an HCMV US11 protein.

16. The pharmaceutical composition of claim 10, further comprising an agent that targets the HCMV US11-encoding nucleic acid to a target cell.

17. The pharmaceutical composition of claim 10, wherein said pharmaceutical composition results in a reduction in production of autoantibodies when administered to a subject suffering from an antibody-mediated autoimmune disease.

18. The pharmaceutical composition of claim 10, for use in treatment of an albumin-mediated disease.

19. The pharmaceutical composition of claim 17, further comprising a second therapeutic useful for treatment of the antibody-mediated autoimmune disease.

20. The pharmaceutical composition of claim 17, wherein the antibody-mediated autoimmune disease is selected from the group consisting of ankylosing spondylitis, lupus, rheumatoid arthritis, juvenile arthritis, scleroderma dermatomyositis, Behcet's disease, reactive arthritis, mixed connective tissue disease, Raynard's phenomenon, giant cell arteritis/temporal arteritis, polymyalgia rheumatica, polyarteritis nodosa, polymyositis, Takayasu arteritis, granulomatosis with polyangiitis, vasculitis, alopecia areata, antiphospholipid antibody syndrome, autoimmune hepatitis, type 1 diabetes, celiac disease, Crohn's disease, Graves' disease, Guillain-Barre syndrome, Hashimoto's disease, idiopathic thrombocytopenic purpura, inflammatory bowel disease, multiple sclerosis, myasthenia gravis, primary biliary cirrhosis, psoriasis, Sjogren's syndrome, vitiligo, bullous pemphigoid, pemphigus foliaceus, Pemphigus vulgaris, and epidermolysis bullosa acquisita.

21. The pharmaceutical composition of claim 10, wherein said HCMV US11-encoding nucleic acid is an RNA molecule.

\* \* \* \* \*

SEQUENCE LISTING

```
Sequence total quantity: 11
SEQ ID NO: 1             moltype = AA  length = 215
FEATURE                  Location/Qualifiers
REGION                   1..215
                         note = Synthetic: HCMV US11
source                   1..215
                         mol_type = protein
                         organism = synthetic construct
SEQUENCE: 1
MNLVMLILAL WAPVAGSMPE LSLTLFDEPP PLVETEPLPP LSDVSEYRVE YSEARCVLRS   60
GGRLEALWTL RGNLSVPTPT PRVYYQTLEG YADRVPTPVE DVSESLVAKR YWLRDYRVPQ  120
RTKLVLFYFS PCHQCQTYYV ECEPRCLVPW VPLWSSLEDI ERLLFEDRRL MAYYALTIKS  180
AQYTLMMVAV IQVFWGLYVK GWLHRHFPWM FSDQW                            215

SEQ ID NO: 2             moltype = DNA  length = 778
FEATURE                  Location/Qualifiers
misc_feature             1..778
                         note = Synthetic: nucleic acid sequence encoding US11
                           protein
source                   1..778
                         mol_type = other DNA
```

-continued

```
                            organism = synthetic construct
SEQUENCE: 2
cagccttaca gcttttgagt ctagacaggg gaacagcctt cccttgtaag acagaatgaa    60
ccttgtaatg cttattctag ccctctgggc cccggtcgcg ggtagtatgc ctgaattatc   120
cttgactctt ttcgatgaac ctccgccctt ggtggagacg gagccgttac cgcctctgtc   180
cgatgtttcg gagtaccgag tagagtattc cgaggcgcgc tgcgtgctcc gatcgggcgc   240
tcgactggag gctctgtgga ccctgcgcgg gaacctgtcc gtgcccacgc cgacaccccg   300
ggtgtactac cagacgctgg agggctacgc ggatcgagtg ccgacgccgg tggaggacgt   360
ctccgaaagc ctcgtcgcaa aacgctactg gctccgggac tatcgtgttc cccaacgcac   420
aaaaactcgtg ttgttctact ttccccctg ccaccaatgc caaacttatt atgtagagtg   480
cgaaccccgg tgcctcgtgc cttgggttcc cctgtggagc tcgttagagg acatcgaacg   540
attattgttc gaagatcgcc gtctaatggc gtactacgcg ctcacgatta agtcggcgca   600
gtatacgctg atgatggtgg cagtgattca agtgttttgg gggctgtatg tgaaaggttg   660
gctgcaccga cattttccct ggatgttttc ggaccagtgg tgatatatag actgaagcgg   720
agtgcatctc gagtcgctcg gaaacgactc accagacttt ttgctttaac ccgaaacc    778

SEQ ID NO: 3              moltype = AA  length = 8
FEATURE                   Location/Qualifiers
REGION                    1..8
                          note = Synthetic: anti-FLAG epitope
source                    1..8
                          mol_type = protein
                          organism = synthetic construct
SEQUENCE: 3
DYKDDDDK                                                              8

SEQ ID NO: 4              moltype = AA  length = 9
FEATURE                   Location/Qualifiers
REGION                    1..9
                          note = Synthetic: influenza hemagglutinin epitope
source                    1..9
                          mol_type = protein
                          organism = synthetic construct
SEQUENCE: 4
YPYDVPDYA                                                             9

SEQ ID NO: 5              moltype = AA  length = 10
FEATURE                   Location/Qualifiers
REGION                    1..10
                          note = Synthetic: rabbit anti-Myc Ab
source                    1..10
                          mol_type = protein
                          organism = synthetic construct
SEQUENCE: 5
EQKLISEEDL                                                           10

SEQ ID NO: 6              moltype = DNA  length = 22
FEATURE                   Location/Qualifiers
misc_feature              1..22
                          note = Synthetic: primer
source                    1..22
                          mol_type = other DNA
                          organism = synthetic construct
SEQUENCE: 6
gtacctgagc tacaatagcc tg                                             22

SEQ ID NO: 7              moltype = DNA  length = 22
FEATURE                   Location/Qualifiers
misc_feature              1..22
                          note = Synthetic: primer
source                    1..22
                          mol_type = other DNA
                          organism = synthetic construct
SEQUENCE: 7
cacggaaaag ccagggctgc tg                                             22

SEQ ID NO: 8              moltype = DNA  length = 22
FEATURE                   Location/Qualifiers
misc_feature              1..22
                          note = Synthetic: primer
source                    1..22
                          mol_type = other DNA
                          organism = synthetic construct
SEQUENCE: 8
tggcgtcttc accaccatgg ag                                             22

SEQ ID NO: 9              moltype = DNA  length = 23
FEATURE                   Location/Qualifiers
misc_feature              1..23
```

```
                        note = Synthetic: primer
source                  1..23
                        mol_type = other DNA
                        organism = synthetic construct
SEQUENCE: 9
agttgtcatg gatgaccttg gcc                                              23

SEQ ID NO: 10           moltype = AA  length = 9
FEATURE                 Location/Qualifiers
REGION                  1..9
                        note = Synthetic: integrin-binding peptide
source                  1..9
                        mol_type = protein
                        organism = synthetic construct
SEQUENCE: 10
CYGGRGDTP                                                               9

SEQ ID NO: 11           moltype = AA  length = 45
FEATURE                 Location/Qualifiers
SITE                    1..45
                        note = Human FcRn
source                  1..45
                        mol_type = protein
                        organism = Homo sapiens
SEQUENCE: 11
WRRMRSGLPA PWISLRGDDT GVLLPTPGEA QDADLKDVNV IPATA                       45
```